(12) United States Patent
Biragyn et al.

(10) Patent No.: US 9,605,044 B2
(45) Date of Patent: Mar. 28, 2017

(54) METHODS AND COMPOSITIONS FOR MODULATING IMMUNE TOLERANCE

(71) Applicant: The United States of America, as represented by the Secretary, Department of Health & Human Services, Washington, DC (US)

(72) Inventors: Arya Biragyn, Lutherville, MD (US); Kouji Matsushima, Tokyo (JP); Dolgor Baatar, Parkville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 66 days.

(21) Appl. No.: 14/313,481

(22) Filed: Jun. 24, 2014

(65) Prior Publication Data
US 2014/0341937 A1 Nov. 20, 2014

Related U.S. Application Data

(60) Division of application No. 11/992,880, filed on Sep. 27, 2010, now Pat. No. 8,795,674, which is a continuation of application No. PCT/US2006/038195, filed on Sep. 28, 2006.

(60) Provisional application No. 60/722,675, filed on Sep. 30, 2005.

(51) Int. Cl.
C07K 14/00 (2006.01)
C07K 14/52 (2006.01)
A61K 47/48 (2006.01)
A61K 45/06 (2006.01)
C07K 14/715 (2006.01)
C12N 9/10 (2006.01)
C12N 9/22 (2006.01)

(52) U.S. Cl.
CPC ............ *C07K 14/521* (2013.01); *A61K 45/06* (2013.01); *A61K 47/48261* (2013.01); *A61K 47/48269* (2013.01); *C07K 14/523* (2013.01); *C07K 14/7158* (2013.01); *C12N 9/1077* (2013.01); *C12N 9/22* (2013.01); *C07K 2319/55* (2013.01); *C12Y 204/02036* (2013.01); *C12Y 301/27005* (2013.01)

(58) Field of Classification Search
None
See application file for complete search history.

(56) References Cited

FOREIGN PATENT DOCUMENTS

| EP | 1 346 731 A | 9/2003 |
|----|-------------|--------|
| WO | WO-00/41724 | 7/2000 |
| WO | WO-02/20615 | 3/2002 |

OTHER PUBLICATIONS

Goncalves et al. Epidemiology, Treatment, and Prevention of Human T-Cell Leukemia Virus Type 1-Associated Diseases. Clin Microbiol Rev. Jul. 2010; 23(3): 577-589.*

(Continued)

*Primary Examiner* — Michelle S Horning
(74) *Attorney, Agent, or Firm* — Bryan D. Zerhusen; Locke Lord LLP

(57) ABSTRACT

The instant invention provides methods and compositions for modulation of the immune system. Specifically, the invention provides methods and compositions for increasing T cell mediated immune response useful in the treatment of cancer and chronic infection.

21 Claims, 31 Drawing Sheets

(56) References Cited

OTHER PUBLICATIONS

Ruffini et al. Genetic fusions with viral chemokines target delivery of nonimmunogenic antigen to trigger antitumor immunity independent of chemotaxis. J Leukoc Biol. Jul. 2004;76(1):77-85.*
Hogaboam et al: "The therapeutic potential in targeting CCR5and CXCR4 receptors in infectious and allergic pulmonary disease" Pharmacology and Therapeutics, Elsevier, GB, vol. 107, No. 3, Sep. 1, 2005 (Sep. 1, 2005), pp. 314-328, XP005034671.

* cited by examiner

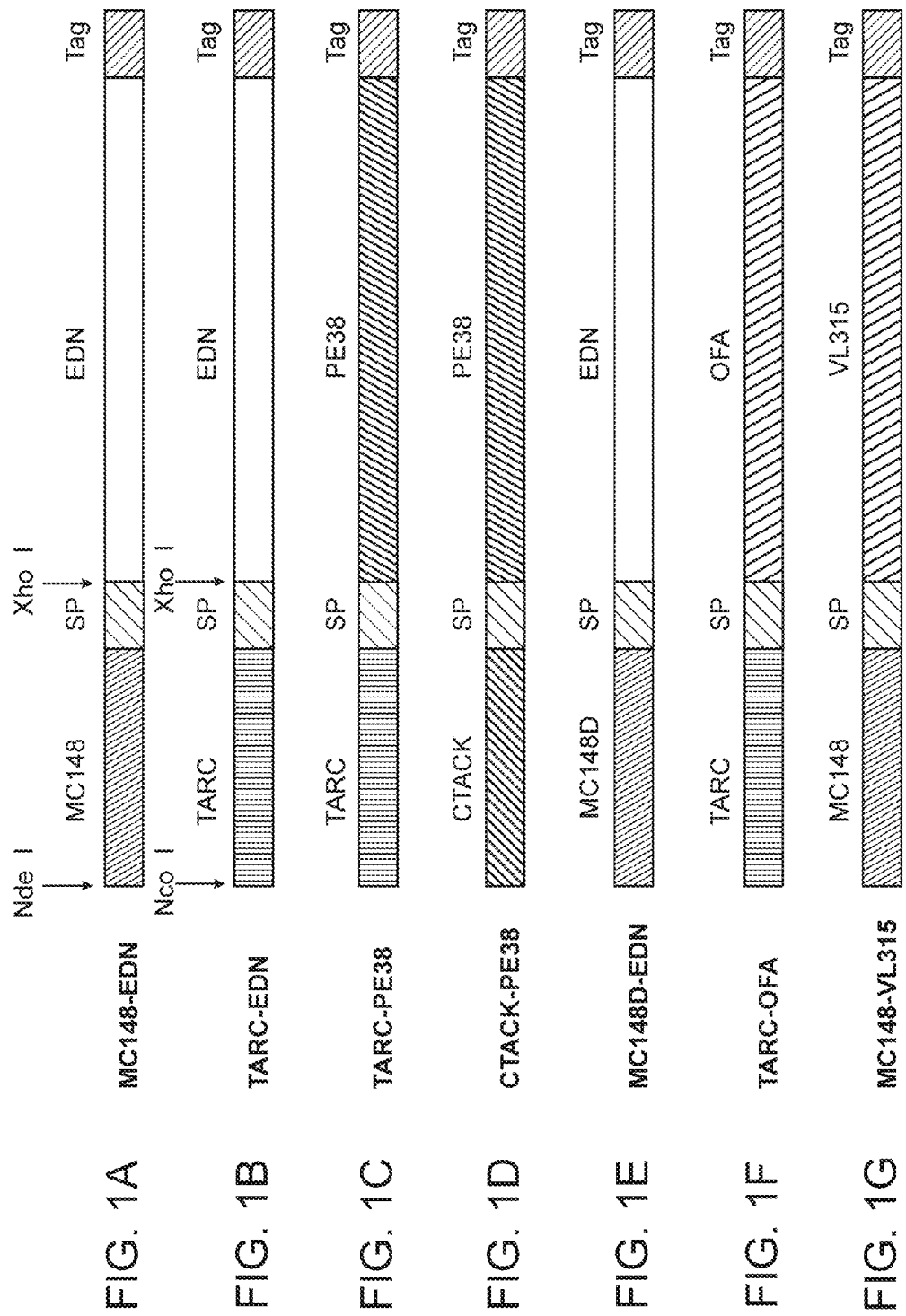

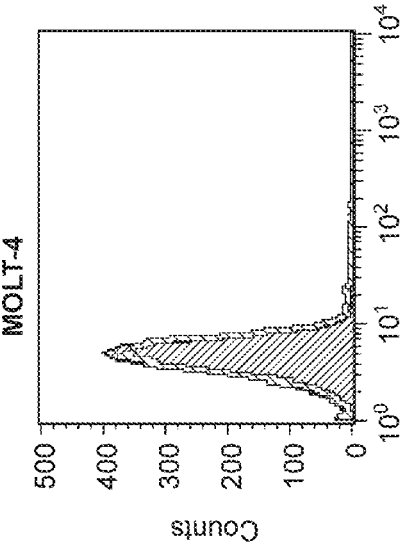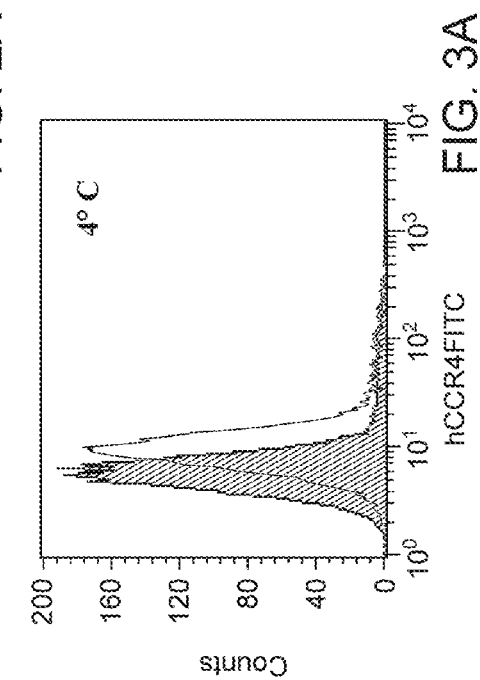

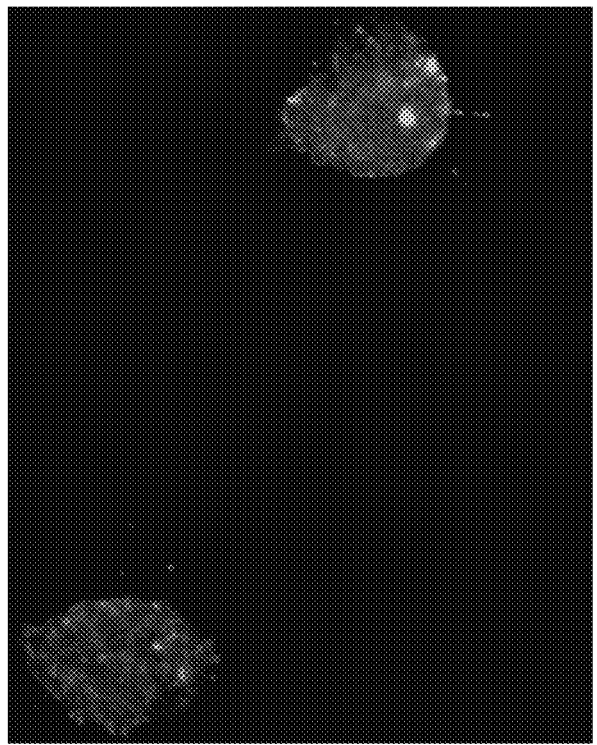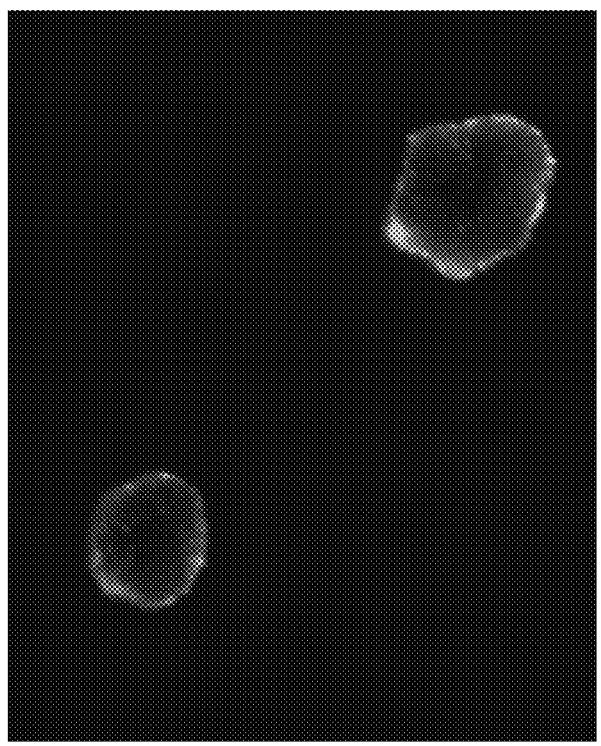
FIG. 8E

1. CD25⁻CCR4⁻
2. CD25⁺CCR4⁻
3. CD25⁺CCR4⁺
4. CD25⁻CCR4⁺

METHODS AND COMPOSITIONS FOR MODULATING IMMUNE TOLERANCE

RELATED APPLICATIONS

This application is a Divisional Application of U.S. patent application Ser. No. 11/992,880 filed Sep. 27, 2010, which is a 35 U.S.C. 371 U.S. National Entry of International Application No. PCT/US2006/038195 having an international filing date of Sep. 28, 2006, which claims benefit of U.S. Provisional Application No. 60/722,675, filed Sep. 30, 2005, each of which are incorporated herein by reference in their entirety.

GOVERNMENT SUPPORT

Research supporting this application was carried out by the United States of America as represented by the Secretary, Department of Health and Human Services.

SEQUENCE LISTING

The instant application contains a Sequence Listing which has been submitted in ASCII format via EFS-Web and is hereby incorporated by reference in its entirety. Said ASCII copy, created on Jul. 2, 2013, is named 63329(47992)_SL.txt and is 26,375 bytes in size.

BACKGROUND OF THE INVENTION

T regulatory cells (Treg) or suppressor T cells are functionally defined as T cells that inhibit the immune response by influencing the activity of another cell. These cells comprise a small population of thymus derived $CD4^+$ T cells. Despite there small population, these T regulatory cells have a large regulatory effect on the immune system. Overactivity of these T regulatory cells can contribute to the resistance of tumors and infections to the immune system, where this resistance may take the form of, e.g., tolerance to the tumor, progressing lesions in cancer, and persistent bacterial and viral infections, see, e.g., Shimizu, et al. (2002) *Nat. Immunol.* 3:135-142; Shimizu, et al. (1999) *J. Immunol.* 163:5211-5218; Antony and Restifo (2002) *J. Immunotherapy* 25:202-206; McGuirk and Mills (2002) *Trends Immunol.* 23:450-455; Tatsumi, et al. (2002) *J. Exp. Med.* 196:619-628; Jonuleit, et al. (2001) *Trends Immunol.* 22:394-400.

Additionally, T regulatory cells mediate inflammatory and autoimmune disorders. For example, $CD25^+CD4^+$ T regulatory cells play a role in preventing, e.g., autoimmune gastritis, thyroiditis, insulin-dependent diabetes melitus (IDDM), inflammatory bowel disorders (IBD), experimental autoimmune encephalomyelitis (EAE), food allergies, and graft rejection. Conversely, impaired T regulatory cell activity can promote autoimmune disorders, see, e.g., Wing, et al. (2003) *Eur. J. Immunol.* 33:579-587; Sakaguchi, et al. (2001) *Immunol. Revs.* 182:18-32; Sufi-Payer, et al. (1998) *J. Immunol.* 160:1212-1218; Shevach (2001) *J. Exp. Med.* 193:F41-F45; Read and Powrie (2001) *Curr. Op. Immunol.* 13:644-649.

To function properly, the immune system must discriminate between self and non-self. When self/non-self discrimination fails the immune system destroys cells and tissues of the body and as a result causes autoimmune diseases. Regulatory T cells actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells.

Moreover, large numbers of these regulatory cells have been found in cancerous tissue. The presence of regulatory T cells at the site of a tumor results in the creation of a favorable environment for tumor growth. Ideally, the presence and action of T regulatory cells at the site of tumor growth would be reduced so that an immune response could be mounted to the growing tumor.

The molecular mechanism by which regulatory T cells exert their suppressor/regulatory activity has not been definitively characterized and is the subject of intense research. In vitro experiments suggest that suppressive mechanism requires cell-to-cell contact with the cell being suppressed. However, the immunosuppressive cytokines TGF-beta and interleukin-10 (IL-10) have also been implicated in regulatory T cell function.

Despite numerous attempts and reports, immunotherapeutic intervention does not often generate long lasting effector T cell responses and therapeutic immunity. T regulatory (Treg) cells play a central role in regulation of self-tolerance and control of responses to alloantigens. They comprise 5-10% of all $CD4^+$ T cells, constitutively express the CD25 and CTLA-4 markers and suppress the activation of effector $CD4^+$ and $CD8^+$ cells and even dendritic cells. They have been implicated in wide variety of immunosuppressive responses, such as maternal tolerance to the fetus, autoimmunity and tumor survival. Dysfunction or depletion of Treg cells lead to spontaneous onset of various immune or autoimmune disorders, such as organ-specific autoimmune diseases in mice or nickel-allergic responses in humans. As recently reported, two subsets of Treg cells, natural and adaptive, differ in terms of specificity and effector mechanisms (Bluestone et al. (2003) *Nat Rev Immunol.* 3:253-7). While the natural Treg cell subset develops in the thymus to prevent potentially pathological autoimmune reactions, the adaptive Treg cells develop as result of activation of mature T cells under particular conditions of sub-optimal antigen exposure and co-stimulation (Bluestone et al. supra). Treg-mediated suppressive activity has been shown to be both cell-cell contact independent and dependent. For example, antigen-specific tumor infiltrating human $CD4^+CD25^+$ Treg cells requires cell contact and ligand-specific activation (via LAGE protein). Treg cells migration, particularly skin-homing, is controlled by chemokines, which signal via binding to differentially expressed chemokine receptors, namely CCR4 and CCR8 (thus, these cells are attracted to MDC/CCL22, TARC/CCL17, I-309/CCL1 or viral chemokine vMIP-I and vMIP-III (Iellem et al. (2001) *J Exp Med.* 194:847-53). Chemokine receptors are also differentially expressed on various immune cells. For example, cutaneous T cell lymphoma and adult T-cell leukemia/lymphoma (ATLL) cells over express CCR4, which was recently associated with unfavorable outcome of the disease (Ishida et al. (2003) *Clin Cancer Res.* 9:3625-34). In fact, expression of CCR4 was also associated with skin homing of Tregs and the infiltration of Tregs at tumor site, including B cell malignancies which produce CCL2 (Scrivner et al. (2003) *Leuk Lymphoma.* 44:383-9).

Due to the involvement of T regulatory cells in the progression of many diseases and disorders, the need exists to be able to modulate the activity of these T cells and, ultimately, the entire immune system, for the treatment of these diseases and disorders.

SUMMARY OF THE INVENTION

The instant invention is based, at least in part, on the discovery that fusion molecules comprising a chemokine fused to a toxin moiety, optionally including a linker, are capable of depleting T regulatory cells. These molecules are useful in the treatment of cancer, and autoimmunity, and further, can be used for efficient administration of a vaccine, e.g., a cancer vaccine.

Accordingly, in one aspect, the instant invention provides a method for increasing T cell mediated immune response in a subject by administering to the subject a fusion molecule comprising a chemokine receptor ligand and a toxin moiety, thereby increasing the T cell mediated immune response.

In one embodiment, the subject has cancer, e.g., a T cell malignancy such as cutaneous T cell leukemia and myeloma. In another embodiment, the subject has a chronic infection, e.g., HIV infection, HCV infection, HBV infection and TB infection.

In another embodiment, the fusion molecule is administered near the location of a tumor.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1. In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In another aspect, the invention provides a method of locally depleting T regulatory cells in a subject by locally administering to the subject a fusion molecule comprising a chemokine receptor ligand and a toxin moiety, thereby depleting the T regulatory cells in the area of the administration of the fusion molecule.

In one embodiment, the subject has cancer, e.g., a T cell malignancy such as cutaneous T cell leukemia and myeloma. In another embodiment, the subject has a chronic infection, e.g., HIV infection, HCV infection, HBV infection and TB infection.

In another embodiment, the fusion molecule is administered near the location of a tumor.

In another embodiment, the method involves administering the subject a vaccine near the location of the administration of the fusion molecule.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1. In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In another aspect, the instant invention provides a method of inhibiting immune suppression in a subject by administering to the subject a fusion molecule comprising a chemokine receptor ligand and a toxin moiety, thereby inhibiting immune suppression in the subject.

In one embodiment, the subject has cancer, e.g., a T cell malignancy such as cutaneous T cell leukemia and myeloma. In another embodiment, the subject has a chronic infection, e.g., HIV infection, HCV infection, HBV infection and TB infection.

In another embodiment, the fusion molecule is administered near the location of a tumor.

In another embodiment, the method involves administering the subject a vaccine near the location of the administration of the fusion molecule.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1. In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In another aspect, the invention provides a method of modulating the suppressive effect of CD4+CD25+ regulatory T cells of T effector cells in a subject by administering to the subject a fusion molecule comprising a chemokine receptor ligand and a toxin moiety, thereby inhibiting immune suppression in the subject.

In one embodiment, the subject has cancer, e.g., a T cell malignancy such as cutaneous T cell leukemia and myeloma. In another embodiment, the subject has a chronic infection, e.g., HIV infection, HCV infection, HBV infection and TB infection.

In another embodiment, the fusion molecule is administered near the location of a tumor.

In another embodiment, the method involves administering the subject a vaccine near the location of the administration of the fusion molecule.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1. In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In another aspect, the invention provides a method of treating a subject having a chronic infection by administering to the subject a fusion molecule comprising a chemokine receptor ligand and a toxin moiety, thereby treating the chronic infection in the subject.

In one embodiment, the chronic infection is a bacterial infection, e.g., tuberculosis infection. In another embodiment, the infection is a viral infection, e.g., HIV infection, HCV infection, HBV infection. In another embodiment, the infection is a fungal infection.

In one embodiment, the fusion molecule is administered locally.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1. In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In one embodiment, the invention provides a method of treating a subject having cancer by administering to the subject a fusion molecule comprising a chemokine receptor ligand and a toxin moiety, thereby inhibiting immune suppression in the subject.

In a related embodiment the cancer is a T cell malignancy, e.g., cutaneous T cell leukemia or myeloma.

In one embodiment, the fusion molecule is administered near the location of a tumor.

In one embodiment, the fusion molecule is administered locally.

In another embodiment, the chemokine receptor ligand is selected from the group consisting of a chemokine and a chemoattractant. In a related embodiment, the chemokine receptor ligand is a chemokine, e.g., MC148, TARC/CCL17, I-309/CCL1, MDC/CCL22, and vMIP-1 In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or toxic fragment thereof, e.g., eosinophil-derived RNase (EDN), *Pseudomonas* exotoxin, diphtheria toxin, or anthrax toxin, or a fragment thereof. In another embodiment, the toxin moiety is a non-proteinaceous toxin, e.g., a maytansinoid, a calicheamicin or a taxane.

In specific embodiment, the fusion molecule is TARC-EDN, TARC-PE38, MC148-PE38 and MC148-EDN.

In another aspect, the invention provides a pharmaceutical composition comprising a fusion molecule comprising a chemokine receptor ligand and a toxin moiety and a pharmaceutically acceptable carrier.

In one embodiment, the chemokine receptor ligand is a chemokine or a chemoattractant. In one embodiment, the chemokine receptor ligand is a chemokine, e.g., MC148, TARC/CCL17, I-309/CCL1, MDC/CCL22, and vMIP-1 In a related embodiment, the chemokine receptor ligand is specific for a chemokine receptor selected from the group consisting of CCR8, CCR4, CXCR1 CXCR4, CXCR2, CXCR3, CXCR5, CXCR6, CCR1, CCR2, CCR3, CCR4, CCR5, CCR6, CCR7, CCR8, CCR9 and CCR10. In a specific embodiment, the chemokine receptor ligand is specific for a chemokine receptor selected from the group consisting of CCR8 and CCR4.

In another embodiment, the toxin moiety is a proteinaceous toxin, or fragment thereof, e.g., eosinophil-derived RNase, *Pseudomonas* exotoxin, diphtheria toxin, or anthrax toxin. In a related embodiment, the toxin moiety is a non-proteinaceous toxin, e.g., a maytansinoid, a calicheamicin or a taxane.

In one embodiment, the pharmaceutical composition is used for the treatment of a T cell malignancy, e.g., cutaneous T cell leukemia and myeloma.

In another embodiment, the pharmaceutical composition is used for the treatment of a chronic infection, e.g., HIV infection, HCV infection, HBV infection or TB infection.

DESCRIPTION OF THE DRAWINGS

FIGS. 1A-G are schematic representations of representative molecules of the invention. Genes for the mature form of viral chemokine MC148, or human TARC, or its mutant non-active form MC148D were fused in frame with various RNase moieties, such as EDN (MC148-EDN, TARC-EDN and MC148D-EDN, respectively), or ANG (TARC-ANG), or the toxin moiety, PE38 (TARC-PE38). Control constructs expressed chemokine fusions with the VL chain of mouse plasmacytoma MOPC315 (MC148-VL315) or with tumor antigen OFA (TARC-OFA), respectively. Representative constructs contained optional c-myc and His peptide tags to enable purification and detection (Tag), and an optional spacer peptide (SP) separating the chemokine from the antigen to enable proper folding of the protein.

FIGS. 2A-B depict graphs indicating that human T cell leukemia cells (CEM), but not MOLT cells express CCR4.

FIGS. 3A-B depict graphs indicating that human TARC-EDN binds to and is internalized by cells expressing CCR4. FIG. 3A depicts $10^5$ cells treated with 25 µg/ml of protein (Control, EDN, or human TARC-EDN) for 1 hour at 4° C. FIG. 3B depicts $10^5$ cells treated with 25 µg/ml of protein (Control, EDN, or human TARC-EDN) for 1 hour at 37° C.

FIG. 6A depicts the effects of human TARC-PE38 on the viability of CEM (CCR4+) and MOLT4 (CCR4−) cells. FIG. 6B depicts the effects of human TARC-PE38 and human TARC-OFA (control) on the vialibility of CEM (CCR4+) cells.

FIGS. 8A-E demonstrate that chemokine fusions retain properties of fused moieties. (A) Chemokines fused with EDN exhibit RNase activity (MC148-EDN and TARC-EDN) while MC148 fused to VL315 had no RNase activity. Shown, mean±SD, of the representative data from three independent experiments with similar results. (B) TARC-EDN induces chemotaxis of human monocytes. A chemotaxis assay was performed using microchemotaxis chambers as described in Materials and Methods. Data are plotted±SD; *, $P<0.01$ versus corresponding dose of EDN. (C) MC148-EDN binds to the receptor positive HEK293/CCR8, but not to the receptor negative parental HEK-293 cells. Cells were incubated in the medium containing either PBS (thin solid line), EDN (dashed line), or TARC-EDN (thick solid line) for 30 min at 4° C. (D) TARC-EDN (solid line) binds to CEM cells and down-regulates surface expression of CCR4. Controls for binding are PBS (interrupted line) and EDN (dotted line). Cells were incubated with 50 µg/ml proteins for 30 min at either 4° C. or 37° C. The protein binding was detected with rabbit polyclonal anti-EDN antibody, followed by FITC-conjugated anti-rabbit IgG antibody. Expression of CCR4 was detected with FITC-conjugated anti-human CCR4 antibody. Representative data from at least three independent experiments with similar results. (E) CEM cells internalize TARC-PE38 when incubated at 37° C., but not at 4° C. Cells were incubated with 25 µg/ml of TARC-PE38 for 1 hour and stained with anti c-myc antibody (9E10) and FITC-conjugated secondary antibody. Cells were visualized using fluorescence microscopy.

DETAILED DESCRIPTION OF THE INVENTION

Figure 4:
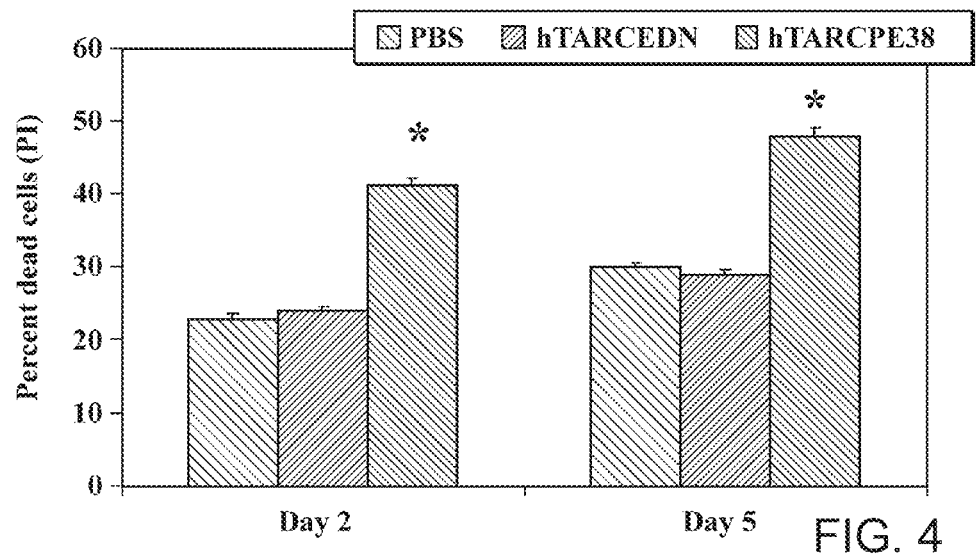
FIG. 4 depicts a graph indicating that fusion molecules of the invention preferentially kill T regulatory cells that express CCR4.

The instant invention is based, at least in part, on the discovery that fusion molecules comprising a chemokine fused to a toxin moiety, optionally including a linker, are capable of depleting T regulatory cells. These molecules are useful in the treatment of cancer, and autoimmunity, and further, can be used for efficient administration of a vaccine, e.g., a cancer vaccine. Moreover, the instant invention provides methods and compositions which allow one of skill in the art to use a chemokine to preferentially kill cells expressing chemokine receptor which binds the chemokine.

Accordingly, in one embodiment the invention provides methods of controlling immune response.

Molecules of the Invention

The present invention provides fusion molecules, e.g., molecules comprising a chemokine receptor ligand and one or more toxin moieties. The chemokine receptor ligand and the toxin moiety are optionally linked by a linker, e.g., a peptide or non-peptide linker.

Exemplary chemokine receptor ligands include MC148 (viral chemokine encoded by the poxvirus molluscum contagiosum), TARC/CCL17 (thymus and activation regulated chemokine), I-309/CCL1, MDC/CCL22, and vMIP-1 (HHV-8 produced viral chemokine). Alternatively, chemokine receptor ligands can be defined based on the receptor to which they bind. For example, chemokine receptor ligands used in the compositions and methods of the invention may bind to a chemokine receptor such as CCR8 and CCR4.

One of skill in the art can identify other chemokine receptor ligands and understands that homologues and orthologues of these molecules will be useful in the methods of the instant invention. Moreover, variants of the chemokine receptor ligands are useful in the methods of the invention.

The toxin moiety can be proteinaceous or non-proteinaceous. The term "non-proteinaceous" refers to toxin moieties that do not comprise protein or protein-like moieties. In other words, a non-proteinaceous toxin moiety is not peptide based and does not contain amino acids. Exemplary non-proteinaceous toxin moieties include maytansinoids (for example, in U.S. Pat. Nos. 5,208,020, 5,416,064 and European Patent EP 0 425 235 B 1), calicheamicins (for example, in U.S. Pat. Nos. 5,712,374, 5,714,586, 5,739,116, 5,767,285, 5,770,701, 5,770,710, 5,773,001, 5,877,296) or taxanes (such as paclitaxel and docetaxel).

The term "proteinaceous" as used herein refers to toxin moieties comprising protein or protein-like moieties. Thus, the term encompasses molecules that are naturally occurring proteins, fragments of naturally occurring protein toxins, and engineered polypeptides comprising naturally occurring amino acids, analogs of naturally occurring amino acids, and combinations thereof. Exemplary proteinaceous toxin moieties include eosinophil-derived RNase (EDN), *Pseudomonas* exotoxin, diphtheria toxin, or anthrax toxin, or a toxic fragment thereof.

The fusion molecules of the invention may be assembled post-translationally, i.e., the chemokine receptor ligand and the toxin moiety can be covalently liked after being synthesized, or expressed, separately. Alternatively, the chemokine receptor ligand and toxin moiety can be expressed as one transcript.

Nucleic Acid Molecules of the Invention

Another aspect of the invention pertains to vectors, preferably expression vectors, containing a nucleic acid molecule encoding the fusion molecules, or components thereof, of the invention. As used herein, the term "vector" refers to a nucleic acid molecule capable of transporting another nucleic acid molecule to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., fusion molecules comprising a chemokine receptor ligand and a toxin moiety).

The recombinant expression vectors of the invention can be designed for expression of the polypeptides of the invention in prokaryotic or eukaryotic cells. For example, the polypeptides can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari, et al., (1987) EMBO J 6:229-234), pMFa (Kudjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, the polypeptides can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J 8:729-733) and immunoglobulins (Banedji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Another aspect of the invention pertains to host cells into which a nucleic acid molecule encoding a polypeptide of the invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the polypeptide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the polypeptides of the invention. Accordingly, the invention further provides methods for producing polypeptides using the host cells of the invention. In one embodiment, the method comprises culturing the host cell of the invention (into which a recombinant expression vector encoding a polypeptide of the invention has been introduced) in a suitable medium such that a polypeptides of the invention is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which coding sequences have been introduced. Such host cells can then be used to create non-human transgenic animals in which exogenous sequences have been introduced into their genome or homologous recombinant animals in which endogenous sequences have been altered. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like.

Methods of Making the Molecules of the Invention

As described above, molecules of the invention may be made recombinantly using the nucleic acid molecules, vectors, and host cells described above.

Alternatively, the chemokine receptor ligand can be made synthetically, or isolated from a natural source and linked to the toxin moiety using methods and techniques well known to one of skill in the art.

Further, to increase the stability or half life of the fusion molecules of the invention, the peptides may be made, e.g., synthetically or recombinantly, to include one or more peptide analogs or mimmetics. Exemplary peptides can be synthesized to include D-isomers of the naturally occurring amino acid residues to increase the half life of the molecule when administered to a subject.

Pharmaceutical Compositions

The nucleic acid and polypeptide fusion molecules (also referred to herein as "active compounds") of the invention can be incorporated into pharmaceutical compositions. Such compositions typically include the nucleic acid molecule or protein, and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions of the instant invention may also include one or more other active compounds. Alternatively, the pharmaceutical compositions of the invention may be administered with one or more other active compounds. Other active compounds that can be administered with the pharmaceutical compounds of the invention, or formulated into the pharmaceutical compositions of the invention, include, for example, anticancer compounds, antiviral compounds, or antibacterial compounds.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Preferred pharmaceutical compositions of the invention are those that allow for local delivery of the active ingredient, e.g., delivery directly to the location of a tumor. Although systemic administration is useful in certain embodiments, local administration is preferred in most embodiments.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, kit or dispenser together with instructions, e.g., written instructions, for administration, particularly such instructions for use of the active agent to treat against a disorder or disease as disclosed herein, including an autoimmune disease or disorder, treatment in connection with an organ or tissue transplant, as well as other diseases or disorders with an autoimmune component such as AIDS. The container, pack, kit or dispenser may also contain, for example, a fusion molecule, a nucleic acid sequence encoding a fusion molecule, or a fusion molecule expressing cell.

Methods of Treatment

The compositions disclosed herein may be useful in the treatment of cancer, chronic infection, i.e., viral or bacterial infection, and in the administration of a vaccine to a subject.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The term "leukemia" includes malignancies of the hematopoietic cells of the bone marrow. Leukemias tend to proliferate as single cells. Examples of leukemias include acute myeloid leukemia (AML), acute promyelocytic leukemia, chronic myelogenous leukemia, mixed-lineage leukemia, acute monoblastic leukemia, acute lymphoblastic leukemia, acute non-lymphoblastic leukemia, blastic mantle cell leukemia, myelodyplastic syndrome, T cell leukemia, B cell leukemia, and chronic lymphocytic leukemia. Preferred leukemias include T cell malignancies, e.g., T cell leukemiz and myeloma.

The term "chronic infection" includes infections which may, for example, be bacterial infections (such as tuberculosis), parasitic infections such as malarial infections or viral infections (such as HPV, HCV, HBV or HIV infections).

Examples of chronic infections associated include human hepatitis viruses such as hepatitis A, B, C, D and E, for example hepatitis B virus (HBV) and hepatitis C virus (HCV) which cause chronic hepatitis, cirrhosis and liver cancer (see U.S. Pat. No. 5,738,852).

Additional examples of chronic infections caused by viral infectious agents include those caused by the human retroviruses: human immunodeficiency viruses (HIV-1 and HIV-2), which cause acquired immune deficiency syndrome (AIDS); and human T lymphotropic viruses (HTLV-1 and HTLV-2) which cause T cell leukemia and myelopathies. Many other infections such as human herpes viruses including the herpes simplex virus (HSV) types 1 and 2, Epstein Barr virus (EBV), cytomegalovirus (CMV), varicella-zoster virus (VZV) and human herpes virus 6 (HHV-6) are often not eradicated by host mechanisms, but rather become chronic and in this state may cause disease. Chronic infection with human papilloma viruses is associated with cervical carcinoma. Numerous other viruses and other infectious agents replicate intracellularly and may become chronic when host defense mechanisms fail to eliminate them. These include pathogenic protozoa (e.g., *Pneumocystis carinii, Trypanosoma, Leishmania, Plasmodium* (responsible for Malaria) and *Toxoplasma gondii*), bacteria (e.g., mycobacteria (eg *Mycobacterium tuberculosis* responsible for tuberculosis), salmonella and listeria), and fungi (e.g., *candida* and *aspergillus*).

The invention provides therapeutic methods and compositions for the prevention and treatment of cancer and chronic infection and for the administration of a vaccine to a subject. In particular, the invention provides methods and compositions for the prevention and treatment of cancer and chronic infection in subjects as well as methods and compositions that allow for efficient administration of a vaccine in humans as well as other animals through the administration of fusion molecules comprising a chemokine and a toxin moiety.

In one embodiment, the present invention contemplates a method of treatment, comprising: a) providing, i.e., administering: i) a mammalian patient particularly human who has, or is at risk of developing, cancer or a chronic infection, ii) one or more fusion molecules of the invention.

The term "at risk for developing" is herein defined as individuals with familial incidence of, for example, cancer or chronic infection.

The present invention is also not limited by the degree of benefit achieved by the administration of the fusion molecule. For example, the present invention is not limited to circumstances where all symptoms are eliminated. In one embodiment, administering a fusion molecule reduces the number or severity of symptoms of cancer or a chronic infection. In another embodiment, administering of a fusion molecule may delay the onset of symptoms.

As mentioned above, the indications for which the administration of fusion molecule compositions can be used include in particular cancer, e.g., T-cell related cancers, or chronic infection, e.g., HIV infection, HCV infection, HBV infection, TB infection.

Typical subjects for treatment in accordance with the individuals include mammals, such as primates, preferably humans. Cells treated in accordance with the invention also preferably are mammalian, particularly primate, especially human. As discussed above, a subject or cells are suitably identified as in needed of treatment, and the identified cells or subject are then selected for treatment and administered one or more of fusion molecules of the invention.

The treatment methods and compositions of the invention also will be useful for treatment of mammals other than humans, including for veterinary applications such as to treat horses and livestock e.g. cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

EXAMPLES

It should be appreciated that the invention should not be construed to be limited to the examples that are now described; rather, the invention should be construed to include any and all applications provided herein and all equivalent variations within the skill of the ordinary artisan.

Example 1

Materials and Methods

Fusion Gene Cloning and Plasmid Construction

Human and mouse TARC/CCL17 DNAs (mTARC and hTARC) were cloned from human and mouse thymus cDNA libraryby PCR truncated *Pseudomonas aeriginosa* DNA fragment, PE38, and EDN DNA fragment. mTARC and hTARC or viral MC148 chemokines were genetically fused in frame with toxin moieties (EDN or PE38), or with irrelevant tumor antigen OFA. Some constructs contained 6 His (SEQ ID NO: 25) and c-myc tag at COO-end for protein purification and analytical purposes. Chemokines were linked with toxin moieties via flexible linker peptide sequence (SP). All constructs were verified by DNA sequencing. The sequence of exemplary chemotoxin fusions consisting of a chemokine, or chemo-attractant fused in frame with toxic moiety, such as EDN or PE38 are set forth below.

The nucleic acid sequence of TARC-PE38 chemotoxin is set forth as SEQ ID NO:1.

```
                                              SEQ ID NO: 1
ATGGCACGAGGGACCAACGTGGGCCGGGAGTGCTGCCTGGAGTACTTCAA

GGGAGCCATTCCCCTTAGAAAGCTGAAGACGTGGTACCAGACATCTGAGG

ACTGCTCCAGGGATGCCATCGTTTTTGTAACTGTGCAGGGCAGGGCCATC

TGTTCGGACCCCAACAACAAGAGAGTGAAGAATGCAGTTAAATACCTGCA

AAGCCTTGAGAGGTCTGATGGTGGTGGCTCTGGCGGTGGGGGTAGCCTCG

AGGGTGGTGGTGGTTCTAAACCGCCGCAGTTCACTTGGGCTCAGTGGTTC

GAAACTCAGCATATCAACATGACTTCTCAGCAGTGCACTAACGCTATGCA

GGTTATCAACAACTACCAGCGTCGTTGCAAAAACCAGAACACTTTCCTGC

TGACTACTTTCGCTAACGTTGTTAACGTTTGCGGTAACCCGAACATGACT

TGCCCGTCTAACAAAACTCGTAAAAACTGCCATCATTCTGGTTCTCAGGT

TCCGCTGATCCATTGCAACCTGACTACTCCGTCTCCGCAGAACATCTCTA

ACTGCCGTTACGCTCAGACTCCGGCTAACATGTTCTACATCGTTGCTTGC

GACAACCGTGACCAGCGTCGTGACCCGCCGCAGTACCCGGTTGTTCCGGT

TCATCTGGACCGTATCATCGGATCCGCAGAAGAACAGAAACTGATCTCAG

AAGAGGATCTGGCCCACCACCATCACCATCACTAA
```

The Amino acid sequence of TARC-PE38 chemotoxin is set forth as SEQ ID NO:2. SEQ ID NO:2 is encoded by the nucleic acid molecule set forth as SEQ ID NO:1.

```
                                              SEQ ID NO: 2
MARGTNVGRECCLEYFKGAIPLRKLKTWYQTSEDCSRDAIVFVTVQGRAI

CSDPNNKRVKNAVKYLQSLERSDGGGSGGGGSLEGGGGSKPPQFTWAQWF

ETQHINMTSQQCTNAMQVINNYQRRCKNQNTFLLTTFANVVNVCGNPNMT

CPSNKTRKNCHHSGSQVPLIHCNLTTPSPQNISNCRYAQTPANMFYIVAC

DNRDQRRDPPQYPVVPVHLDRIIGSAEEQKLISEEDLAHHHHHH
```

The nucleic acid sequence of TARC-PE38 chemotoxin is set forth as SEQ ID NO:3.

```
                                              SEQ ID NO: 3
ATGGCACGAGGGACCAACGTGGGCCGGGAGTGCTGCCTGGAGTACTTCAA

GGGAGCCATTCCCCTTAGAAAGCTGAAGACGTGGTACCAGACATCTGAGG

ACTGCTCCAGGGATGCCATCGTTTTTGTAACTGTGCAGGGCAGGGCCATC

TGTTCGGACCCCAACAACAAGAGAGTGAAGAATGCAGTTAAATACCTGCA

AAGCCTTGAGAGGTCTGATGGTGGTGGCTCTGGCGGTGGGGGTAGCCTCG

AAGCTTCTGGAGGTCCCGAGGGCGGCAGCCTGGCCGCGCTGACCGCGCAC

CAGGCTTGCCACCTGCCGCTGGAGACTTTCACCCGTCATCGCCAGCCGCG

CGGCTGGGAACAACTGGAGCAGTGCGGCTATCCGGTGCAGCGGCTGGTCG

CCCTCTACCTGGCGGCGCGGCTGTCGTGGAACCAGGTCGACCAGGTGATC

CGCAACGCCCTGGCCAGCCCCGGCAGCGGCGGCGACCTGGGCGAAGCGAT

CCGCGAGCAGCCGGAGCAAGCCCGTCTGGCCCTGACCCTGGCCGCCGCCG

AGAGCGAGCGCTTCGTCCGGCAGGGCACCGGCAACGACGAGGCCGGCGCG

GCCAACGGCCCGGCGGACAGCGGCGACGCCCTGCTGGAGCGCAACTATCC

CACTGGCGCGGAGTTCCTCGGCGACGGCGGCGACGTCAGCTTCAGCACCC

GCGGCACGCAGAACTGGACGGTGGAGCGGCTGCTCCAGGCGCACCGCCAA

CTGGAGGAGCGCGGCTATGTGTTCGTCGGCTACCACGGCACCTTCCTCGA

AGCGGCGCAAAGCATCGTCTTCGGCGGGGTGCGCGCGCGCAGCCAGGACC

TCGACGCGATCTGGCGCGGTTTCTATATCGCCGGCGATCCGGCGCTGGCC

TACGGCTACGCCCAGGACCAGGAACCCGACGCACGCGGCCGGATCCGCAA

CGGTGCCCTGCTGCGGGTCTATGTGCCGCGCTCGAGCCTGCCGGGCTTCT

ACCGCACCAGCCTGACCCTGGCCGCGCCGGAGGCGGCGGGCGAGGTCGAA

CGGCTGATCGGCCATCCGCTGCCGCTGCGCCTGGACGCCATCACCGGCCC

CGAGGAGGAAGGCGGGCGCCTGGAGACCATTCTCGGCTGGCCGCTGGCCG

AGCGCACCGTGGTGATTCCCTCGGCGATCCCCACCGACCCGCGCAACGTC

GGCGGCGACCTCGACCCGTCCAGCATCCCCGACAAGGAACAGGCGATCAG

CGCCCTGCCGGACTACGCCAGCCAGCCCGGCAAACCGCCGCGCGAGGACC

TGAAGAGATCCGCAGAAGAACAGAAACTGATCTCAGAAGAGGATCTGGCC

CACCACCATCACCATCACTAA
```

Amino acid sequence of TARC-PE38 chemotoxin is set forth as SEQ ID NO:4. SEQ ID NO:4 is encoded by the nucleic acid molecule set forth as SEQ ID NO:3.

```
                                              SEQ ID NO: 4
MARGTNVGRECCLEYFKGAIPLRKLKTWYQTSEDCSRDAIVEVTVQGRAI

CSDPNNKRVKNAVKYLQSLERSDGGGSGGGGSLEASGGPEGGSLAALTAH

QACHLPLETFTRHRQPRGWEQLEQCGYPVQRLVALYLAARLSWNQVDQVI

RNALASPGSGGDLGEAIREQPEQARLALTLAAAESERFVRQGTGNDEAGA

ANGPADSGDALLERNYPTGAEFLGDGGDVSFSTRGTQNWTVERLLQAHRQ

LEERGYVFVGYHGTFLEAAQSIVFGGVRARSQDLDAIWRGFYIAGDPALA

YGYAQDQEPDARGRIRNGALLRVYVPRSSLPGFYRTSLTLAAPEAAGEVE

RLIGHPLPLRLDAITGPEEEGGRLETILGWPLAERTVVIPSAIPTDPRNV

GGDLDPSSIPDKEQAISALPDYASQPGKPPREDLKRSAEEQKLISEEDLA

HHHHHH
```

The nucleic acid sequence of I-309-EDN is set forth as SEQ ID NO:5.

```
                                              SEQ ID NO: 5
ATGGCATCCATGCAGGTACCGTTCTCCCGCTGTTGCTTCTCATTTGCGGA

GCAAGAGATTCCCCTGAGGGCAATCCTGTGTTACAGAAATACCAGCTCCA
```

```
TCTGCTCCAATGAGGGCTTAATATTCAAGCTGAAGAGAGGCAAAGAGGCC

TGCGCCTTGGACACAGTTGGATGGGTTCAGAGGCACAGAAAAATGCTGAG

GCACTGCCCGTCAAAAAGAAAATCCGGTGGTGGTGGTTCTGGCCTCGAGG

GTGGTGGTGGTTCTAAACCGCCGCAGTTCACTTGGGCTCAGTGGTTCGAA

ACTCAGCATATCAACATGACTTCTCAGCAGTGCACTAACGCTATGCAGGT

TATCAACAACTACCAGCGTCGTTGCAAAAACCAGAACACTTTCCTGCTGA

CTACTTTCGCTAACGTTGTTAACGTTTGCGGTAACCCGAACATGACTTGC

CCGTCTAACAAAACTCGTAAAAACTGCCATCATTCTGGTTCTCAGGTTCC

GCTGATCCATTGCAACCTGACTACTCCGTCTCCGCAGAACATCTCTAACT

GCCGTTACGCTCAGACTCCGGCTAACATGTTCTACATCGTTGCTTGCGAC

AACCGTGACCAGCGTCGTGACCCGCCGCAGTACCCGGTTGTTCCGGTTCA

TCTGGACCGTATCATCGGATCCGCAGAAGAACAGAAACTGATCTCAGAAG

AGGATCTGGCCCACCACCATCACCATCACTAA
```

The amino acid sequence of I-309-EDN is set forth as SEQ ID NO:6. SEQ ID NO:6 is encoded by the nucleic acid molecule set forth as SEQ ID NO:5.

```
                                        SEQ ID NO: 6
MASMQVPFSRCCFSFAEQEIPLRAILCYRNTSSICSNEGLIFKLKRGKEA

CALDTVGWVQRHRKMLRHCPSKRKSGGGGSGLEGGGGSKPPQFTWAQWFE

TQHINMTSQQCTNAMQVINNYQRRCKNQNTFLLTTFANVVNVCGNPNMTC

PSNKTRKNCHHSGSQVPLIHCNLTTPSPQNISNCRYAQTPANMFYIVACD

NRDQRRDPPQYPVVPVHLDRIIGSAEEQKLISEEDLAHHHHHH
```

The nucleic acid sequence of MC148-EDN is set forth as SEQ ID NO:7.

```
                                        SEQ ID NO: 7
ATGGCACTCGCGAGACGGAAATGTTGTTTGAATCCCACAAATCGTCCGAT

CCCGAATCCTTTACTGCAAGATCTATCACGCGTCGACTATCAGGCGATAG

GACATGACTGCGGACGGGAAGCTTTCAGAGTGACGCTGCAAGACGGAAGA

CAAGGCTGCGTTAGCGTTGGTAACAAGAGCTTACTAGACTGGCTTCGGGG

ACACAAGGATCTCTGCCCTCAGATATGGTCCGGGTGCGAGTCTCTGGAAT

TCAACGACGCTCAGGCGCCGAAGAGTCTCGAGGGTGGTGGTGGTTCTAAA

CCGCCGCAGTTCACTTGGGCTCAGTGGTTCGAAACTCAGCATATCAACAT

GACTTCTCAGCAGTGCACTAACGCTATGCAGGTTATCAACAACTACCAGC

GTCGTTGCAAAAACCAGAACACTTTCCTGCTGACTACTTTCGCTAACGTT

GTTAACGTTTGCGGTAACCCGAACATGACTTGCCCGTCTAACAAAACTCG

TAAAAACTGCCATCATTCTGGTTCTCAGGTTCCGCTGATCCATTGCAACC

TGACTACTCCGTCTCCGCAGAACATCTCTAACTGCCGTTACGCTCAGACT

CCGGCTAACATGTTCTACATCGTTGCTTGCGACAACCGTGACCAGCGTCG

TGACCCGCCGCAGTACCCGGTTGTTCCGGTTCATCTGGACCGTATCATCG

GATCCGCAGAAGAACAGAAACTGATCTCAGAAGAGGATCTGGCCCACCAC

CATCACCATCACTAA
```

The amino acid sequence of MC148-EDN is set forth as SEQ ID NO:8. SEQ ID NO:8 is encoded by the nucleic acid molecule set forth as SEQ ID NO:7.

```
                                        SEQ ID NO: 8
MALARRKCCLNPTNRPIPNPLLQDLSRVDYQAIGHDCGREAFRVTLQDGR

QGCVSVGNKSLLDWLRGHKDLCPQIWSGCESLEFNDAQAPKSLEGGGGSK

PPQFTWAQWFETQHINMTSQQCTNAMQVINNYQRRCKNQNTFLLTTFANV

VNVCGNPNMTCPSNKTRKNCHHSGSQVPLIHCNLTTPSPQNISNCRYAQT

PANMFYIVACDNRDQRRDPPQYPVVPVHLDRIIGSAEEQKLISEEDLAHH

HHHH
```

The nucleic acid sequence of MC148-PE38 is set forth as SEQ ID NO:9.

```
                                        SEQ ID NO: 9
ATGGCACTCGCGAGACGGAAATGTTGTTTGAATCCCACAAATCGTCCGAT

CCCGAATCCTTTACTGCAAGATCTATCACGCGTCGACTATCAGGCGATAG

GACATGACTGCGGACGGGAAGCTTTCAGAGTGACGCTGCAAGACGGAAGA

CAAGGCTGCGTTAGCGTTGGTAACAAGAGCTTACTAGACTGGCTTCGGGG

ACACAAGGATCTCTGCCCTCAGATATGGTCCGGGTGCGAGTCTCTGGAAT

TCAACGACGCTCAGGCGCCGAAGAGTCTCGAAGCTTCTGGAGGTCCCGAG

GGCGGCAGCCTGGCCGCGCTGACCGCGCACCAGGCTTGCCACCTGCCGCT

GGAGACTTTCACCCGTCATCGCCAGCCGCGCGGCTGGGAACAACTGGAGC

AGTGCGGCTATCCGGTGCAGCGGCTGGTCGCCCTCTACCTGGCGGCGCGG

CTGTCGTGGAACCAGGTCGACCAGGTGATCCGCAACGCCCTGGCCAGCCC

CGGCAGCGGCGGCGACCTGGGCGAAGCGATCCGCGAGCAGCCGGAGCAAG

CCCGTCTGGCCCTGACCCTGGCCGCCGCCGAGAGCGAGCGCTTCGTCCGG

CAGGGCACCGGCAACGACGAGGCCGGCGCGGCCAACGGCCCGGCGGACAG

GCGCGACGCCCTGCTGGAGCGCAACTATCCCACTGGCGCGGAGTTCCTCG

GCGACGGCGGCGACGTCAGCTTCAGCACCCGCGGCACGCAGAACTGGACG

GTGGAGCGGCTGCTCCAGGCGCACCGCCAACTGGAGGAGCGCGGCTATGT

GTTCGTCGGCTACCACGGCACCTTCCTCGAAGCGGCGCAAAGCATCGTCT

TCGGCGGGGTGCGCGCGCGCAGCCAGGACCTCGACGCGATCTGGCGCGGT

TTCTATATCGCCGGCGATCCGGCGCTGGCCTACGGCTACGCCCAGGACCA

GGAACCCGACGCACGCGGCCGGATCCGCAACGGTGCCCTGCTGCGGGTCT

ATGTGCCGCGCTCGAGCCTGCCGGGCTTCTACCGCACCAGCCTGACCCTG

GCCGCGCCGGAGGCGGCGGGCGAGGTCGAACGGCTGATCGGCCATCCGCT

GCCGCTGCGCCTGGACGCCATCACCGGCCCCGAGGAGGAAGGCGGGCGCC

TGGAGACCATTCTCGGCTGGCCGCTGGCCGAGCGCACCGTGGTGATTCCC

TCGGCGATCCCCACCGACCCGCGCAACGTCGGCGGCGACCTCGACCCGTC

CAGCATCCCCGACAAGGAACAGGCGATCAGCGCCCTGCCGGACTACGCCA

GCCAGCCCGGCAAACCGCCGCGCGAGGACCTGAAGAGATCCGCAGAAGAA

CAGAAACTGATCTCAGAAGAGGATCTGGCCCACCACCATCACCATCACTAA
```

The amino acid sequence of MC148-PE38 is set forth as SEQ ID NO:10. SEQ ID NO:10 is encoded by the nucleic acid molecule set forth as SEQ ID NO:9.

SEQ ID NO: 10
MALARRKCCLNPTNRPIPNPLLQDLSRVDYQAIGHDCGREAFRVTLQDGR

QGCVSVGNKSLLDWLRGHKDLCPQIWSGCESLEFNDAQAPKSLEASGGPE

GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

VERLLQAHRQLEERGYVFVGYHGTFLEAAQSIVFGGVRARSQDLDAIWRG

FYIAGDPALAYGYAQDQEPDARGRIRNGALLRVYVPRSSLPGFYRTSLTL

AAPEAAGEVERLIGHPLPLRLDAITGPEEEGGRLETILGWPLAERTVVIP

SAIPTDPRNVGGDLDPSSIPDKEQAISALPDYASQPGKPPREDLKRSAEE

QKLISEEDLAHHHHHH

Recombinant Fusion Proteins and Peptides

Fusion proteins were expressed in *E. coli* and purified from inclusion bodies with subsequent denaturation and refolding steps and affinity purifications using FPLC chromatography. The integrity and purity (>90%) of recombinant proteins were tested by SDS-PAGE under reducing conditions and Western blot hybridization with 9E10 anti-c-myc mAb or anti-EDN antibody.

Cell Lines and Animals

Acute T-lymphoblastic leukemia CEM and MOLT-4 cells were purchased from ATCC and were cultured in RPMI medium supplemented with 10% FBS. Cell viability was determined by Annexin/PI staining or WST reagent. Cell proliferation was determined by BrDU incorporation.

Animals and In Vivo Studies

NOD/SCID mice were purchased from Jackson (The Jackson Laboratory, Bar Harbor, Me.). All animals were housed at the National Institute of Aging animal facility, Baltimore, Md. Animal care was provided in accordance with the procedures outlined in a Guide for the Care and Use of Laboratory Animals. Six- to eight-weeks old female NOD/SCID mice were inoculated with 20 million CEM cells subcutaneously. Two weeks after tumor inoculation, proteins (25 µg) were injected into the established tumors.

Isolation of Human Peripheral Blood Mononuclear Cells (PBMC) and T Cell Subsets

PBMCs were isolated from blood of healthy donors by Ficol density gradient centrifugation. Human CD8+ and CD4+ T cells were isolated from PBMCs using corresponding kits from R&D. CD4+/CD25+/CD4+ cells (T regulatory cells) were isolated from human T cells using MACS kit from Miltenyi Biotec.

Chemokine Receptor Expression and Binding

The ligand binding-internalization assays were performed with CEM or MOLT-4 cells ($1 \times 10^6$) blocked with mouse serum in PBS containing 2% BSA. Fusion proteins (25 µg/ml) were incubated in complete RPMI medium for 1 h at 37° C. or at 4° C. To detect bound proteins, the cells were incubated with rabbit anti-EDN antibody or rabbit IgG, followed with α-rabbit IgG/FITC Ab incubation (Sigma) for 20 min each, and then fixed with 1% paraformaldehyde. The binding-internalization was assessed via flow cytometry on a FACScan (Becton Dickinson, Franklin Lakes, N.J.) using CellQuest software. For CCR4 expression, cells were incubated for 45 min with FITC-conjugated anti-human CCR4 antibody (R&D) or with isotype-matched mouse IgG2b/FITC (R&D).

Example 1

Chemokine Fusion Proteins Kill Tumor Cells

Chemokine fusion proteins have been constructed with following toxic moieties (i) EDN, a human pancreatic RNase, eosonophil-derived neurotoxin, a member of the pancreatic RNase superfamily, previously shown to be potent cytotoxins for tumor cells after antibody targeting; (ii) human angiogenin, a member of the ribonuclease (RNase); or (iii) a truncated form of *Pseudomonas* exotoxin (PE38). The chemokines utilized in the fusion constructs were selected based on their ability to target CCR4 (TARC/CCL17 and MDC/CCL22) and CCR8 (I-309/CCL1, vMIP-I and MC148). Thus, chemotoxin proteins (MC148-EDN, mMIP3α-EDN, TARC-EDN and TARC-PE38) or control EDN fusion with mutant MC148 (MC148D-EDN), which can not bind CCR8, or TARC fused with tumor antigen OFA-iLRP (TARC-OFA) were constructed and produced at a high degree of purity (>95%). Angiogenin was excluded from further considerations due to its non-specific killing activity. Chemokine fusion did not affect RNase activity of EDN or function of PE38. Importantly, EDN or PE38 containing chemotoxins were able to kill only cells expressing a respective chemokine receptor, such as MC148-chemotoxins and TARC-chemotoxins killed cells via binding CCR8 or CCR4, respectively. Control cells that did not express CCR8 or CCR4 were not affected by treatment with MC148- or TARC-chemotoxins. PE38 containing chemotoxins were more potent than EDN ones, which required at least 5-7 days for optimal killing. PE38-based chemotoxins, particularly TARC-PE38, were able to efficiently kill human T lymphoblastoid CCRF-CEM cells (CEM) in vitro within 1-2 days of treatment ($IC_{50}$ of 3-8 nM). Moreover, s.c. established CEM tumors were killed by intratumoral injections of TARC-PE38 leaving only scar tissues at the site of injections. While mock treatment or TARC-OFA injections failed to protect mice, 100% of mice treated with TARC-PE38 survived and did not have palpable tumor during the observed period.

Schema of constructs are shown in FIG. 1. The data presented herein indicates that chemokines, such as MC148 (viral chemokine encoded by the poxvirus molluscum contagiosum) or thymus and activation-regulated chemokine (TARC), fused with a toxin moeity can specifically target and kill cells which express CCR8 and CCR4, respectively. The data demonstrate that MC148-EDN, or TARC-EDN, or TARC-PE38 chemotoxins, but not toxin alone, could bind to respective chemokine receptors, such as CCR8 and CCR4, respectively (FIG. 2 and FIG. 3).

Figure 5:
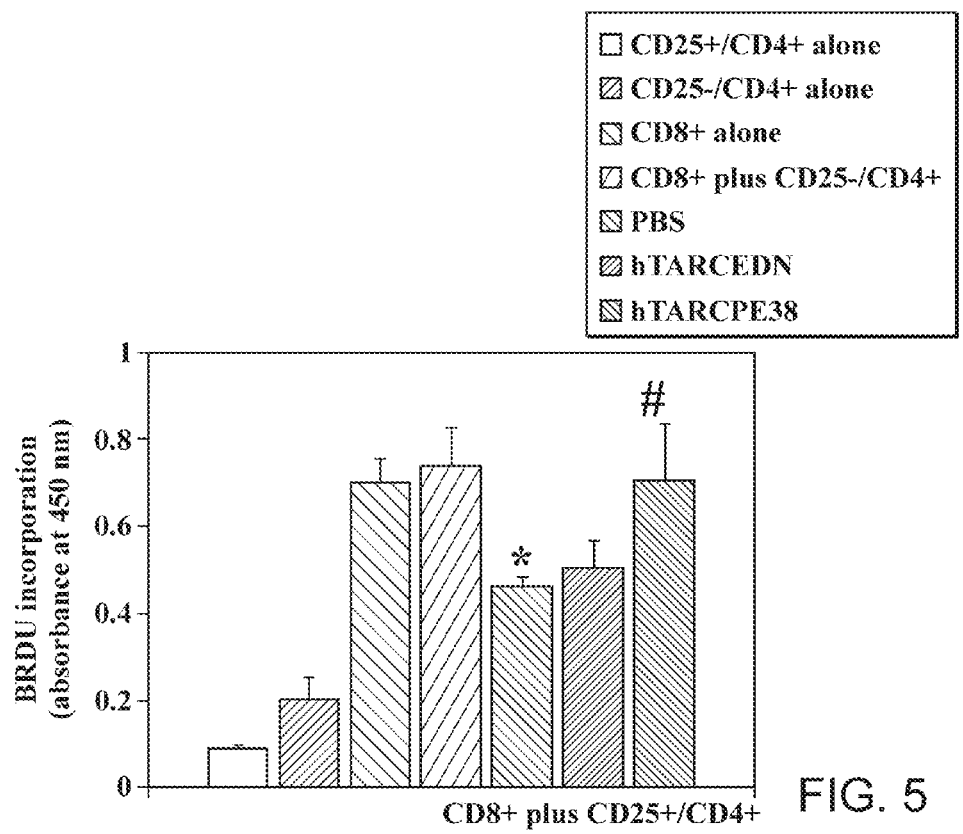
FIG. 5 depicts a graph indicating that the molecules of the invention revert suppressive effects of T regulatory cells on CD8+ T cells. The level of DNA synthesis was measured for CD8+ cells by BRDU incorporation. CD25+/CD4+ cells were treated with 1 µg/ml of the protein of the invention for 2 days, and then mixed with CD8+ cells. Cell proliferation was stimulated by the addition of 1 µg/ml anti-CD3 antibody for 3 days. The bars, from left to right, are: CD25+/CD4+ alone; CD25−/CD4+ alone; CD8+ alone; CD8+ and CD25+/CD4+; PBS; human TARC-EDN; human TARC-PE38.
Figure 6B:
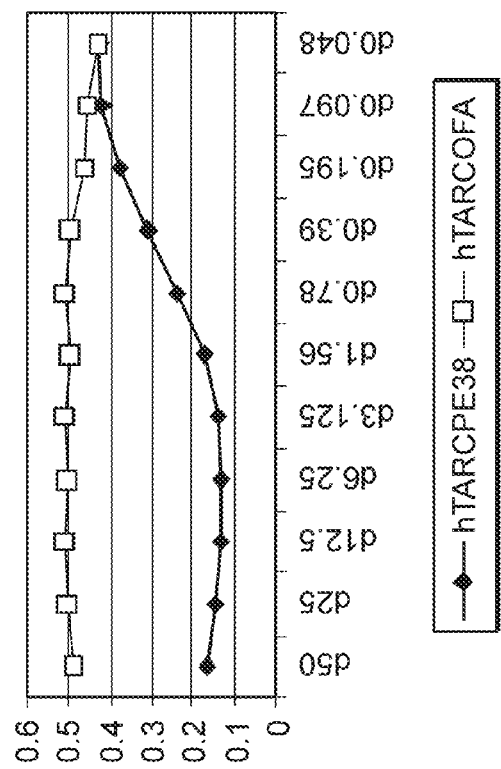
FIGS. 6A-B depict the effect of human TARC-PE38 on the vialibility of CEM and MOLT4 cells.
Figure 6A:
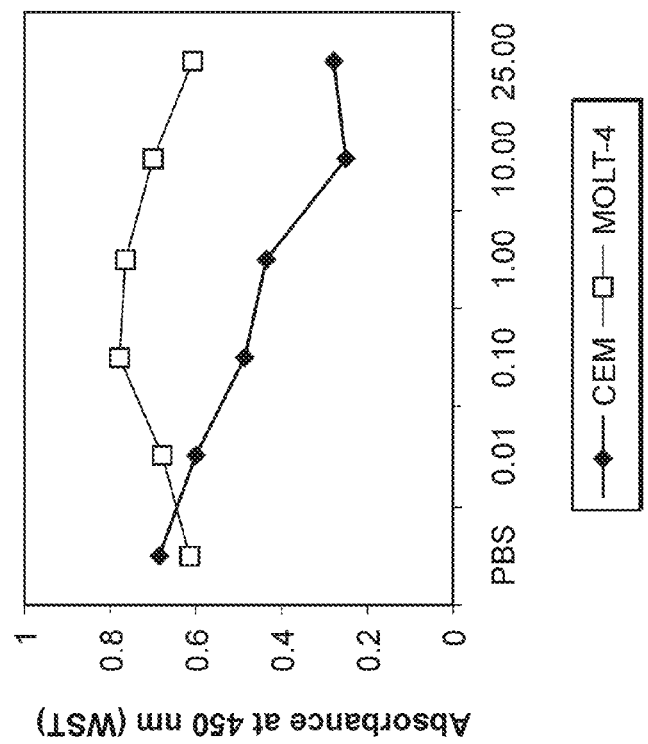

Treatment of CD4+ T cells with TARC-EDN or TARC-PE38 preferentially eliminated/killed CD4+/CD25+/CCR4+ cells (FIG. 4). This is a very specific process, since unlinked toxin alone (EDN) or control antigen fused with TARC failed to kill cells (FIG. 4 and FIG. 6). Reduction or elimination of Tregs correlated with enhanced proliferative responses of anti-CD3 stimulated CD8+ cells (FIG. 5). Moreover, chemotoxin treatment inhibited Treg-mediated suppression of CD8+ T cells (FIG. 5). Moreover, chemotoxin treatment drastically augmented T cell responses, such as mixed lymphocyte reaction.

Figure 7B:
FIGS. 7A-B depict the effect of human TARC-PE38 and human TARC-OFA on CEM(CCR4+) tumors in NOD-SCID mice 7 days after single injection of proteins. As is evident from the pictures, human TARC-PE38 significantly decreases the size of the tumor, whereas the control human TARC-OFA has no effect.
Figure 7A:

Moreover, chemotoxins efficiently killed CEM tumor cells both in vitro and in vivo in NOD-Scid mice (FIG. 6 and FIG. 7) suggesting that TARC-based chemotoxins might be utilized for the therapy of T-cell malignancies, such as cutaneous T-cell leukemia. Potency of chemotoxins is very high: only ng/ml quantities required to eliminate 50-80% cells (FIG. 6).

Example 2

Toxins Delivered Via Chemokine Receptors, Chemotoxins, Specifically Kill Tumor Cells Cell Lines and Mice.

Human acute T-lymphoblastic leukemia cell lines CCRF-CEM (CCL-119, CEM), and MOLT-4 (CRL-1582), and human embryonic kidney 293 cells (HEK-293) were purchased from ATCC (Manassas, Va.). HEK-293 cells stably transfected with human CCR8 (HEK/CCR8) were a gift from Dr. Zack Howard (Science Applications International Corporation, Frederick, Md.). HEK-293 cells were cultured in Dulbecco's modified Eagle's medium (Invitrogen Corporation, Carlsbad, Calif.) containing 10% fetal bovine serum (FBS). The same medium but with 400 µg/ml of G418 (Sigma-Aldrich, Inc., Saint Louis, Mo.) was used to maintain HEK/CCR8 cells. CEM and MOLT-4 cells were cultured in a standard RPMI medium 1640 (Invitrogen Corporation) supplemented with 10% FBS. Female 6-8 weeks old NOD/LtSz-scid/scid (NOD/SCID) mice were purchased from The Jackson Laboratory (Bar Harbor, Me.) and kept under pathogen-free conditions at the National Institute on Aging animal facility, Baltimore, Md. Animal care was provided in accordance with the procedures outlined in the Guide for the Care and Use of Laboratory Animals (NIH Publication No. 86-23, 1985).

Plasmid Constructs.

Schema of constructs is shown in FIG. 1. Mature sequence for TARC/CCL17 was cloned using RT/PCR from human thymus RNA using the following pairs of primers PRhTARCM-1 (ATCACCATG GCA CGA GGG ACC AAC GTG GGC CGG GAG T (SEQ ID NO:11)) and PRhTARC-GC-R3 (ATA CTC GAG GCT ACC CCC ACC GCC AGA GCC ACC ACC ACC AGA CCT CTC AAGGCTTTGCA-GGTA (SEQ ID NO:12)). Eosinophil-derived neurotoxin (EDN) was recloned using PCR with primers: PREDN-1 (ATA CTC GAG GGT GGT GGT GGT TCT AAA CCG CCG CAG TTC ACT TGG GCT(SEQ ID NO:13)) and PREDN-R2 (CGC GGA TCC GAT GAT ACG GTC CAG ATG AAC CGG AAC(SEQ ID NO:14)) from the EDN expressing plasmid described. Similarly, angiogenin (ANG) was PCR recloned from an ANG-expressing plasmid (Rybak S M et al. (1992) PNAS 89: 3165-3169) using primers PRAngi-1 (TATCATATGC TCGAGGGTGG CGGTG-GAAGC CAGGATAACT CCAGGTACAC ACACTTCCT (SEQ ID NO:15)) and PRAngi-R1 (ACTGGATCCC GGACGACGGA AAATTGACTGA (SEQ ID NO:16)). Bacterial expression vectors with CCR8 antagonist encoding mature sequence of MC148 (MC148) or mutant MC148 (MC148D, which could not bind CCR8 due to single a.a. residue replacement) of Molluscum contagiosum virus have been described previously 27. A truncated (38 kDa) form of Pseudomonas exotoxin (PE38) that does not have cell binding and internalization domain 28 was recloned from the pOND 21-2 plasmid (gift of Dr. Ira Pastan, NCI, Bethesda, Md.) using PCR with following primers: PRPE38-3 (ATAACCATG GAA GCT TCT GGA GGT CCC GAG GGC GGC AGC CTG GCC GCG CTGA(SEQ ID NO:17)) and PRPE38-R2 (TAT AGA TCT CTT CAG GTC CTC GCG CGG CGG TTT GCC GGG CTG GCT(SEQ ID NO:18)). To construct a chemotoxin expressing vector, PCR fragments encoding for mature sequence of human TARC were cut with NcoI and XhoI enzymes and ligated in frame with XhoI and BamHI cut fragments encoding for EDN (TARC-EDN) or ANG (TARC-ANG), and inserted into the bacterial expression plasmid pET11 opened with NcoI and BamHI (Novagen, Madison, Wis.) that was modified to contain also c-myc and six His tags (SEQ ID NO: 25). To construct EDN fusions with wild-type MC148 or mutant MC148D, XhoI and BamHI-cut END fragments were cloned into the XhoI and BamHI-opened pMC148-VL315 and pMC148D-VL315 plasmids. To construct chemotoxins with PE-38, PE38 fragment with Hind III (cut and blunted) and BglII ends were ligated into expression vectors for TARC or MC148 opened with XhoI (blunted) and BamHI (TARC-PE38 and MC148-PE38, respectively). The following control constructs were used: plasmids expressing MC148 or TARC fused with irrelevant tumor antigen like murine embryonic antigen OFA-iLRP (TARC-OFA) or plasmacytoma MOPC315-derived VL315 (MC148-VL315). A spacer fragment was inserted between chemoattractant and fusion moieties to enable proper folding of the protein. All constructs were verified by the DNA sequencing (Keck DNA Sequencing, Yale University, New Haven, Conn.).

Protein Production and Purification.

Chemotoxin plasmid—containing BL21 (DE3) E. coli cells (Stratagene, La Jolla, Calif.) were grown at 30° C. in 2×YT medium supplemented with 100 µg/ml each ampicillin and carbenicillin and 1% dextrose. Chemotoxin production was induced for 6 hours at 37° C. with 1 mM isopropyl-Beta-D-thiogalactopyranoside (IPTG) in the same growth medium except with 0.3% dextrose. Recombinant proteins were purified and refolded from bacterial inclusion bodies as described previously[30]. The integrity and purity of recombinant proteins were on average more than 90%, as tested by SDS-PAGE under reducing conditions and verified by Western blot hybridization with monoclonal 9E10 anti-c-myc antibody (Sigma) or with rabbit polyclonal anti-EDN antibody (use ref 41—you cannot buy this).

RNase Activity Assay.

RNase activity was determined at 37° C. by monitoring the formation of perchloric acid-soluble nucleotides as described (ref 41). Each assay was repeated twice and the data pooled.

Chemokine Receptor Binding-Internalization Assays.

Expression of CCR4 and CCR8 were tested using corresponding fluorescein isothiocyanate (FITC)-conjugated anti-human CCR4 and CCR8 antibodies (R&D systems) according to manufacturer instructions. The ligand binding-internalization assays were performed with $1 \times 10^5$ cells blocked with 10% mouse serum in PBS containing 2% bovine serum albumin (PBS-B). Proteins (50 µg/ml) were incubated in cell culture medium for 1 h at 37° C. or at 4° C., and, after extensive washings with PBS-B, incubated with either anti-c-myc monoclonal antibody (Ab) (1:100 dilution, 9E10) or anti-EDN polyclonal rabbit Ab (1:100 dilution). Then cells were incubated with respective secondary Abs conjugated with FITC, such as anti-mouse-IgG-FITC (Jackson ImmunoResearch Laboratory, Bar Harbor, Me.) and anti-rabbit IgG-FITC (Sigma) Abs. The binding/internalization was assessed by flow cytometry on a FACScan (Becton Dickinson, Franklin Lakes, N.J.) using CellQuest software. Alternatively, chemotoxin binding and internalization was assessed by fluorescent microscopy. Briefly, cells ($1 \times 10^5$) were treated for 1 hour at 37° C. or at 4° C. with 25 µg/ml fusion proteins in RPMI-1640 containing 10% fetal bovine serum (FBS). Then cells were fixed with 3.7% formaldehyde and permeabilized with 0.2% Triton X-100 (5 min) and incubated with mouse anti-c-myc Ab for 1 hour at 37° C., and for 30 min at 37° C. with goat anti-mouse IgG Ab conjugated to Alexa Fluor 488 (Molecular Probes Inc, OR, USA). Images were acquired with a 40× objective on an Axiovert 200 microscope (Carl Zeiss Vision GmbH, Munchen-Hallbergmoos, Germany) and using Axiovison software (Carl Zeiss Vision GmbH).

Chemotaxis Assay.

Human monocytes were isolated with the MACS CD14 monocyte isolation kit (Miltenyi Biotec, Auburn, Calif.) from Ficoll density gradient centrifuged peripheral blood mononuclear cells of healthy donors who provided signed informed consent. The purity was >95% as tested by flow cytometry. Chemotaxis was performed in AP48 microchemotaxis chamber (Neuro Probe, Cabin John, MD) following manufacturer's instructions.[31] Briefly, lower wells were filled with 25 µl complete RPMI medium containing titrated amounts of proteins or 1 ng/ml of N-Formyl-Met-Leu-Phe peptide (a positive control, FMLP, Sigma). The top chamber was filled with 50 µl ($1 \times 10^5$) cells. Chambers were separated with 5 µm pore size membrane. Cells were incubated for 90 minutes at 37° C. Non-migrated cells were gently removed and migrated cell were fixed and stained with haematoxylin/eosin and counted under 100× magnification in 3 randomly chosen fields. Results are expressed as number of cells per microscopic field and represent mean±SD of 3 wells.

Cell Viability Assays.

Cell viability was assessed using cell proliferation reagent WST-1 (Roche Applied Science, Indianapolis, Ind.). A minimum of three independent assays were performed in triplicate for each cell type and protein. Cells ($5 \times 10^4$), plated in 96-well flat-bottom plates one day prior to the assay, were treated with titrated amounts of proteins in complete RPMI medium supplemented with 1% FBS (for HEK-293 cells or HEK/CCR8 cells) or 10% FBS (for CEM and MOLT-4 cells) and cultured for up to 7 days. Then, cell media were replaced with 10% WST reagent and cell viability was assessed after 2-4 hours of incubation at 37° C. Results are expressed in percentage of $OD_{450}$ values of PBS-treated cells. For in vitro cell outgrowth assay, $1 \times 10^4$ CEM cells were plated in 96-well plate and treated with either PBS or 10 µg/ml of proteins and number of viable cells was evaluated daily for three days using WST reagent. Results are expressed in percentage of $OD_{450}$ values of PBS-treated cells. Cell apoptosis was tested by staining them with Annexin-V-Fluor Staining kit (Roche Applied Science) according to manufacturer instructions and analyzed by flow cytometry.

CEM Tumor Growth In Vivo.

Six- to eight-week-old female NOD/SCID mice were challenged subcutaneously with $2 \times 10^7$ CEM cells. Twelve days later, the mice were checked for the presence of palpable tumors and mice which did not develop tumors were excluded from the study. The remaining mice were randomized and intratumorally injected with 25 µg proteins in 100 µl PBS (TARC-PE38 or TARC-OFA) daily for five days. Tumor size was measured in perpendicular dimensions every other day and tumor surface area was calculated. Mice were euthanized at day 27 or when tumor area reached 400 mm² For histological analysis, tumor was fixed in 10% formalin and embedded in paraffin. Paraffin slides were stained with hematoxilin and eosin and analyzed with light microscopy. To study tumor outgrowth, tumor cells from PBS and chemotoxin-treated mice were isolated and cultured in vitro for 7 days. Then, these tumor-derived cells were seeded in 96-well plates ($5 \times 10^4$ cells/well) and treated for 2 days with TARC-PE38 or TARC-OFA, or PBS. Untreated parental CEM cells were used as control. Cell viability was assessed with WST reagent as described. Data were expressed as percentage of $OD_{450}$ values of control cells.

Efficacy of Systemic Therapy with Chemotoxin—

At Day 0, NOD/SCID mice were injected i.v. (tail vein) with $1 \times 10^6$ CEM cells (n=6). At Day 16 mice were bled and mononuclear cells were isolated and stained with anti-human CD45-FITC Ab (R&D systems) and were analyzed by FACS. CEM cells were detected in peripheral blood of all mice (data not shown). Starting from Day 20, 10 µg of TARC-PE38 or CTACK-PE38 (control chemotoxin) in 100 µl PBS were injected I.V. once a day for 4 days. In our in vitro killing assays CTACK-PE38 did not significantly reduce the viability of CEM cells at the doses up to 25 µg/ml (data not shown). At Day 25, mice were culled and spleens were removed. Some splenocytes were stained with anti-human CD45-FITC Ab and were analyzed by FACS to evaluate the percentage of spleen-infiltrating tumor cells. Ten million splenocytes were cultured in RPMI supplemented with 10% FBS for 10 days and, thereafter, were counted and analyzed for human CD45 and human CCR4 expression as markers of CEM cells.

Statistical Analysis.

All data are expressed as means±SD. Data were analyzed using a computer-based software system (StatView 5.0.1., SAS Institute Inc., Cary, N.C.). Differences were tested by analysis of variance followed by post hoc Scheffe's F-test.

Results

Chemokines Fused with Toxic Moieties Bind Respective Chemokine Receptors and are Internalized to the Cytosol.

Figure 8A:
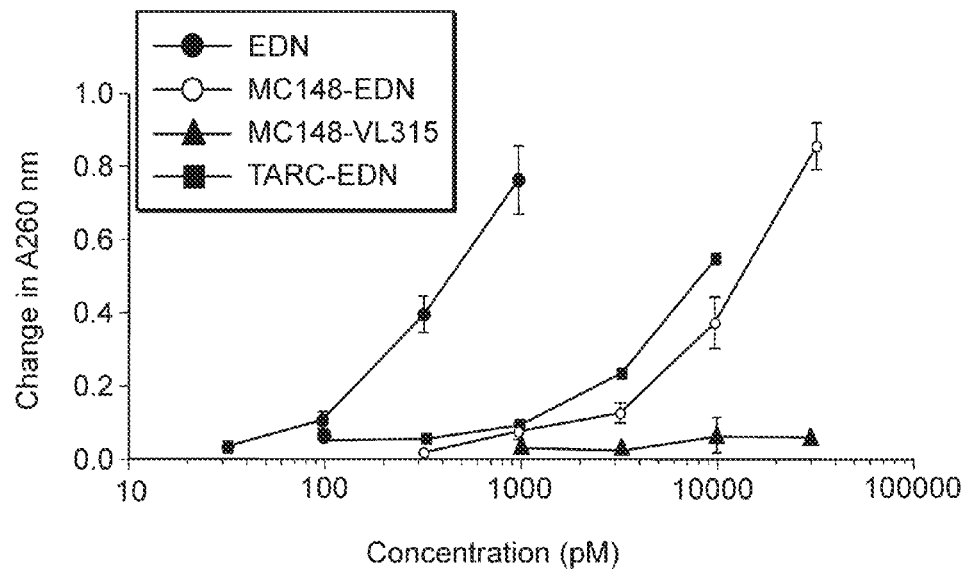
Figure 8B:
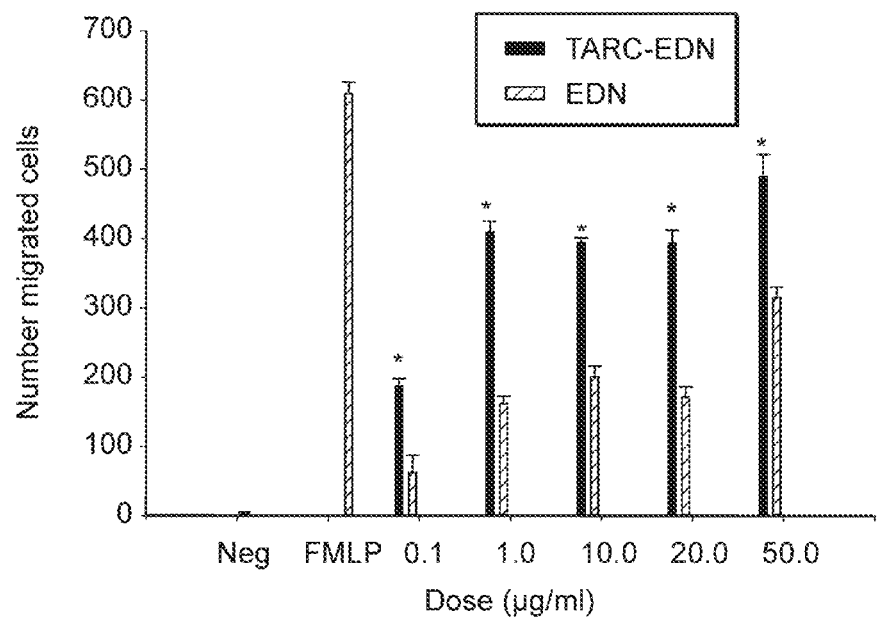
Figure 8C:
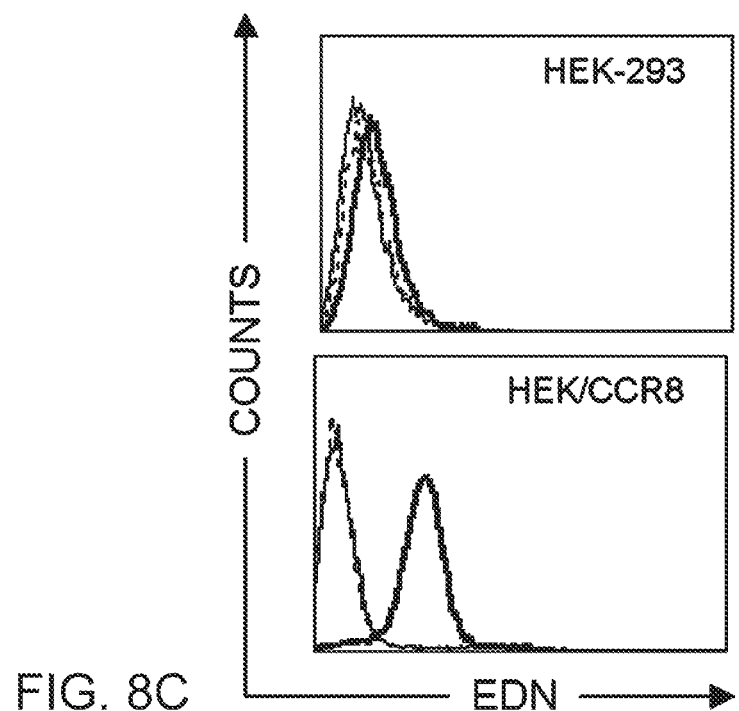
Figure 8D:
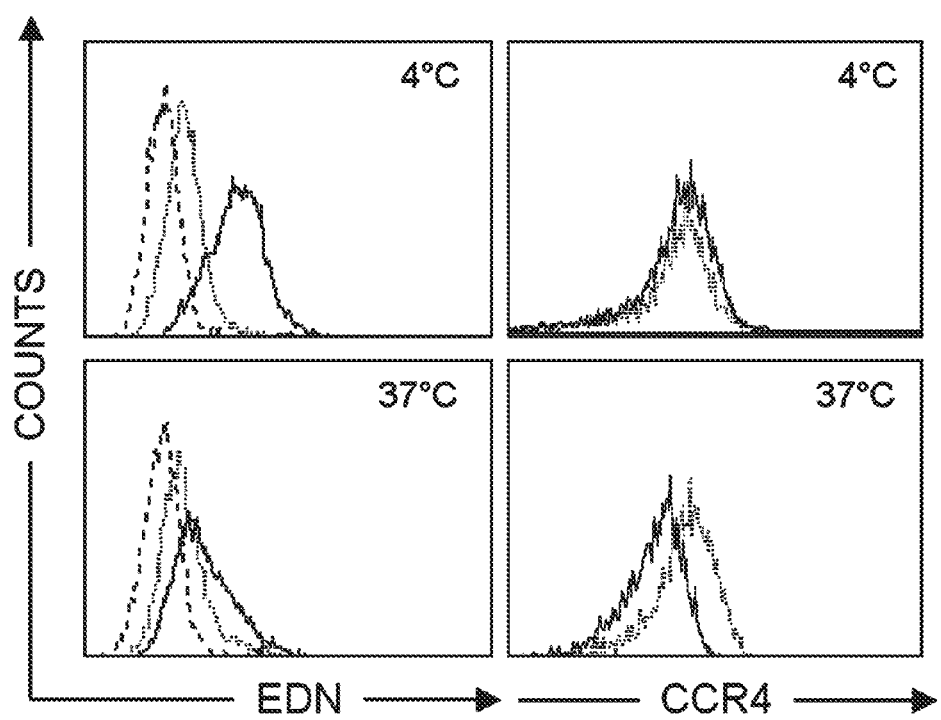

Chemokines MC148 and TARC/CCL17 were genetically fused with RNases, human eosinophilic RNase, EDN (MC148-EDN and TARC-EDN, respectively, FIG. 1) and human angiogenin (ANG, TARC-ANG, FIG. 1), or with a truncated form of *Pseudomonas* exotoxin PE38 (TARC-PE38, FIG. 1). The idea was that MC148- or TARC-chemotoxin would preferentially kill CCR8- and CCR4-expressing cells, respectively. Control constructs expressed MC148 or TARC fused with irrelevant non-toxic antigens, described previously (MC148-V1315 and TARC-OFA, FIG. 1). In addition, toxins were also fused with a mutant MC148 that lost ability to bind CCR8 (MC148D-EDN, FIG. 1). All proteins were in vitro refolded and purified to >95% purity from bacterial inclusion bodies as described in Biragyn, A., et al. ((1991). J. Immunol., 167: 6644-6653, 2001). Chemotoxins retained expected functional properties of the fused moieties. MC148-EDN and TARC-EDN (FIG. 8) and ANG (data not shown) exhibited significant RNase activity in vitro, though several fold less than unlinked RNases, while no RNase activity was exhibited by controls (MC148-VL315, FIG. 8A). Moreover, TARC-EDN was able to attract human monocytes in a dose-dependent manner (FIG. 8B), suggesting that chemotoxins also retained the ability to bind to their respective chemokine receptor(-s). Indeed, MC148- and TARC-chemotoxins could specifically bind CCR8- or CCR4-expressing HEK/CCR8 and CEM cells, respectively (FIGS. 8C,D), but not the receptor-negative control HEK-293 (FIG. 8C) and MOLT-4 cells (data not shown, and see FIG. 10A). Importantly, while TARC-chemotoxin was readily detected on the surface of CEM cells incubated at 4° C. (when internalization of ligand-bound receptors was sequestered), it was internalized within few minutes after incubation of cells at 37° C. (TARC-EDN, left panel, FIG. 8D) and found in the cell cytosol (TARC-PE38, right panel, FIG. 8E). The internalization was through a specific chemokine receptor as TARC-EDN down regulated surface expression of CCR4, when incubated at 37° C. (FIG. 8D), but not at 4° C. No CCR4 binding or modulation was detected in cells treated with EDN alone (FIG. 8D). Thus, chemotoxins retained functional properties of the fused moieties and were internalized to the cell cytosol utilizing their respective chemokine receptors.

Properties of RNase-Based Chemotoxins.

Figure 9A:
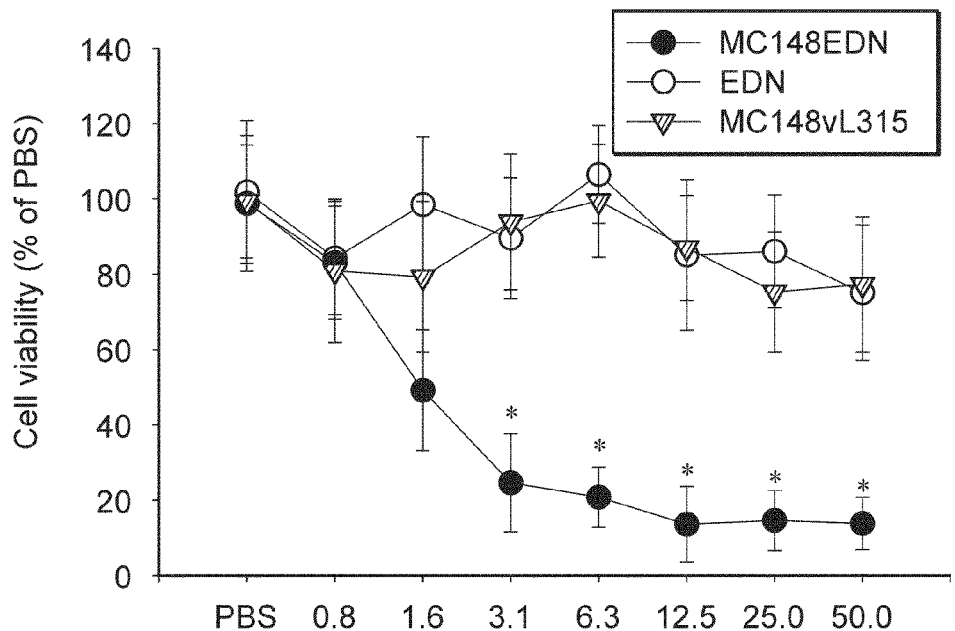
FIGS. 9A-D demonstrate that EDN fused with chemokines induces cell death. (A) Cytotoxicity of the MC148-EDN toward the CCR8 expressing HEK293/CCR8 cells after incubation for 7 days (chemotoxin amounts shown at µg/ml). Cell viability (Mean±SD) was measured using WST assay and results are presented in percentage from the values of the PBS-treated cells. * $P<0.05$ is for comparisons with the PBS group. (B) Killing of CCR4 expressing CEM cells with TARC-EDN incubated for 5 and 8 days with either 10 µg/ml TARC-EDN or EDN alone, or PBS. Cell death was evaluated by propidium iodide staining and flow cytometry analysis. P-value is for comparisons between the TARC-EDN and PBS groups. (C). Percent of apoptotic cells (annexin positive) (D) and dead cells (double positive for annexin and PI) after incubation with 10 µg/ml TARC-PE38 or TARC-OFA, or PBS for 1, 2 and 3 days.
Figure 9B:
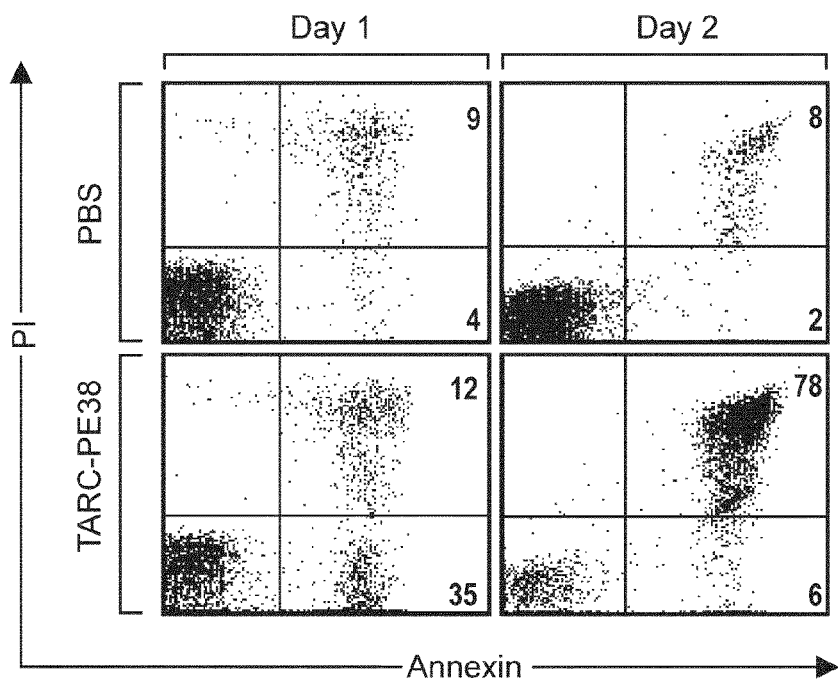

EDN-chemotoxin would presumably require a delivery to the cell cytosol or nucleus in order to be able to degrade cellular RNA and induce cell death. To test this, HEK/CCR8 cells were incubated with titrated amounts of MC148-EDN, or control proteins such as EDN alone and MC148-VL315. As shown in FIG. 9A, HEK/CCR8 cells were specifically killed only when incubated with MC148-EDN, but not with EDN alone or control MC148-VL315 protein. The cytotoxicity was specific to CCR8-expressing cells as MC148-EDN failed to kill CCR8-negative parental HEK-293 cells (data not shown). Similarly, EDN fused with another chemokine TARC (TARC-EDN), but not EDN alone, was also able to kill CCR4-expressing CEM cells (FIG. 9B). In contrast, TARC-ANG exhibited cytotoxicity, regardless of CCR4 expression (data not shown), thus this fusion was not studied further. Taken together, these data suggest that EDN was successfully rendered cytotoxic, if delivered to the cell cytosol as fusions with chemokines, presumably acting via degradation of intracellular RNA. However, despite the fact that relatively low concentrations of EDN-chemotoxin (30-100 μg/mL, FIG. 9C) induced cell death, it was only detectable after prolonged incubation 5-8 days (FIG. 9B).

Chemokine Receptor Expressing Tumor Cells are Selectively and Efficiently Killed by Chemotoxins In Vitro.

Figure 9C:
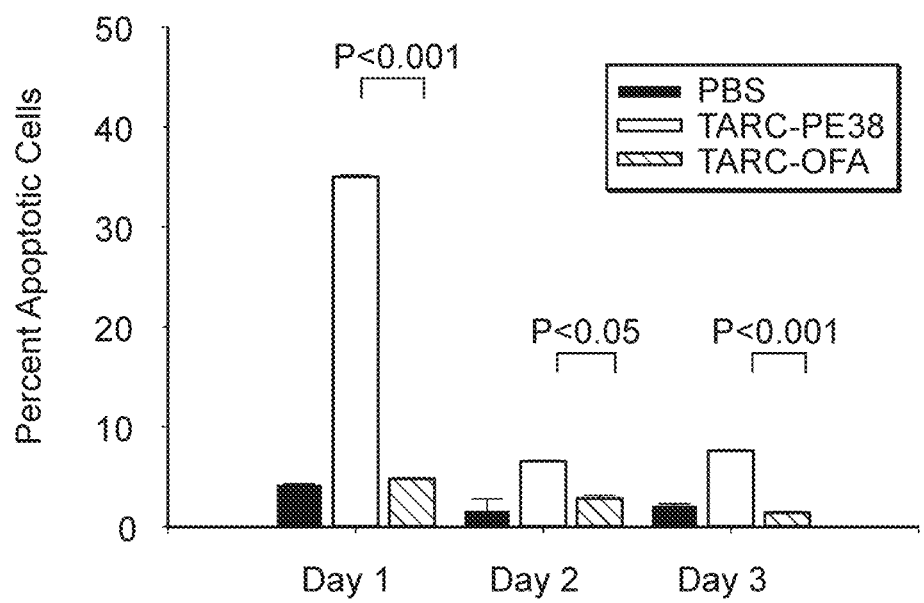
Figure 9D:
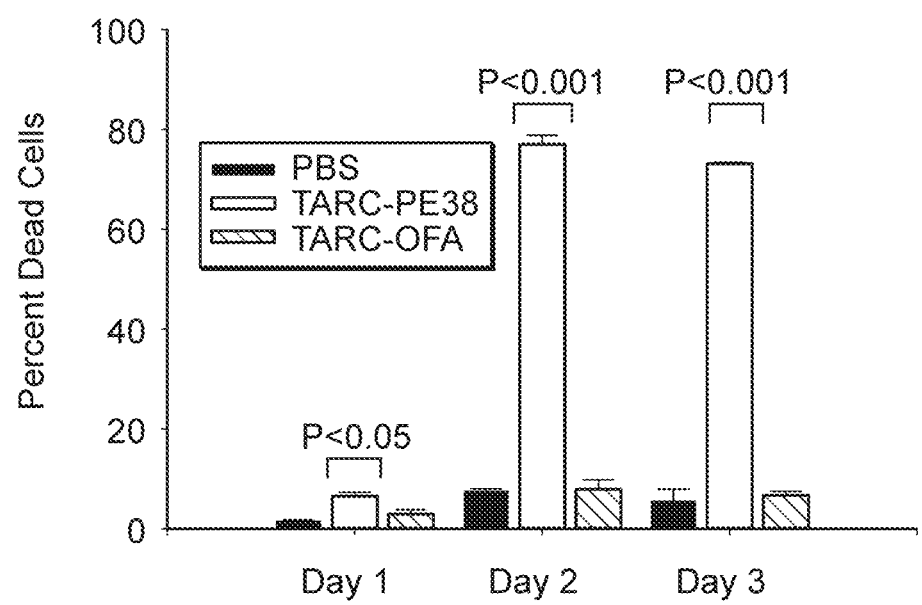
Figure 10A:
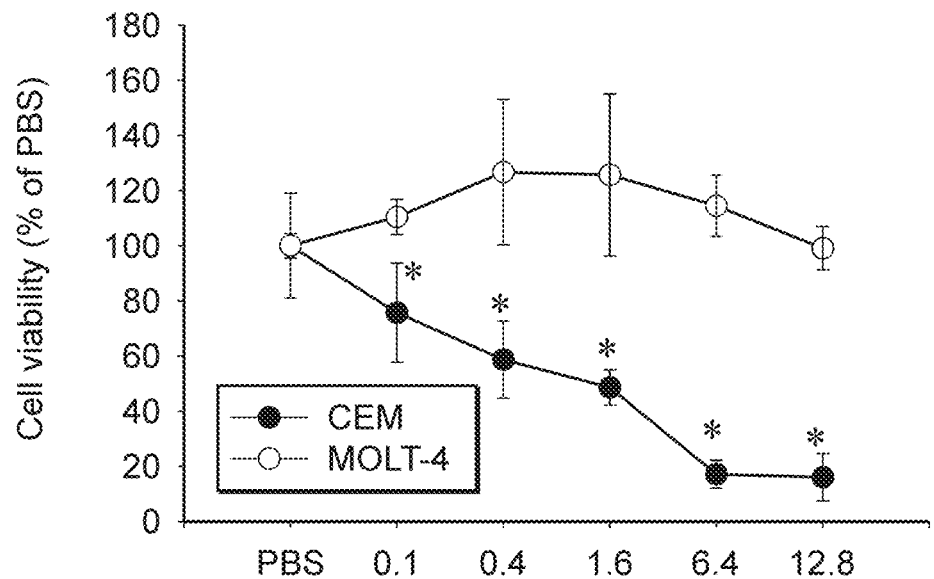
FIGS. 10A-C demonstrate the specificity of TARC-PE38 killing. (A) TARC-PE38 kills CCR4+ CEM cells and does not affect viability of CCR4− MOLT-4 cells. Cells were incubated with TARC-PE38 (shown in µg/ml) for two days and cell viability (mean±SD) was measured using WST assay. Results are presented as a percentage of the PBS-treated cells. * $P<0.05$ is for comparisons between CEM and MOLT-4 data at the indicated concentrations of TARC-PE38. (B) CEM cells are killed by only TARC-PE38, and not with TARC-OFA or TGFα-PE38. Protein concentrations shown are µg/ml. *, $P<0.05$ is for comparisons between the TARC-PE38 and TARC-OFA groups. (C) Kinetics of killing of CEM cells incubated with 10 µg/ml TARC-PE38, or controls (TARC-OFA, TARC-EDN, EDN and PBS) for 1-3 days. * $P<0.05$ is for comparisons between the TARC-PE38 and TARC-OFA groups. The viability was assessed using WST assay. PBS-treated cells at the corresponding time point. Representative data of at least three independent experiments with comparable data.
Figure 10B:
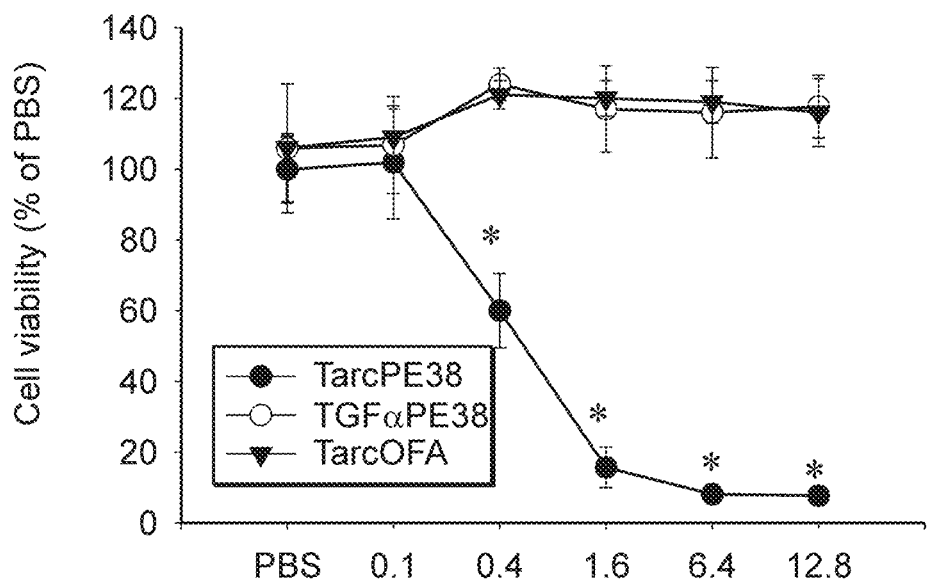
Figure 10C:
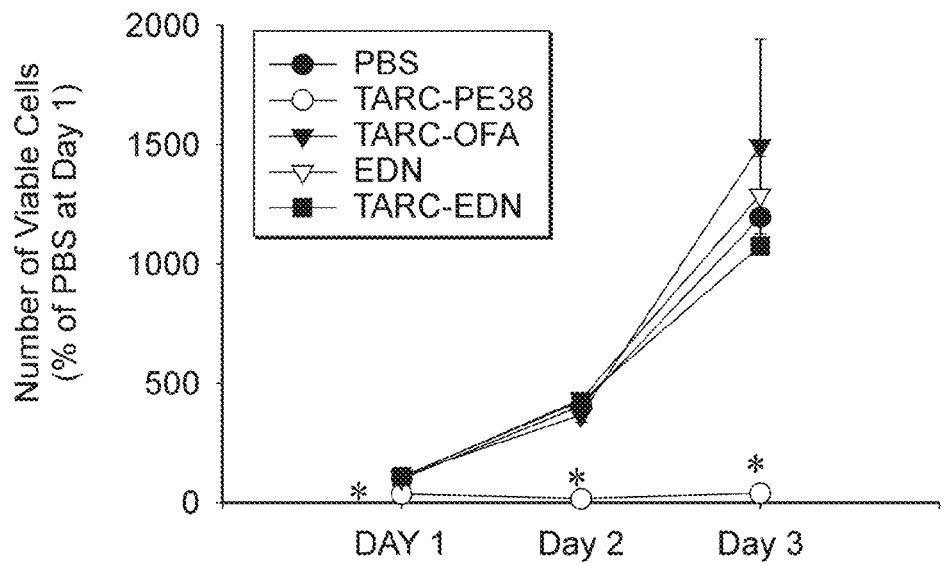

Bacterial toxins such as the exotoxin of *Pseudomonas aeruginosa* were reported to kill mammalian cells within a short period of time by inhibiting protein synthesis via the ADP-ribosylation of elongation initiation factor 2 (Allured, V. S., et al. (1986) Proc. Natl. Acad. Sci. U.S.A, 83: 1320-1324 and Li, M., et al (1995) Proc. Natl. Acad. Sci. U.S.A, 92: 9308-9312). Indeed, TARC-PE38 exhibited faster dynamics of cell killing than TARC-EDN. Overnight incubation with TARC-PE38 induced a marked increase in the apoptosis of CEM cells (FIGS. 9C and D), and after two days of incubation, resulted in 80% dead cells (FIGS. 9C and E). Similar to the EDN-based chemotoxins, TARC-PE38 also required CCR4, since it only killed CCR4-expressing CEM, and not CCR4-negative MOLT-4 cells (FIG. 10A). Control formulations TARC-OFA and TGFα-PE38 were not able to kill any cells, further supporting the requirement for chemokine receptor delivery to render PE38 cytotoxic (FIG. 10B). TARC-PE38 exhibited high potency as it induced significant killing at doses as low as 100 ng/ml (FIG. 10A), and a single overnight pretreatment with TARC-PE38 completely suppressed growth of fast growing CEM tumor cells in vitro (FIG. 10C). None of the controls used (TARC-OFA or EDN, FIG. 10) nor TARC-EDN affected the growth of CEM cells that multiplied 15-fold in three days.

TARC-PE38 Effectively Eradicates Established CCR4$^+$ Cutaneous Tumor in Mice.

Figure 11E:
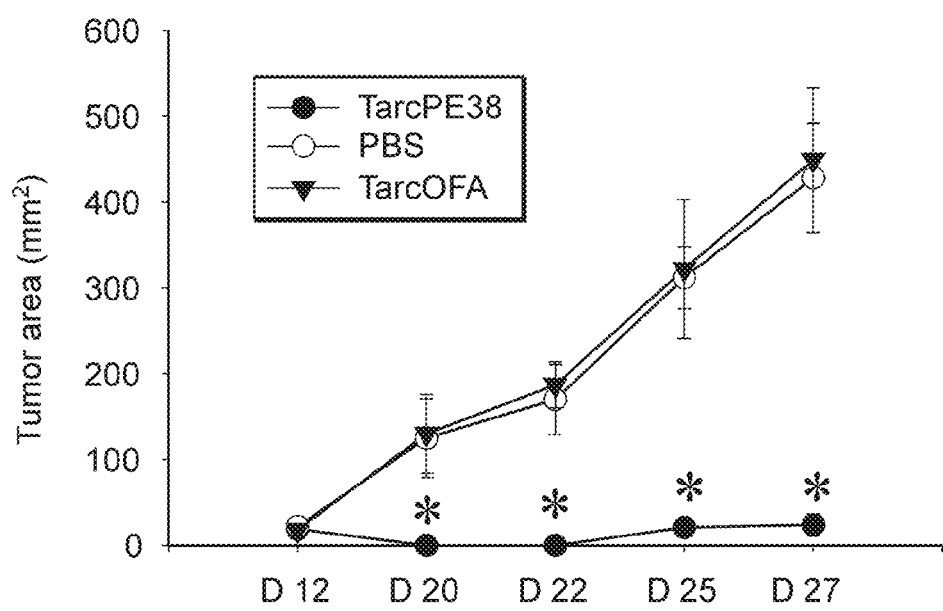
FIGS. 11A-E demonstrate that TARC-PE38 kills CEM tumor established in NOD-scid mice. Mice were mock treated (PBS) or intratumorally injected with 25 µg TARC-PE38 (B, D, E) or TARC-OFA (A, C, E) for 5 days starting from day 12 post tumor challenge. TARC-PE38 injections are associated with local necrosis (B) and disappearance of the palpable tumor mass (B) and tumor cells as evaluated after H&E stain at day 27 post tumor challenge (D, shown in 200× original magnification). (E) Tumor volume after treatments with TARC-PE38, or TARC-OFA or PBS. Tumors were established in NOD-SCID mice by subcutaneous injection of $2 \times 10^7$ CEM cells. * $P<0.05$ is for comparisons between the TARC-PE38 and TARC-OFA groups. Representative data from two independent experiments with comparable data with 8 mice per group.
Figure 11A:
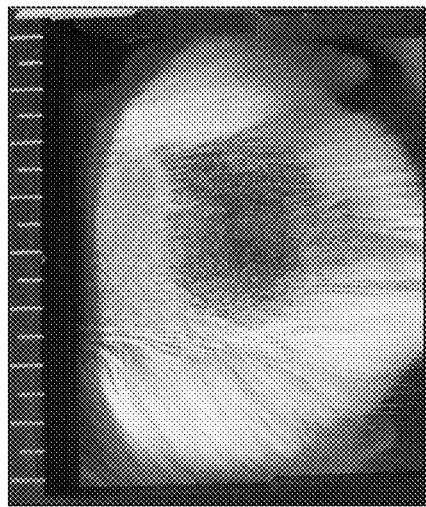
Figure 11B:
Figure 11C:
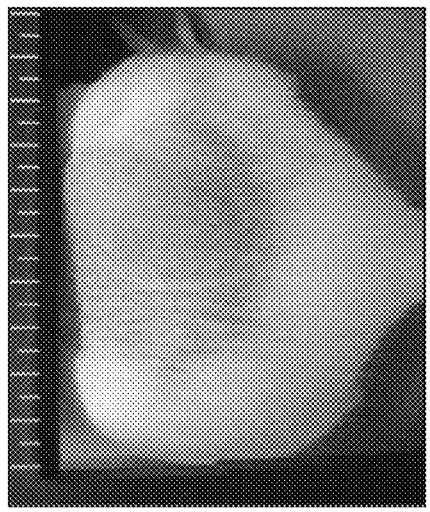
Figure 11D:
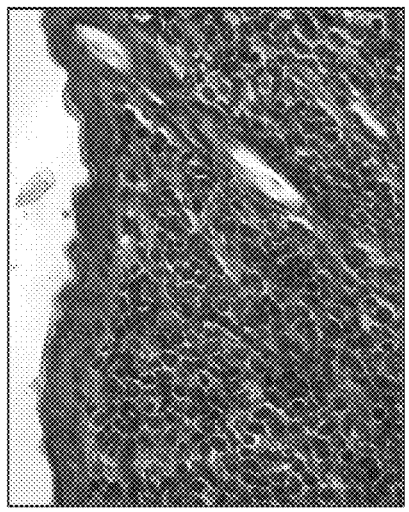

Patients with cutaneous T cell leukemia that express CCR4 have a poorer clinical outcome than CCR4$^-$ cutaneous T cell lymphomas. Due to the lack of murine models for cutaneous leukemia, we have established a subcutaneous human T-cell leukemia CEM model in NOD-SCID mice. Mice were injected in the flanks with CEM cells. At day 12 post-innoculation the tumor size reached 25-30 mm$^3$ Mice were injected intratumorally with PBS or 25 μg of TARC-PE38, or TARC-OFA once daily for five consecutive days Animals injected with PBS or the control TARC-OFA showed similar tumor growth and were sacrificed by day 27 when tumor size reached approximately 400 mm$^2$ (FIGS. 11A and 11E). In contrast, no measurable tumor was detected in mice treated with TARC-PE38, which was also associated with the appearance necrotic lesions at the tumor challenge site (FIGS. 5b and 5e). The data were supported by histological analysis taken at 27 day after tumor challenge. Samples from mice treated with TARC-OFA consisted primarily of tumor cells (cells with large and dense nuclei, FIG. 11C) infiltrated in the dermis and spread into subcutaneous tissue. In comparison the majority of the TARC-PE38 treated samples were free of tumor cells (FIG. 11D).

Tumor Relapse Due to Survival of Receptor-Negative Cells in NOD-SCID Mice.

Figure 12A:
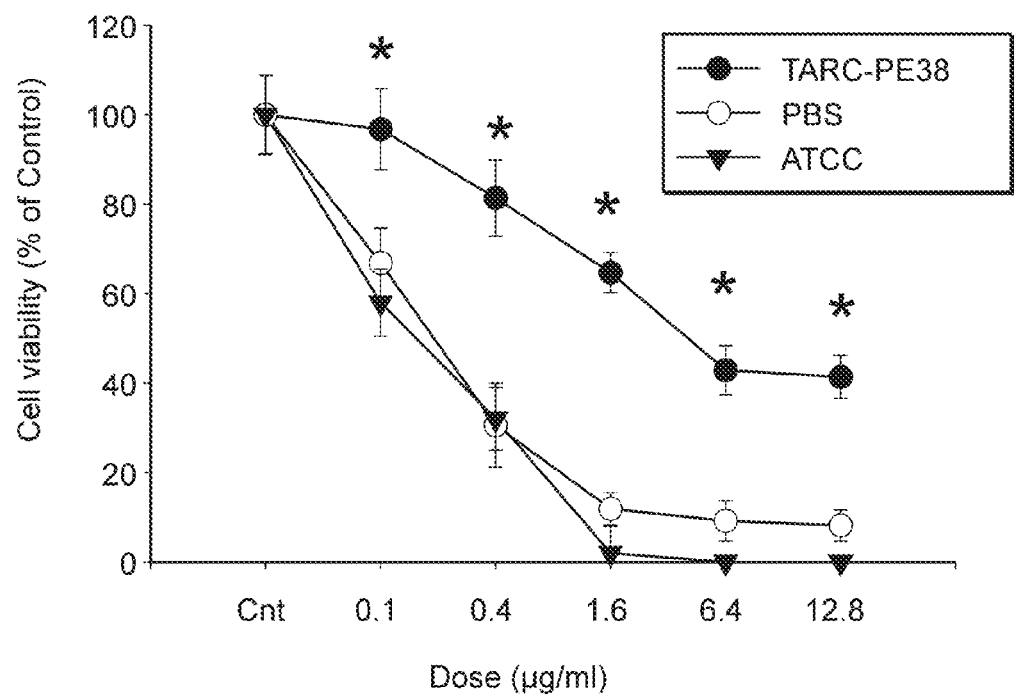
FIGS. 12A-D demonstrate the mechanism of tumor escape: TARC-PE38 kills selectively CCR4-positive tumors, but does not prevent outgrowth of resistant CCR4-negative escapees. Although TARC-PE38 injections eliminated any palpable signs of a tumor, tumor eventually grew back and did not respond to additional TARC-PE38 treatments. Tumor cells from PBS-treated animals (PBS) and relapsed tumor cells from TARC-PE38 treated animals (TARC-PE38) were cultured ex vivo in the presence of varying doses of TARC-PE38 (A). In parallel, parental CEM cells (ATCC) were also incubated with TARC-PE38. * $P<0.01$ is for comparisons with the TARC-PE38 treated parental CEM cells. To assess outgrowth of CCR4-negative CEM cells, parental CEM cells were treated with PBS, or 10 µg/ml TARC-OFA or TARC-PE-38 once (TARC-PE38 1×) or 5 times (TARC-OFA, TARC-PE38 5×) (B). Then cells were washed with PBS and culturing continued for several weeks more before staining for CCR4 expression (C) and (D) and testing for cell viability. * $P<0.01$ is for comparisons with the TARC-OFA treated group. Representative data from at least two independent experiments with comparable data.
Figure 12B:
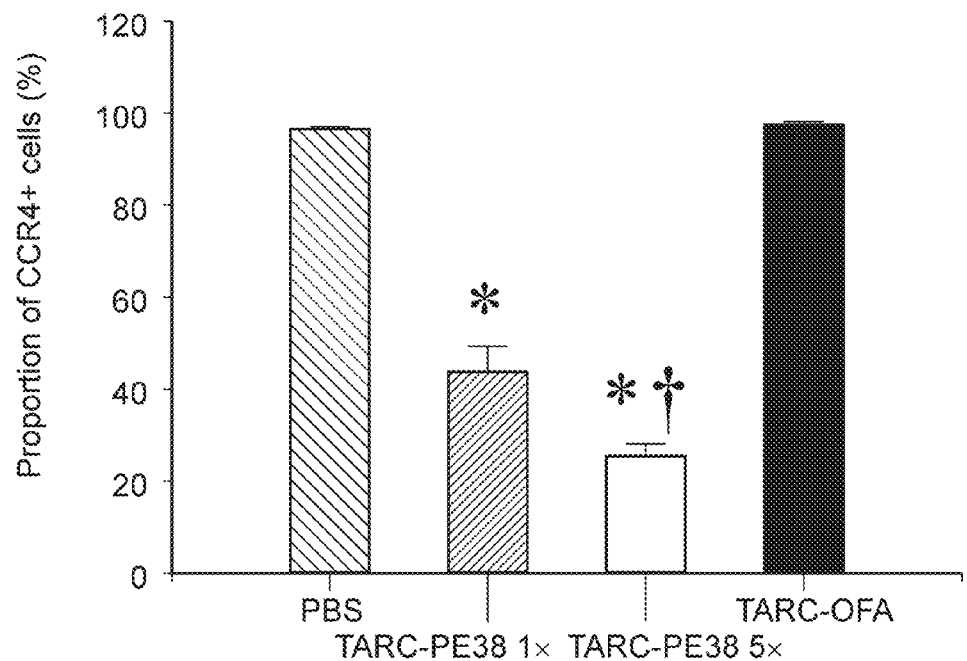
Figure 12D:
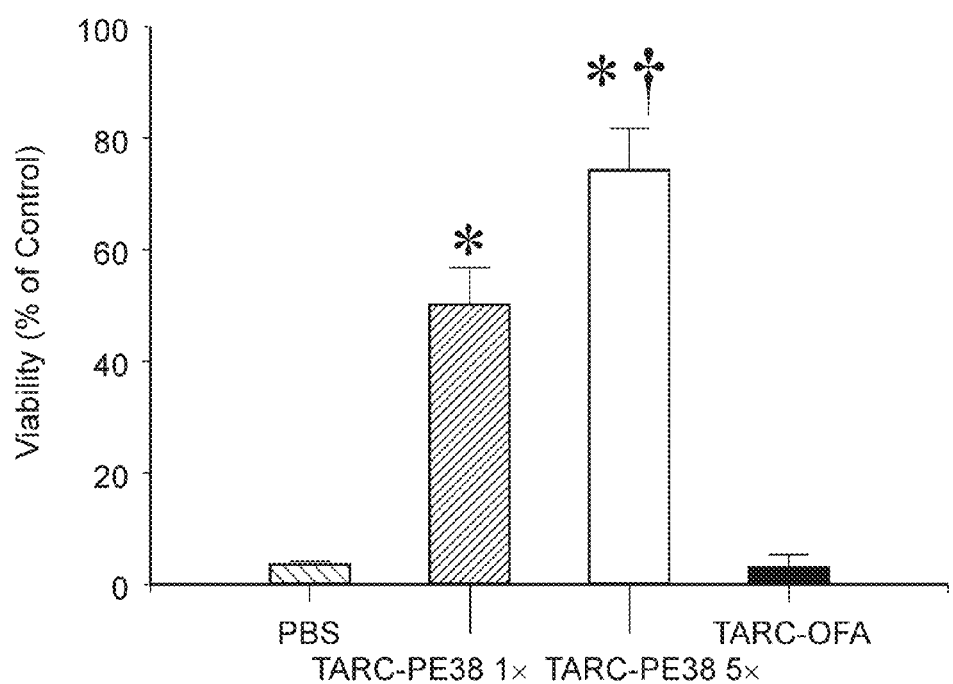
Figure 12C:
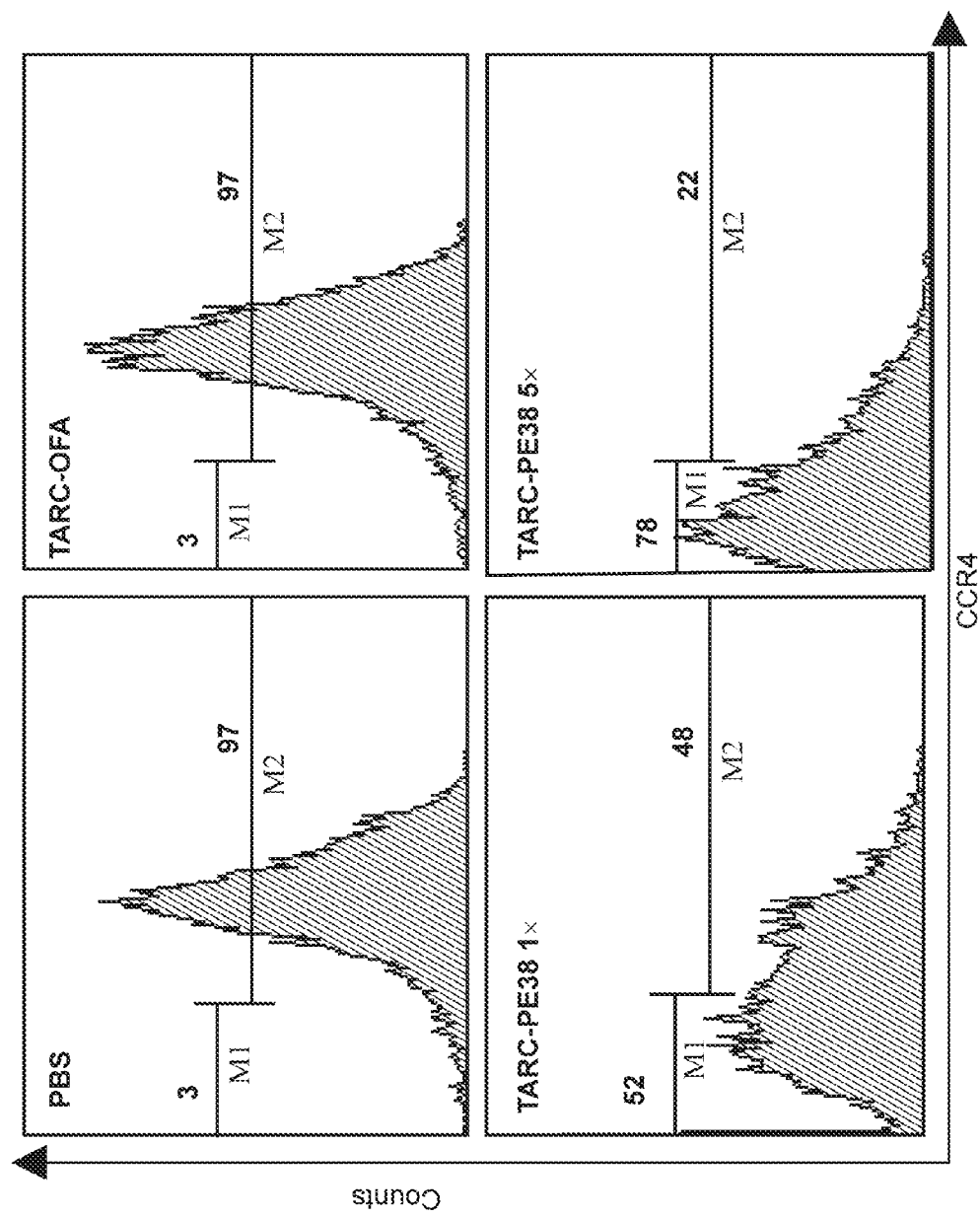

Despite the potency of the treatment and the fact that the TARC-PE38 treatment eliminated any palpable signs of tumors in mice, tumor eventually relapsed and tumor cells could be detected at the margins of the necrotic area and surrounding skin by day 27 after tumor challenge. Question—there is a disconnect here—how can you show tumor free histology and now take on the same samples and show tumor? However, the tumor cells had a different morphology than the initial tumor; cells were smaller in size with less dense nuclei as compared to the original or those from TARC-OFA-treated mice (data not shown). In addition, the tumor no longer responded to the TARC-PE38 treatment, and even higher doses and multiple injections of the chemotoxin could not affect tumor growth (data not shown). Therefore, we hypothesized that these tumors might represent an outgrowth of resistant cells that had lost expression of CCR4. To investigate, we cultured ex vivo cells removed from these relapsed tumors or from PBS treated mice. Cells were then treated in vitro with titrated doses of TARC-PE38 for two days. TARC-PE38 killed ex vivo grown tumor cells from the PBS-treated mice as efficiently as parental in vitro cultured CEM cells (FIG. 12A). In contrast, cells from the TARC-PE38 treated and relapsed tumors were significantly less affected by TARC-PE38 (survival significance of p<0.001, FIG. 12A), indicating that these cells were less sensitve to the TARC-PE38. To assess the mechanism of resistance, the parental in vitro cultured CEM cells were pretreated with PBS or 10 μg/ml of TARC-PE38, or TARC-OFA once or for five days every other day. As we described, a single pretreatment with TARC-PE38, but not with TARC-OFA or PBS, caused a dramatic cell death yielding few viable cells (less then 5%, data not shown). The remaining cells were then cultured in complete medium without chemotoxin for four weeks and analyzed for CCR4 expression. While the majority of the TARC-OFA- or PBS-treated cells expressed CCR4 (97%, FIGS. 12B and C), pretreatment with TARC-PE38 for a single time significantly reduced proportion of CCR4-expressing cells (48%, p<0.001, FIGS. 12B and C). Moreover, when cells were pretreated with TARC-PE38 five times and cultured for four weeks, the majority of cells were CCR4-negative (78%, FIGS. 12B and C). These cells not only became CCR4-negative, but also acquired resistance to subsequent treatments with TARC-PE38 (FIG. 12D). Control pretreatments with either PBS or TARC-OFA did not affect either the proportion of CCR4-expressing cells (FIGS. 12B and C), or sensitivity to TARC-PE38 (FIG. 12D). Overall, these data indicate that chemotoxin can be efficiently used for eradication of CCR4-positive cutaneous T cell tumors, that is often associated with a poorer disease outcome. However, it will not eliminate CCR4-negative tumor variants and, thus, may lead to tumor relapse of CCR4-negative escapees in immunosuppressed hosts (NOD-SCID mice).

Systemic Treatment with TARC-PE38 Depletes Spleen-Infiltrating Tumor Cells in Mice—

Figures 13A, 13B:
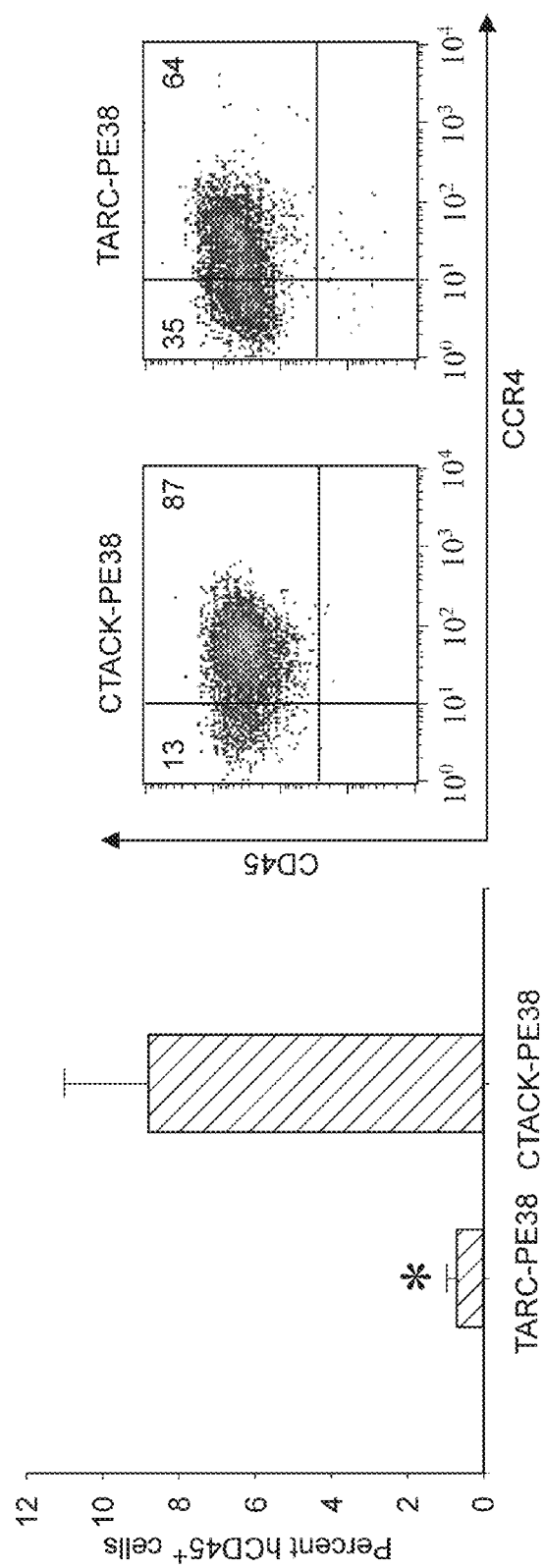
FIGS. 13 A-B demonstrate the efficacy of systemic therapy with chemotoxin. At Day 0, NOD/SCID mice were injected i.v. (tail vein) with $1 \times 10^6$ CEM cells (n=6). Starting from Day 20, 10 µg of TARC-PE38 or CTACK-PE38 (control chemotoxin) in 100 µl PBS were injected I.V. once a day for 4 days. At Day 25, mice were culled and spleens were removed. A. Some splenocytes were stained with anti-human CD45-FITC Ab and were analyzed by FACS to evaluate the percentage of spleen-infiltrating tumor cells. B. Ten million splenocytes were cultured in RPMI supplemented with 10% FBS for 10 days and, thereafter, were analyzed for human CD45 and human CCR4.

Systemic administration TARC-PE38 was also very effective for therapy of disseminated CEM cell growth in NOD/SCID mice (FIG. 13A). CEM cells express CD45 and in vitro cultured tumor cells were 100% positive for this marker (FIG. 13B). The percentage of human CD45-positive cells was dramatically reduced in mice treated with TARC-PE38 compared with that in control chemotoxin-treated mice (FIG. 13A). To confirm that cells-positive for human CD45 are indeed tumor cells, we cultured cells isolated from spleens for 10 days and evaluated cell number and expression of CEM cell markers. The number of cells expanded from spleens of TARC—PE38—treated mice was more than 20-fold less compared to those from CTACK—PE38— treated mice ($14.5\pm6.2\times10^6$ vs. $0.7\pm0.5\times10^6$, respectively, $P<0.05$). While 100% of expanded cells in both groups were CD45-positive, CCR4 expression in cells cultured from spleens of TARC-PE38—treated mice was about 3-fold higher compared to those from CTACK-PE38—treated mice ($35.2\pm6.2\%$ vs. $12.1\pm2.5\%$, respectively, $P<0.005$, and FIG. 13B).

Example 3

Human Peripheral Blood T Regulatory Cells, Functionally Mature $CCR4^+$ Tregs and Immature-Type $CCR4^-$Tregs, Regulate Effector T Cells Regulatory $CD4^+$ T cells (Tregs) are emerging as key controllers of peripheral tolerance to self- and allo-antigens. Their dysfunction leads to the spontaneous onset of autoimmune disorders or suppression of immune responses associated with a poor disease outcome in patients with a variety of malignancies. Characterization of Tregs has been complicated by the lack of unique markers, although Tregs are primarily defined as $CD4^+$ T cells that express CD25 (IL-2Rα), CTL-associated antigen 4 (CTLA-4) and scurfin, a fork-head box P3 (FoxP3) gene product. These genes are expressed at a constitutively high level and suppress the proliferation of activated T cells and dendritic cells. To date, at least two subsets of human natural Tregs, memory-type $CD25^+$ $CD4^+$ Tregs and natural naïve $CD4^+$ Tregs (nnTregs), are known to exist. In addition, a separate group of IL-10 producing murine effector-memory Tregs ($T_{REM}$) and human Tr1 cells, which acquire regulatory functions by polarizing human $CD25^-$ $CD4^+$ T cells, have also been reported. These various Tregs differ in their homing patterns reflected by the differential expression of chemokine receptors. For example, CCR7 is expressed by nnTregs directing their homing to secondary lymphoid organs; CXCR4 is thought to participate in the retention of Tregs in bone marrow, CCR6 in the recruitment of $T_{REM}$ into the skin, and CCR4 is associated with Tregs that migrate into the periphery. However, the nature of $CCR4^+$ Tregs in human peripheral blood remains unresolved, particularly, considering the fact that less than 5% of circulating $CD4^+$ T cells may be Tregs ($CD25^+CD4^+$, FIG. 14A), while CCR4-expressing cells account for 20% lymphocytes, which also include Th2-polarized $CD4^+$ T cells that also exert suppressive functions via production of immunosuppressive cytokines. Although the mechanism of T cell regulation is shown to require both IL-10 and TGFβ for some Tregs (Tr1) or perforin/granzyme- and cell contact-dependent process, the extent of the participation of immunosuppressive cytokines has not been elucidated.

The following experiments, through the use of chemotoxins, demonstrate that human peripheral blood Tregs consist of, at least, two distinct subsets, memory-type $CCR4^+$ Tregs and naïve-type $CCR4^-$ Tregs.

Materials and Methods

Plasmid Constructs

Cloning strategy for chemokine-fused antigens has been described previously. Briefly, the mature sequence for human TARC was cloned as described in Example 2. A truncated form of *Pseudomonas* exotoxin (PE38) that does not have cell binding and internalization domain was recloned by PCR as described in Example 2. TARC was genetically fused in frame with PE38 (TARC-PE38) or with irrelevant tumor antigen OFA-iLRP (TARC-OFA) and expressed from bacterial expression vector pET11 (Stratagene, La Jolla, Calif.). All constructs were verified by the DNA sequencing (Keck DNA Sequencing, Yale University, New Haven, Conn.). Production of chemokine-fused proteins from TARC-PE38 or TARC-OFA-containing BL21 (DE3) *E. coli* cells (Stratagene) has been previously described previously. The integrity and purity (>90%) of recombinant proteins were tested by SDS-PAGE under reducing conditions and verified by Western blot hybridization with monoclonal 9E10 anti-c-myc Ab (Sigma).

Human Peripheral Blood Cell Isolation

Human peripheral blood samples were collected from healthy donors in accordance with Human Subject Protocol #2003054 by the Health Apheresis Unit and the Clinical Core Laboratory of the National Institute on Aging (NIA). $CD4^+$ cells were isolated by negative selection using human CD4 subset column kit (R&D Systems Inc., Minneapolis, Minn.) from PBMCs after Ficoll-Paque (GE Healthcare Bio-Sciences Corp., Piscataway, N.J.) density gradient separation according to the manufacturers' instructions. $CCR4^+CD4^+$ or $CCR4^-CD4^+$ cells were selected as described previously (Pappas, J. et al. (2006) *Immunol Lett.* 102:110-114). Briefly, $1\times10^8$ $CD4^+$ cells (in 900 µl of PBS containing 0.5% BSA and 2 mM EDTA were stained with 100 µl of anti-CCR4-FITC Ab (R &D Systems) for 45 mM at 4-8° C., and separated using anti-FITC microbeads (Miltenyi Biotec, Auburn, Calif.) and MS columns (Miltenyi Biotech). To achieve the highest purity, two consecutive MS column runs were used and $CCR4^-$ cells were further depleted using LD columns (Miltenyi Biotec). $CD25^+$ cells were selected from $CD4^+$ cells or $CCR4^+CD4^+$ and $CCR4^-CDR^{4+}$ fractions using anti-CD25 Ab-coated microbeads (Dynabeads CD25; Dynal Biotech/Invitrogen Corp., Carlsbad, Calif.). Beads were removed from cells using DETACHaBEAD CD4/CD8 reagent (Dynal Biotech/Invitrogen Corp.). Cell purity was determined by FACS which was in average 94-98% for $CD25^{high}CCR4^+CD4^+$ ($CCR4^+$ Tregs) and 83-89% for $CD4^+CD25^{high}CCR4^-$ cells ($CCR4^-$ Tregs, a lower purity of $CCR4^-$ Tregs presumably was due to slightly lower CD25 expression). $CD8^+$ cells were selected using human T cell CD8 subset column kit (R&D Systems). Monocyte/macrophage-enriched PBMCs were isolated by plastic adherence and were irradiated with 4500 rad before use as APCs for MLR or feeder cells.

Flow Cytometry Analysis

Expression of surface markers was detected by staining with the appropriate fluorochrome-conjugated Abs followed by FACS using a FACScan flow cytometer and Cell Quest Pro software (BD Biosciences). The following Abs used were from R&D Systems: anti-CCR4-FITC, anti-CD25-PE, and anti-CCR7-FITC. Anti-CLA-FITC, anti-CD45RA-PE, anti-CD62L-PE and anti-CD95L (FasL) Abs were from BD Pharmingen (Franklin Lakes, N.J.). Anti-Granzyme A-PE (BD Pharmingen) and anti-Granzyme B-PE (Caltag Laboratories, Burlingame, Calif.) Abs were used for intracellular staining. Cells were fixed and permeabilized with Fix&Perm Cell Permeabilization Kit (Caltag Laboratories). To study the effect of activation some cells were stimulated with MACSiBead particles-coupled with anti-CD3/CD28/CD2 Abs (Human T cell activation/expansion kit, Myltenyi Biotec) according to manufacturer's instructions.

RNA Isolation and RT-PCR

Total RNA from flow-sorted fractions of $CD4^+$ cells was isolated using Trizol reagent (Invitrogen Corp.) and RNeasy kit (Qiagen). RT-PCR was performed with primers reported by others: human FoxP3, 5'-GAAACAGCACATTCCCAGAGTTC-3' (SEQ ID NO:19) and 5'-ATGGCCCAGCGGATGAG-3'(SEQ ID NO:20); human glyceraldehyde-3-phosphate dehydrogenase, 5'-TGTGGAAGGGCTCATGACCACAGTCCAT-3' (SEQ ID NO:21) and 5'-GCCTGCTTCACCACCTTCTT GATG-3'(SEQ ID NO:22).

Suppression Assays

To test Tregs suppression, the responder $CD8^+$ T cells ($5 \times 10^4$ each) were labeled with 0.5 µM carboxyfluorescein diacetate succinimidyl ester (CFSE, CellTrace Cell Proliferation Kit, Molecular Probes/Invitrogen Corp.) for 10 minutes in PBS at 37° C. Then cells were cultured with autologous APCs ($5 \times 10^4$) and titrated amounts of Tregs for 4-5 days in the presence of soluble anti-CD3 Ab (0.5 µg/ml) in 96-well plates. At the end of experiment cells were stained with anti-CD8-PE Ab staining were analyzed by FACS. $CD8^+CFSE^{low}$ cells were considered as proliferated cells. The results are expressed as percentage of proliferation of $CD8^+$ cells cultured in the absence of $CD4^+$ cells. Some Tregs were treated for 1 hour with soluble anti-CD3 Ab (5 µg/ml) and anti-CD28 Ab (1 µg/ml), washed and were cultured for 3 days in the presence of recombinant human IL-2 (100 U/ml). Alternatively, anti-CD3 Ab (0.5 µg/ml) was present or absent in the culture medium throughout the experiment with $CD8^+$ cells in MLR assay with allogeneic APCs. To neutralize FasL, anti-human FasL/CD95L Ab (20 µg/ml, NOK-1, NA/LE, BD Pharmingen) or isotype-matched control Ab (BD Pharmingen) were used. Tregs or control cells were pre-incubated with Abs for 1 hour at 37° C. before adding to responder cells.

Depletion of $CCR4^+$ Cells Using TARC-Chemotoxin

Human peripheral blood $CD4^+$ and $CD8^+$ cells were treated with 10 µg/ml of TARC-PE38 or TARC-OFA or with PBS for 2 days in complete RPMI medium supplemented with 10% FBS and 5% human AB serum. Expression of CCR4 and cell death were evaluated using anti-CCR4-FITC Ab and propidium iodide (PI, Roche Diagnostics Corp.). Cell viability of purified $CD4^+$ cell fractions treated as described above was assessed using Cell Proliferation Reagent WST-1 (Roche Diagnostics Corp.).

Effects of $CCR4^+$ Cell Depletion on $CD4^+$ Cell Activation and Proliferation in Response to Polyclonal Stimulation After overnight treatment with 10 µg/ml with proteins, $CD4^+$ cells were washed and activated with soluble 5 µg/ml anti-CD3 (BD Pharmingen) and 1 µg/ml anti-CD28 Abs (BD Pharmingen) for 3 days which was continued for 4 more days in the presence of 10 U/ml of IL-2 (PeproTech Inc., Rocky Hill, N.J.). Then, secreted cytokines were measured using Multiplex (BioRad), and cells were stained with anti-CD25-PE and anti-CCR4-FITC Abs and analyzed by FACS. Uptake of 100 nM of 5-bromo-2'-deoxiurydine (BrdU) for 2 hours was used to test for cell proliferation (Colorimetric Cell Proliferation ELISA, Roche Diagnostics Corp., Roche Applied Science, Indianapolis, Ind.). To study a role of Th2-type non-Tregs, $CD4^+$ cells, depleted from $CD25^+$ cells, were overnight treated with 10 µg/ml of TARC-PE38, or TARC-OFA, or PBS, and, after extensive washes in PBS, the cells were activated with plate-bound anti-CD3 Ab (0.5 µg/ml) and 1 µg/ml soluble anti-CD28 Ab. Then, after 3 days cultivation, $3 \times 10^6$ cells/ml were plated and cultured for 3-5 more days in the presence of IL-2 (10 U/ml) to determine secreted cytokines.

Animals

All mice were bred and housed at the National Institute of Aging animal facility, Baltimore, Md. Animal care was provided in accordance with the procedures outlined in a Guide for the Care and Use of Laboratory Animals (NIH Publication No. 86-23, 1985). The TCR transgenic pmel-1 ($V\alpha1V\beta13$ T cell receptor for $H-2D^b$-restricted mouse and human gp100 epitope) mice have been described previously[36]. C57BL/6 mice were purchased from Jackson (The Jackson Laboratory, Bar Harbor, Me.).

Effect of $CCR4^+$ Cell Depletion on Antigen-Specific T Cell Proliferation

The synthetic peptides (purity>99%, Peptide Technologies, Washington, D.C.) used are human-gp100$_{25-33}$ (KVPRNQDWL; SEQ ID NO:23) and MOPC-315 Ig$_{91-101}$ (ALWFRNHFVFGGGTK; SEQ ID NO:24). Pmel mice were vaccinated subcutaneously twice at 3-wk intervals with 10 µg human gp100$_{25-33}$ peptide emulsified in 100 µl incomplete Freund's adjuvant (IFA, Sigma). Three weeks after the second vaccination, splenocytes were harvested and were treated with either PBS or 10 µg/ml TARC-PE38 or TARC-OFA for 24 hours. After washings, splenocytes were cultured in complete RPMI medium containing 10% FBS, 20 IU/ml recombinant human IL-2 and 1 µg/ml corresponding peptide (gp100$_{25-33}$ and MOPC315, respectively) for 3-5 days and tested on irradiated target cells (DCs from C57BL/6 mice) pulsed with either gp100$_{25-32}$ or MOPC315 peptides. DCs were prepared as previously described[30]. Secreted IFNγ was measured after 24 hours of incubation by ELISA. Proliferation of splenocytes was measured by BrdU incorporation after 5 days of culture.

For suppression assays, $CD8^+$ and $CD4^+$ cells were isolated from pmel or C57BL/6 splenocytes, respectively, using murine T cell subset column kits (R&D Systems). $CD4^+$ cells were overnight treated with 10 µg/ml TARC-PE38 or TARC-OFA, or PBS and, after washings, they were mixed at 1:1 ratio with pmel $CD8^+$ cells and stimulated with gp100$_{25-32}$ peptide-pulsed irradiated APCs. Cell proliferation was evaluated after 5 days by BrdU incorporation. Mouse $CCR4^+$ expression was detected with goat anti-mouse CCR4 Ab (Axxora LLC, San Diego, Calif.) followed by staining with FITC-conjugated secondary Ab (Sigma).

Statistical Analysis

All data are representative of at least 2 experiments. For all graphs data represent mean±SD of triplicates. Differences were tested using Student's t test or one-way ANOVA followed by post hoc Scheffe's F-test. A p value less than 0.05 was considered statistically significant.

Results

Two Distinct Subtypes of Tregs

Figure 14A:
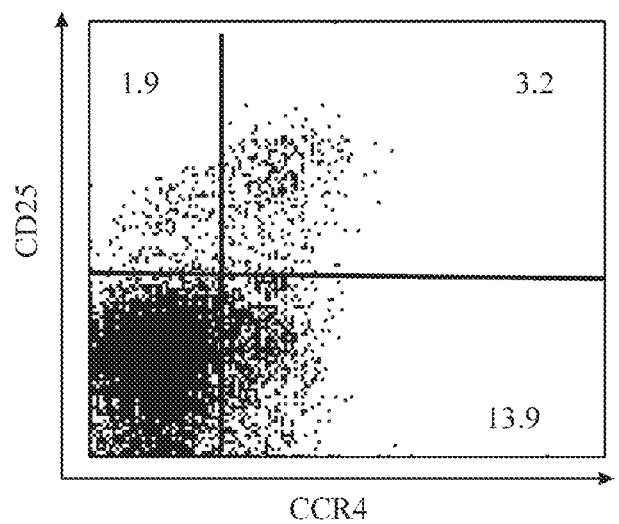
FIGS. 14A-D depict the expression of CCR4 on Tregs in freshly isolated human peripheral blood CD4$^+$ T cells (A). CD4$^+$ cells, negatively selected from PBMCs, were stained for expression of CD25 and CCR4 and tested by FACS. Numbers indicate percentage of cells in the corresponding quadrant. CCR4$^+$ and CCR4$^-$ Tregs express FoxP3 and suppress CD8$^+$ cell proliferation (B). Expression of FoxP3 and GAPDH tested by RT/PCR on total RNA extracted from FACS-sorted human peripheral blood CD4$^+$ cell fractions. (C) Tregs regulate T cell proliferation. CFSE-stained CD8$^+$ cells were cultured with various subsets of CD4$^+$ cells (indicated). X-axes indicate ratio of cells used starting from $5 \times 10^4$ CD8$^+$ cells mixed with $1 \times 10^4$ CD4$^+$ cells. CD8$^+$ cells were stimulated with equal numbers of autologous APCs plus 0.5 μg/ml of soluble anti-CD3 Ab for 4 days. Cells were stained with PE-conjugated anti-CD8 Ab and were analyzed by FACS. The results are expressed as percentage of proliferation of CD8$^+$ cells cultured in the absence of CD4$^+$ cells. Data represent mean±SD of triplicates. *P<0.01, CD25$^+$CCR4$^+$ versus CD25$^-$CCR4$^+$ cells at the corresponding ratio. (D) Phenotype of Tregs in human peripheral blood. CD25$^+$CD4$^+$ cells were purified and stained with Abs to corresponding surface markers (indicated) by FACS. Numbers represent percentage of cells in the corresponding quadrant. Shown, representative data from at least three independent experiments with similar results.
Figure 14B:
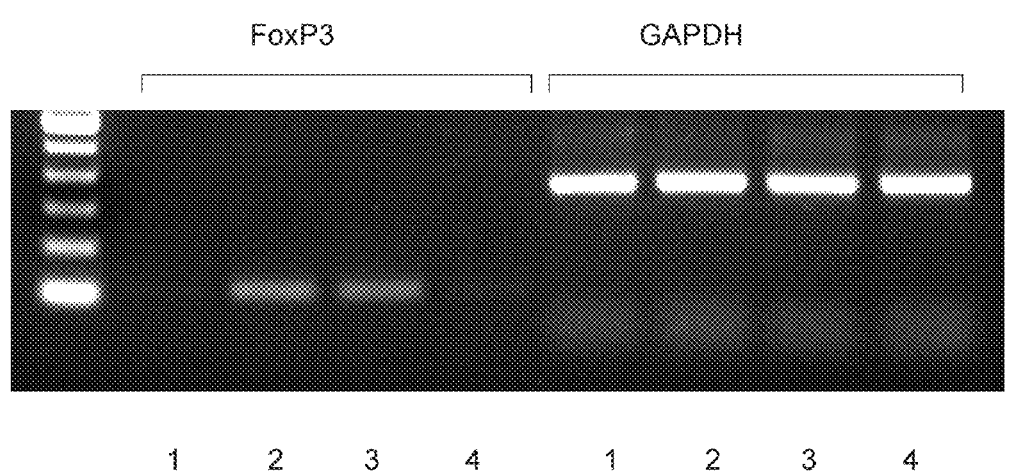
Figure 14C:
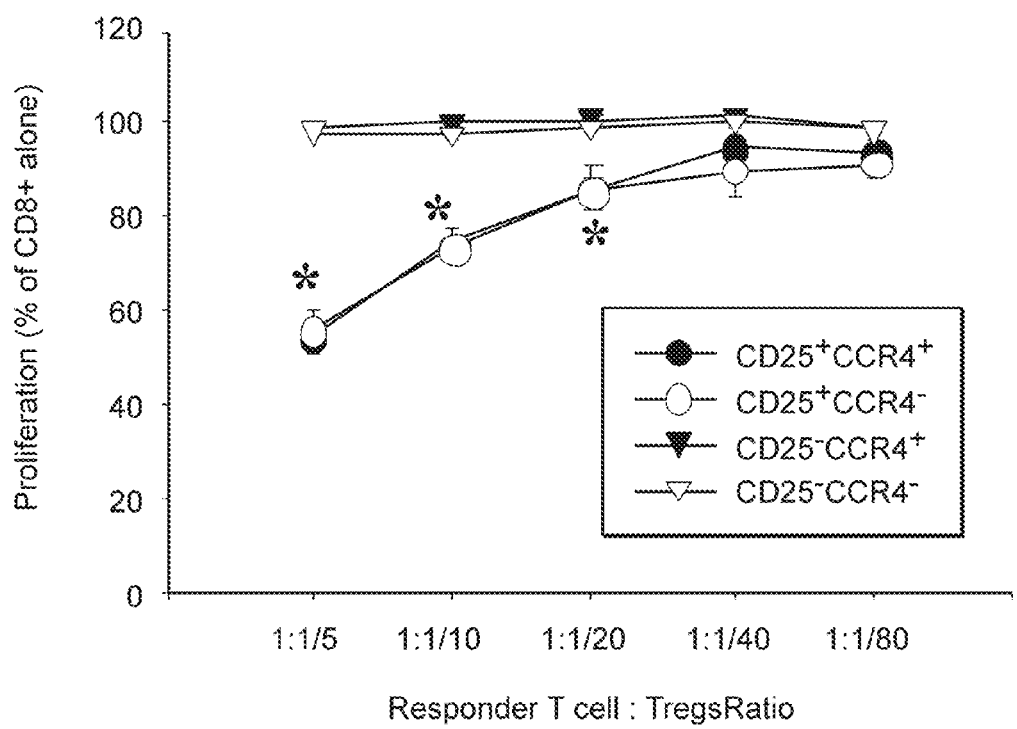
Figure 14D:
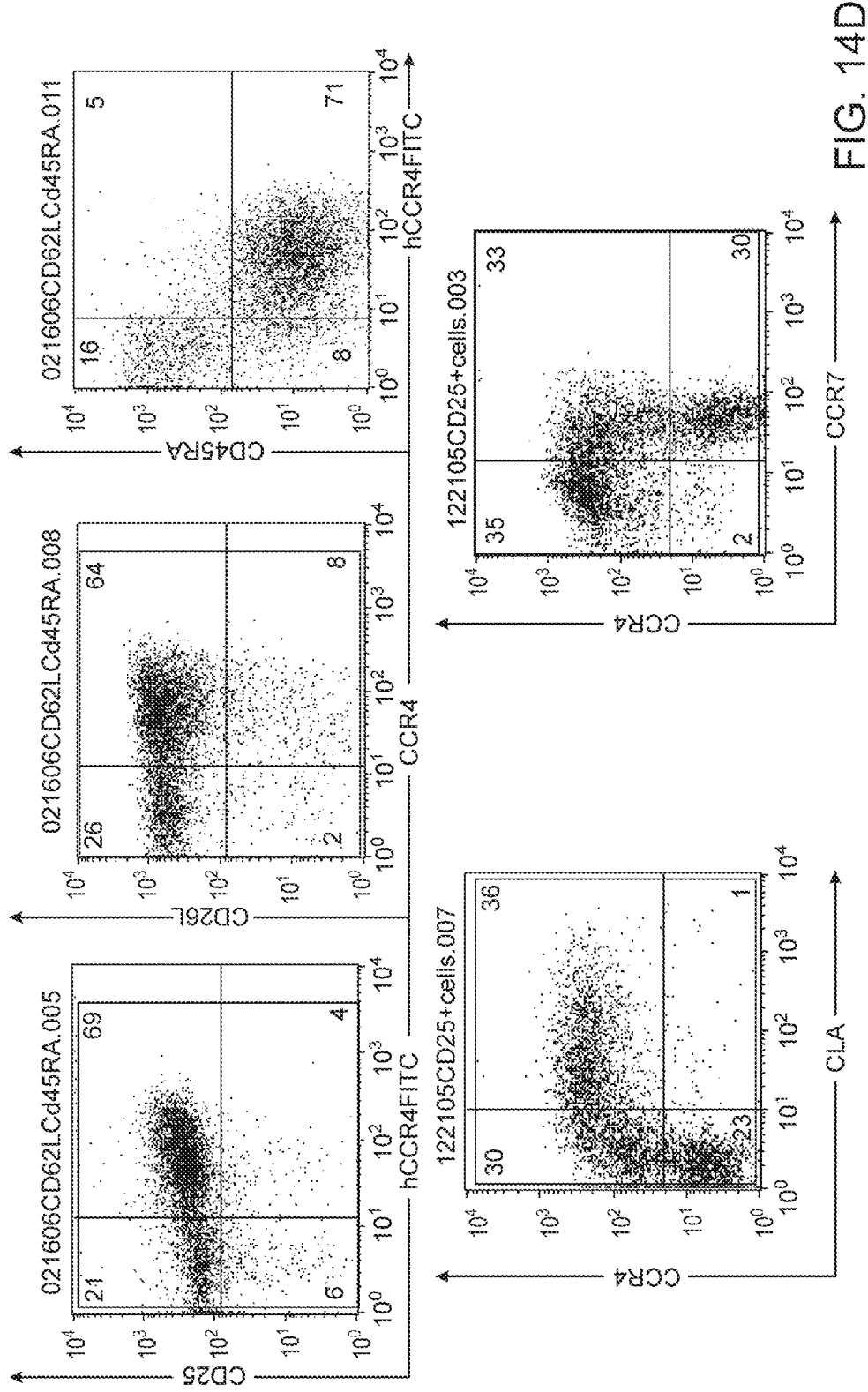

In humans, $CD25^+CD4^+$ cells represent up to 5% of circulating peripheral blood $CD4^+$ T cells that can be further divided into two distinct populations of cells, $CCR4^+CD25^+$ (3.2±0.5%) and $CCR4^-CD25^+$ (1.9±0.6%) (FIG. 14A). These two populations expressed FoxP3 mRNA (FIG. 14B) and suppressed proliferation of autologous $CD8^+$ (FIG. 14C) and $CD4^+$ cells T cells stimulated with anti-CD3 Ab. In contrast, CCR4⁻CD25⁻/low, CCR4⁺CD25⁻/low CD4⁺ T cells did not express FoxP3 (FIG. 14B) nor suppress T cell proliferation (FIG. 14C). Thus, CCR4⁺CD25⁺ and CCR4⁻CD25⁺ cells exert regulatory activity and designated CCR4⁺ Tregs and CCR4⁻Tregs, respectively. Moreover, the cells appear to differ in their differentiation state. While CCR4⁺ Tregs (>90%) did not express CD45RA indicating to their memory phenotype, most of CCR4⁻Tregs expressed CD45RA⁺ and belonged to naïve cells (FIG. 1d). The cells presumably home to different organs, since CLA⁺, a skin-homing marker, was exclusively expressed by CCR4⁺ Tregs as was also reported by others In contrast, CCR4⁻Tregs did not express CLA (FIG. 14D), but expressed CCR7 and CD62L, markers for homing to secondary lymphoid organs. However, CD62L and CCR7 were also expressed by the majority (≥90%) or half of CCR4⁺ Tregs, respectively (FIG. 14D), suggesting that Tregs may actually consist of at least three distinct subgroups, namely CCR4⁺CCR7⁻, CCR4⁺CCR7⁺, CCR4⁻CCR7⁺ (FIG. 14D).

CCR4⁺ and CCR4⁻ Tregs are Functionally Different Regulatory Cells.

Figure 15B:
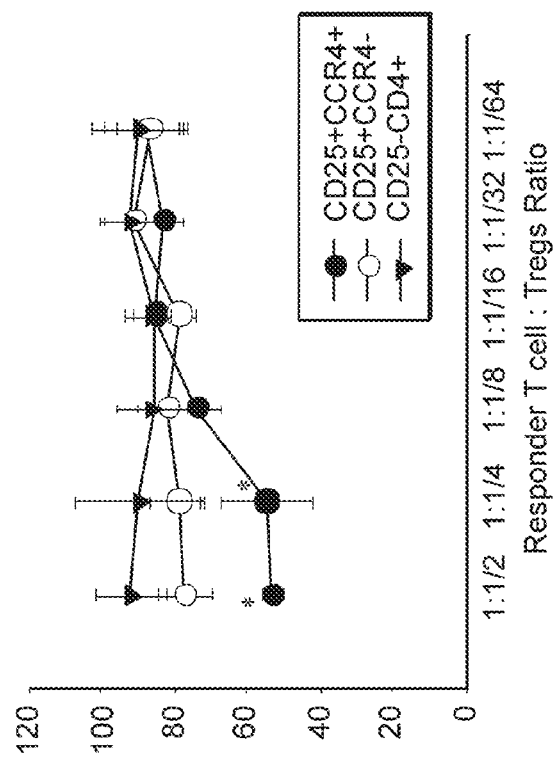
FIGS. 15A-B depict CCR4$^-$Tregs activity requires an initial activation through TCR. Freshly isolated CCR4$^+$ Tregs and CCR4$^-$Tregs were tested for ability to suppress proliferation of CFSE-labeled allogeneic CD8$^+$ cells in MLR with irradiated allogeneic APCs in the presence (A) or absence (B) of 0.5 μg/ml soluble anti-CD3 Ab. Shown as percentage of proliferation of CD8$^+$ cells cultured in the absence of Tregs, representative data (mean±SD of triplicates) from at least three independent experiments with similar results. *P<0.01 versus CD25$^-$CD4$^+$ cells at the corresponding ratio.
Figure 15A:
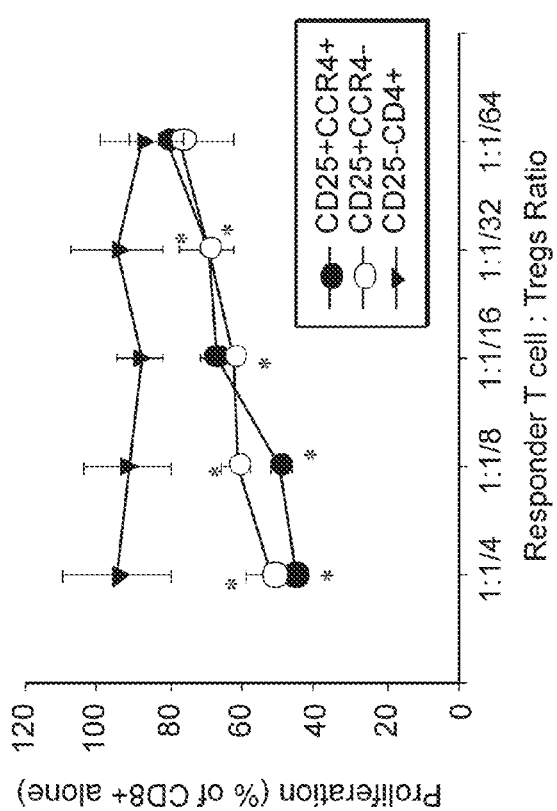

Based on the expression of markers for non-activated naïve cells (CD45RA⁺) and LN homing (FIG. 14D), we have postulated that CCR4⁻Tregs require an initial activation or instruction to become suppressive cells. Traditional assays, typically performed in the extended presence of anti-CD3 Ab, would also activate Tregs and would not functionally discriminate between these two Treg populations (See, for example, FIG. 14C). To study this, we tested Tregs for suppression of CD8⁺ T cell-mediated MLR in the absence or presence of anti-CD3 Ab. As expected, both CCR4⁻ and CCR4⁺Tregs suppressed MLR at almost identical cellular concentrations (FIG. 15A) in the presence of anti-CD3 Ab. However, when anti-CD3 Ab was omitted from the assay, only CCR4⁺Tregs but not CCR4⁻Tregs inhibited MLR (FIG. 15B). Thus, the Tregs consist of two functionally distinct populations, mature CCR4⁺Tregs that exhibit regulation independent of pre-activation, and an immature-type of CCR4⁻Tregs that require an initial TCR signaling to become a fully active regulatory cell. However, CCR4⁻Tregs are pre-sensitized, as only a brief (1 hour) pre-treatment with soluble anti-CD3 Ab was sufficient to activate their suppressive effects (data not shown).

CCR4⁺ and CCR4⁻ Tregs Use Different Regulatory Pathways

Figure 16A:
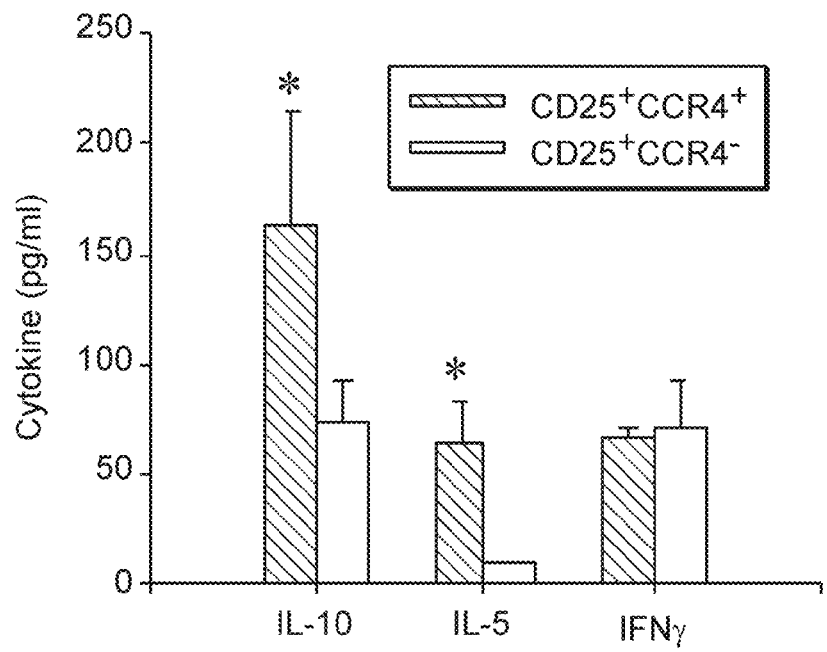
FIG. 16A-F depict the mechanism of Treg suppression. Cell contact is required for Tregs suppression. Despite the fact that conditioned media (CM) from CCR4$^+$Tregs incubated with CD8$^+$ cells contains higher amounts of IL-10 and IL-5 (A), it does not affect proliferation of CD8$^+$ cells (B). To study effects of secreted suppressive factors, titrated amounts of CM from the suppression assay with CCR4$^+$ Tregs (Med CD25$^+$CCR4$^+$) or CCR4$^-$Tregs (Med CD25$^+$CCR4$^-$) were mixed with anti-CD3 Ab (0.5 μg/ml)—stimulated CD8$^+$ T cells. Shown as percentage of proliferation of CD8$^+$ T cells alone (mean±SD of triplicates). *$^†$P<0.01 for comparisons with CD25$^+$CCR4$^-$ or CD25$^-$CCR4$^+$ groups, respectively. (C) CCR4$^-$ but not CCR4$^+$ cells express GZ-B after activation. Purified cells were activated with bead-bound antiCD3/CD28 Abs and were cultured for 5 days. IL-2 (10 u/ml) was added to culture medium during the last 2 days of incubation. (D) CCR4+ but not CCR4-Tregs express CD95L/FasL. Purified cells were incubated in RPMI medium supplemented with 10% FBS and 5% human AB serum for 16 hours. Surface expression of CD95L/FasL and intracellular expression of GZ-B were evaluated after staining with appropriate Abs by FACS. Histograms, thick line represents CD95L expression and thin line-isotype-matched control. Numbers represent percentage of cells in the corresponding quadrant or gate. (E) CCR4$^-$Tregs express CD95L/FASL after activation. CCR4$^-$Tregs were activated with bead-bound anti-CD3/CD28 Abs (activated) or cultured without stimuli (non-activated) for 16 hours. Cells were surface-stained with anti-CCR4 and antiCD95L Abs. Numbers represent percentage of cells in the corresponding quadrant. Representative data from two independent experiments with similar results. (F) Suppression-induced with Tregs is dependent on CD95L/FasL. Subsets of Tregs or non-Treg CD25$^-$CD4$^+$ T cells ($2.5 \times 10^4$) were mixed with CFSE-labeled CD8$^+$ T cells ($5 \times 10^4$) in four day assay in the presence of anti-CD3 Ab (0.5 μg/ml) and autologous APCs. CD4$^+$ cell subsets were pre-treated with 20 μg/ml anti-CD95L neutralizing or control Abs for 1 hour at 37° C. and then were mixed with CD8$^+$ cells and APCs. Shown as percentage of proliferation of CD8$^+$ cells cultured in the absence of Tregs (mean±SD of triplicates). *P<0.01 for comparisons with control Ab treatment. Representative data from at least three independent experiments with similar results.
Figure 16B:
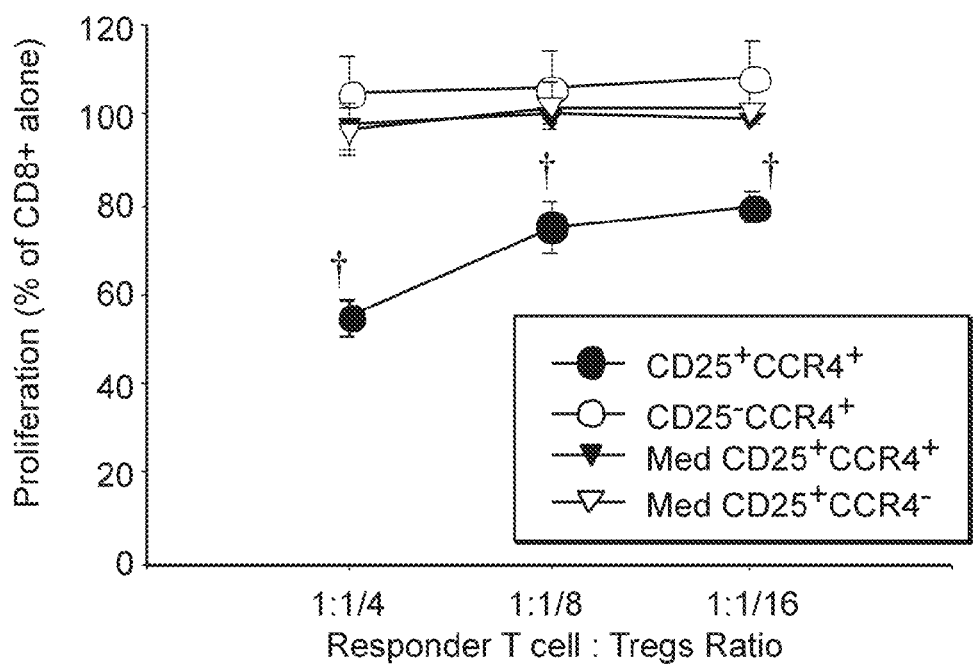
Figure 16C:
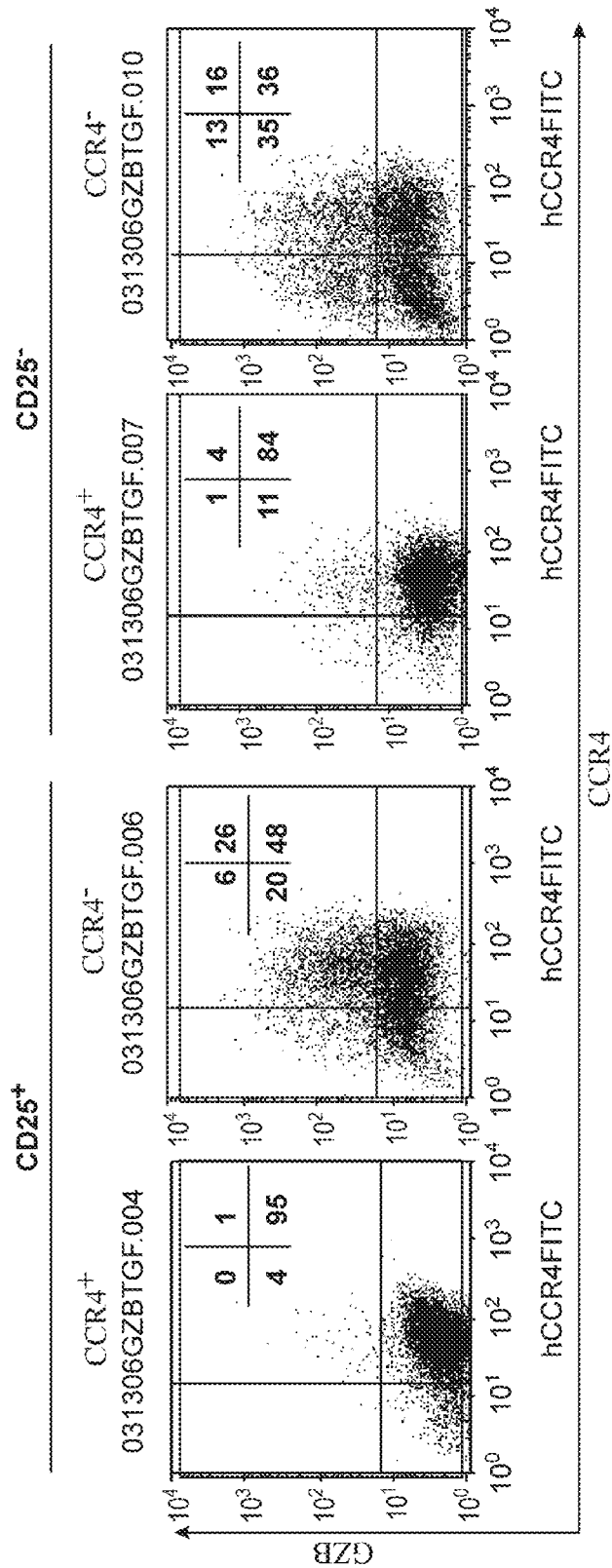

It is widely accepted that Tregs require cell contact to exert their suppressive effects. In concordance, conditioned medium from activated mixtures of Treg/non-Treg cells, that contained significant amounts of IL-10 (FIG. 16A), failed to inhibit proliferation of non-Treg cells (Med CD25⁺CCR4⁺, FIG. 16B). Recent reports have revealed that Tregs utilize both granzymes A and B (GZ-A and GZ-B) in contact-mediated cell suppression. However, no expression of any GZ-A in Tregs was detected regardless of CD3/CD28 Abs activation (data not shown). Similarly, no significant GZ-B expression was detected in non-activated Tregs (data not shown). In contrast, activation with bead-bound anti-CD3/CD28 Abs induced significant GZ-B expression in CCR4⁻ Tregs and non-Tregs, but none in CCR4⁺Tregs (FIG. 16C).

Figure 16D:
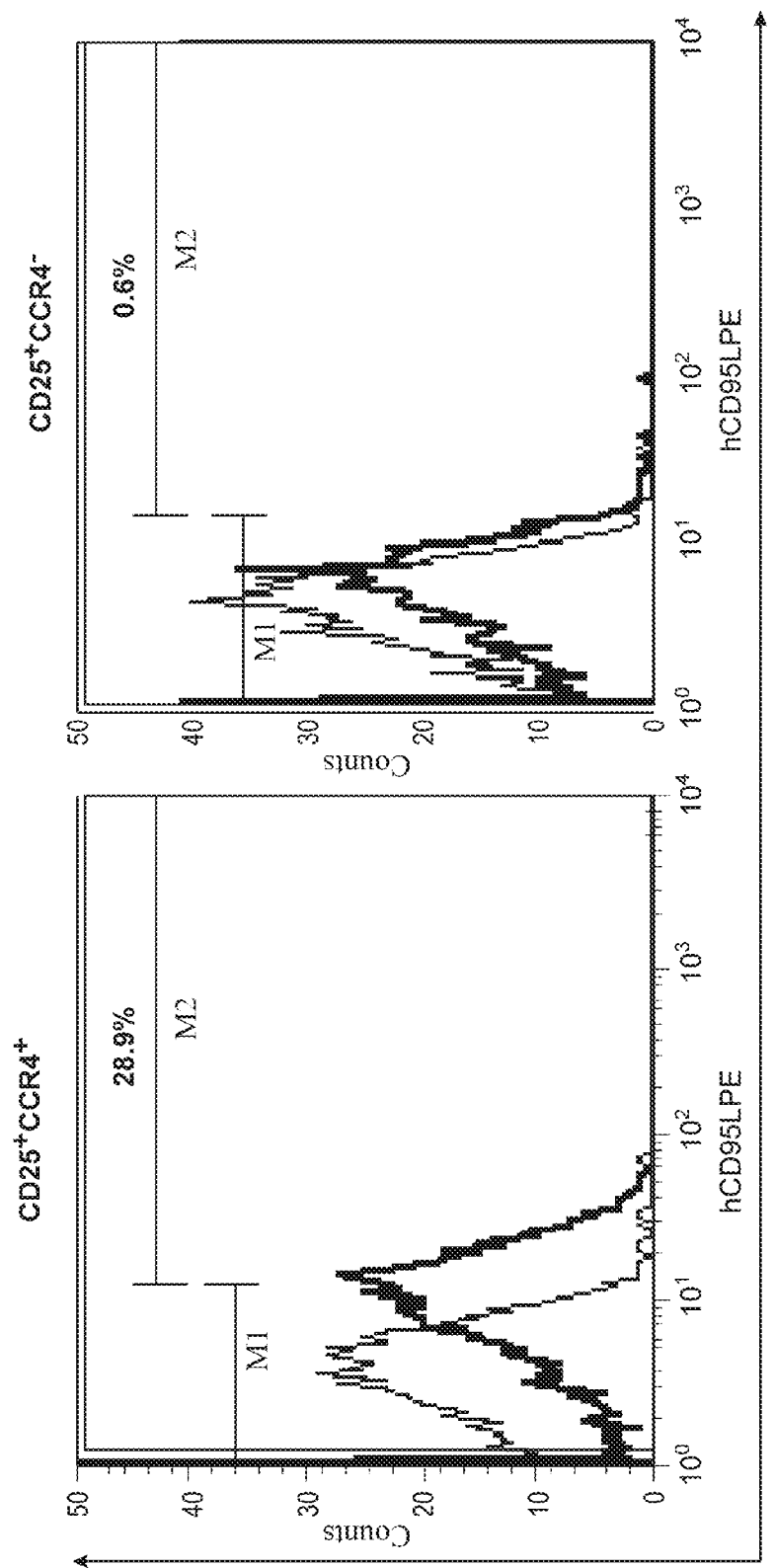
Figure 16E:
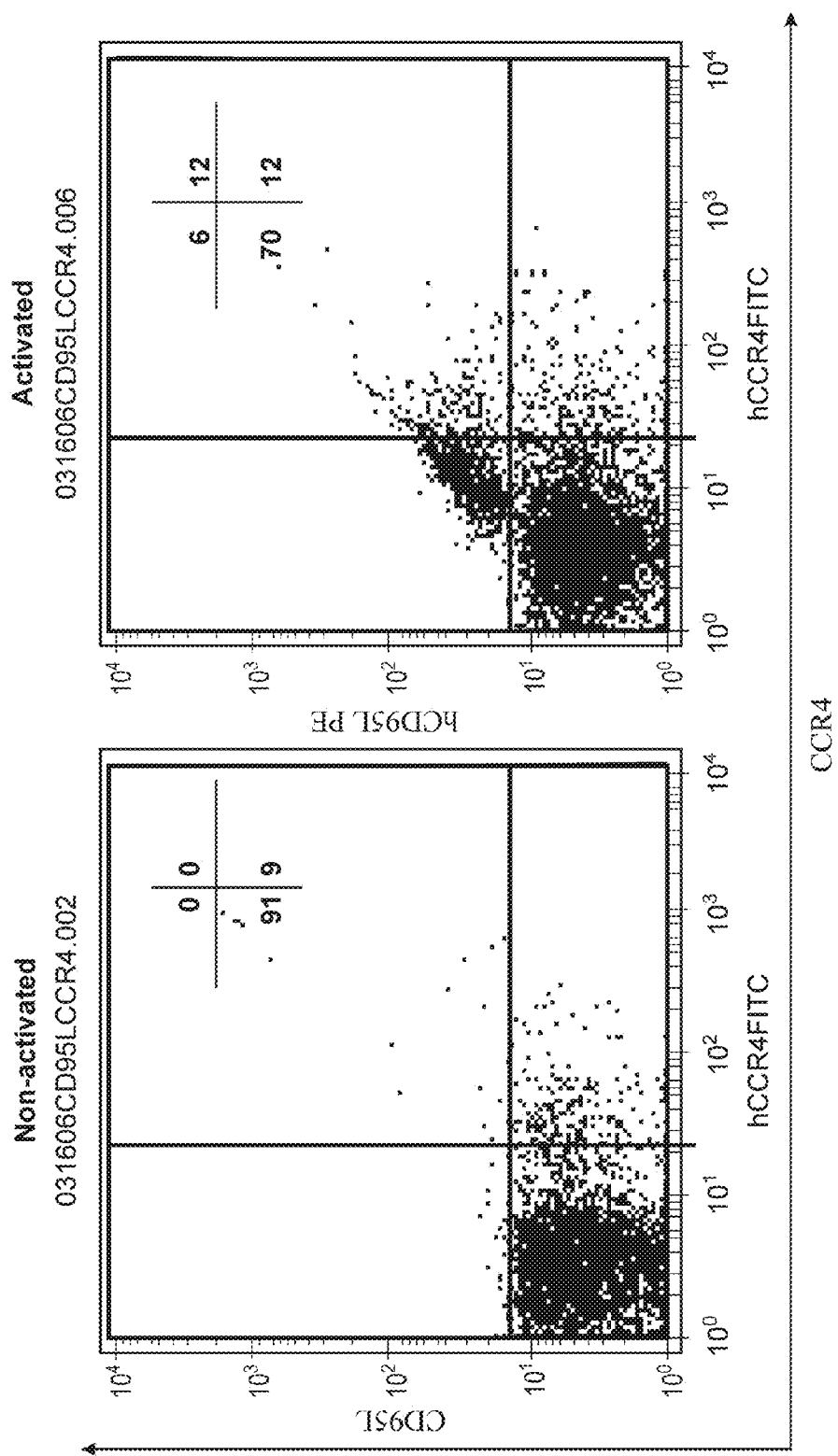
Figure 16F:
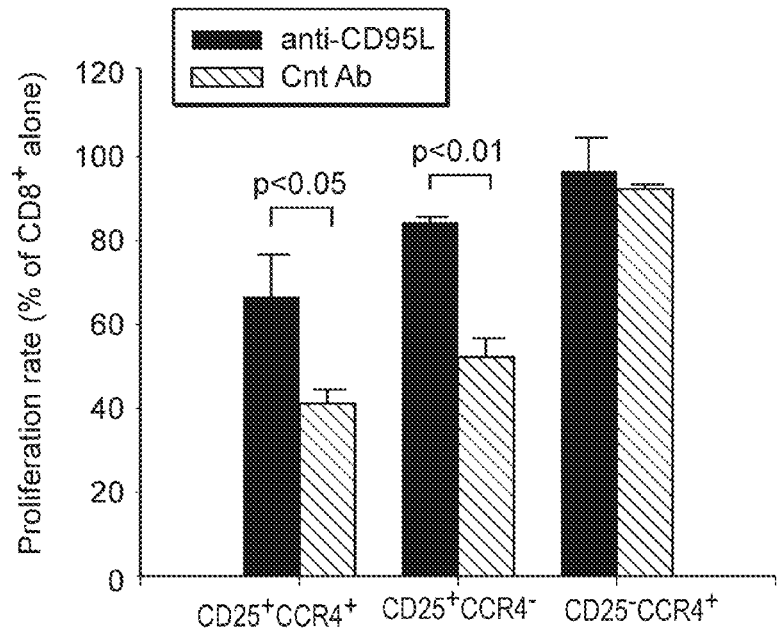

Thus, granzymes are presumably not used by CCR4⁺ Tregs, but they may employ other contact-mediated suppressive mechanisms, such as Fas/FasL (CD95/CD95L) signaling, which plays a major role in the physiological regulation of T cell homeostasis. To test this, expression of FasL/CD95L was assessed on these cells. Resting CD4⁺ T cells are reported not to express FasL, although it was shown to appear within 8 hours of stimulation. Moreover, FasLex-pression was not detected on the surface of freshly isolated Tregs (data not shown). Similarly, no FasL was expressed on CCR4⁻Tregs (FIG. 16D) or non-Tregs (both CCR4⁺ and CCR4⁻ populations, data not shown). In contrast, significant levels of FasL were detected exclusively on CCR4⁺ Tregs after a brief in vitro culture without any stimuli (FIG. 16D). Moreover, upon activation with bead-bound anti-CD3/CD28 Abs, CCR4⁻Tregs also expressed significant levels of FasL, but predominantly in the CCR4⁻Tregs that were converted to CCR4⁺ (FIG. 16E). Thus, CCR4⁻Tregs presumably contain precursor pools that require activation not only to become CCR4⁺Tregs, but also to utilize FasL. To demonstrate the functional role of FasL, Tregs suppression assay was performed in the presence of FasL neutralizing Ab. As shown in FIG. 16F, incubation with neutralizing anti-FasL Ab, but not control Ab, reversed the suppressive activities of both CCR4⁺Tregs and CCR4⁻Tregs significantly augmenting proliferation of CD8⁺ T cells induced with anti-CD3 Ab. Therefore, these data clearly indicate that the need for the contact-dependent regulation exerted by Tregs can be at least in part explained by utilization of FasL signaling pathways.

CCR4⁺CD4⁺ Non-Treg Cells Control Th1-Polarization, while CCR4⁺ Tregs Regulate Proliferation of T Cells.

Figure 17A:
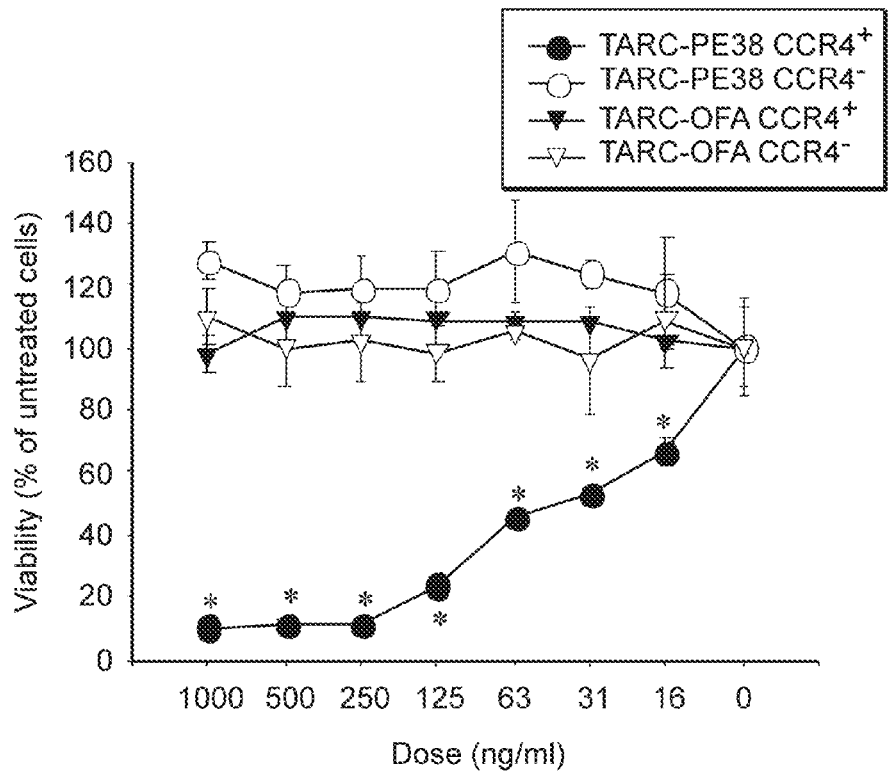
FIGS. 17A-E demonstrate that TARC-PE38 specifically kills purified CCR4$^+$CD4$^+$ cells (A). Control treatments were TARC-OFA and PBS. Shown as percentage of viable cells to untreated cells evaluated by WST assay after 2 days of treatment. Representative data (mean±SD of triplicates) from at least three independent experiments with similar results. *P<0.01 is for comparisons with control treatments. Depletion of CCR4$^+$ cells promotes CD4$^+$ cell proliferation (B) and Th1 polarization (C). CD4$^+$ T cells were overnight pretreated with 10 μg/ml TARC-PE38, or TARC-OFA, or PBS and were activated with soluble anti-CD3/anti-CD28 Abs. BrdU incorporation (B) and secreted IFNγ (C) were measured after seven days of incubation. In parallel, proliferation and IFNγ secretion of purified CD4$^+$CCR4$^+$ and CD4$^+$CCR4$^-$ T cells was tested after the same stimulation. Depletion of the Th2-type non-Tregs with TARC-chemotoxin (TARC-PE38) reduces IL-10 (D) and augments IFNγ (E). CD4$^+$ T cells were first depleted from CD25$^+$ cells (Tregs) using anti-CD25 Ab-coated magnetic beads and the remaining cells were treated with TARC-PE38, TARC-OFA or PBS and stimulated with plate-bound anti-CD3 Ab. At the indicated time points, cytokines were measured by ELISA in conditioned media. Shown, representative (data mean±SD of triplicates) from at least two independent experiments with similar results. *P<0.01 for comparisons with PBS-treated groups.
Figure 17B:
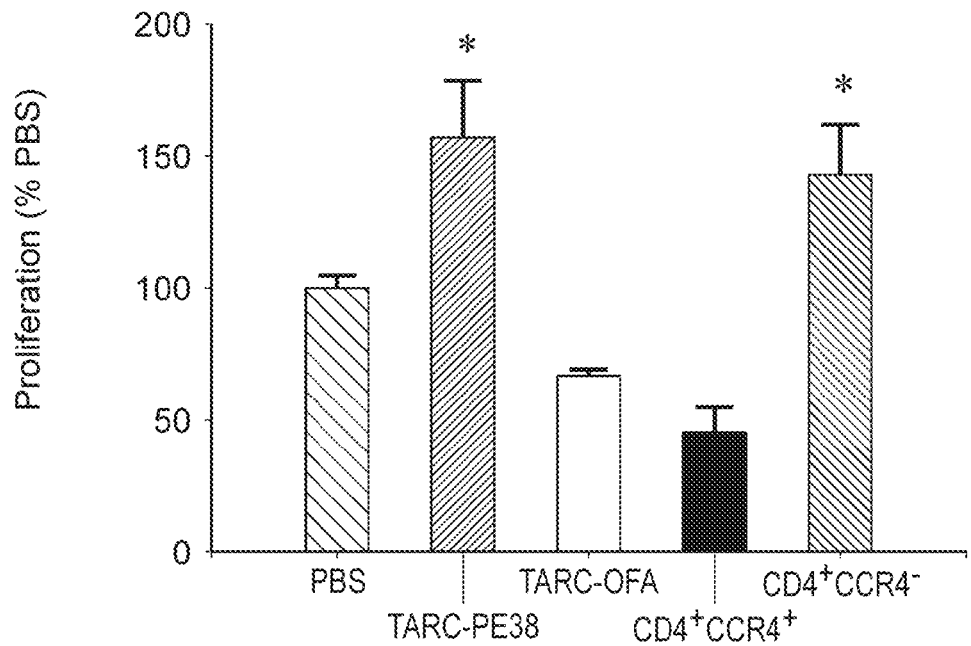
Figure 17C:
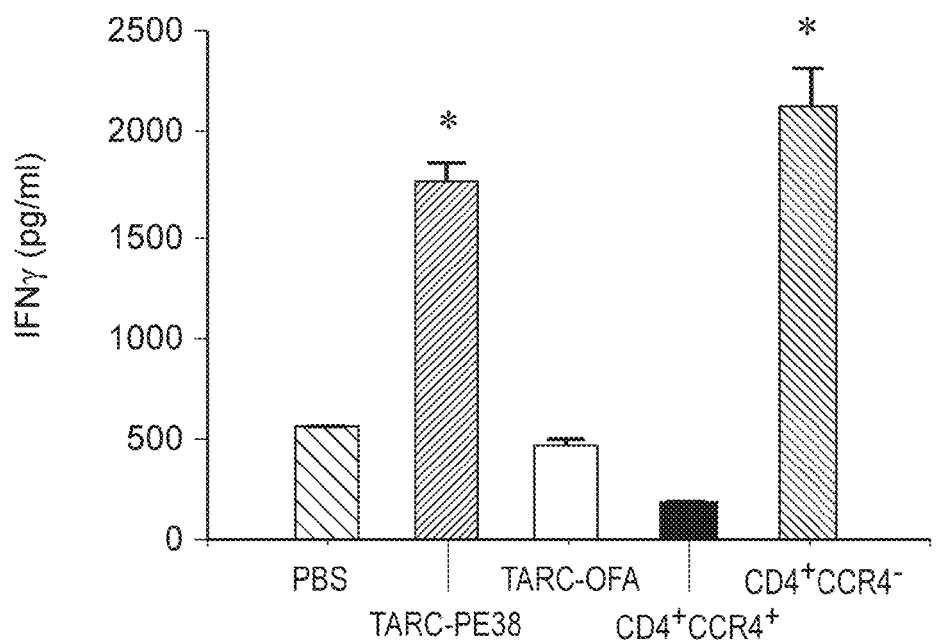

In human peripheral blood, expression of CCR4 was detect on two types of cells, Tregs and Th2-type CD4⁺ non-Treg cells that may be potentially immunomodulatory expressing the immunosuppressive cytokine IL-10. Therefore, to assess their regulatory functions, a specific and direct method that depletes CCR4-expressing cells utilizing chemotoxin, a recombinant protein expressing TARC/CCL17 fused with a truncated exotoxin PE38 (TARC-PE38) was developed. TARC-PE38, but not control TARC fused with an irrelevant tumor antigen (TARC-OFA), specifically killed the CCR4⁺ T cells at nM concentrations (FIG. 17A). Purified CD4⁺ T cells were pretreated overnight with TARC-PE38, or with TARC-OFA, or mock treated with PBS; and, after several washing steps, they were stimulated with soluble anti-CD3/CD28 Abs. The magnitude of proliferation (P<0.01, FIG. 17B) was significantly augmented in cells pretreated with TARC-PE38, but not with TARC-OFA or PBS. Moreover, in contrast to TARC-OFA or PBS, the TARC-PE38 pretreatment also induced significantly higher IFNγ (p<0.01, FIG. 17C) and lower IL-10 and IL-5 (data not shown) secretions. Given that TARC-PE38 specifically and selectively killed CCR4⁺T cells, these data suggest that CCR4⁺ cells kept transiently suppressed the proliferation and Th1-polarization of CCR4⁻ cells. In support of this conclusion, purified/sorted CCR4⁻CD4⁺ T cells alone (<5% contaminating CCR4⁺ cells, CD4⁺CCR4⁻, FIGS. 17B,C) demonstrated a similar levels of proliferation and IFNγ production as T cells treated with TARC-PE38, while highly purified CCR4⁺CD4⁺ T cells proliferated poorly and failed to secrete IFNγ (CD4⁺CCR4⁺, FIGS. 17B,C). Thus, CCR4⁺ T cells are primary cells that control Th1-polarization of CCR4⁻CD4⁺ T cells.

Figure 17D:
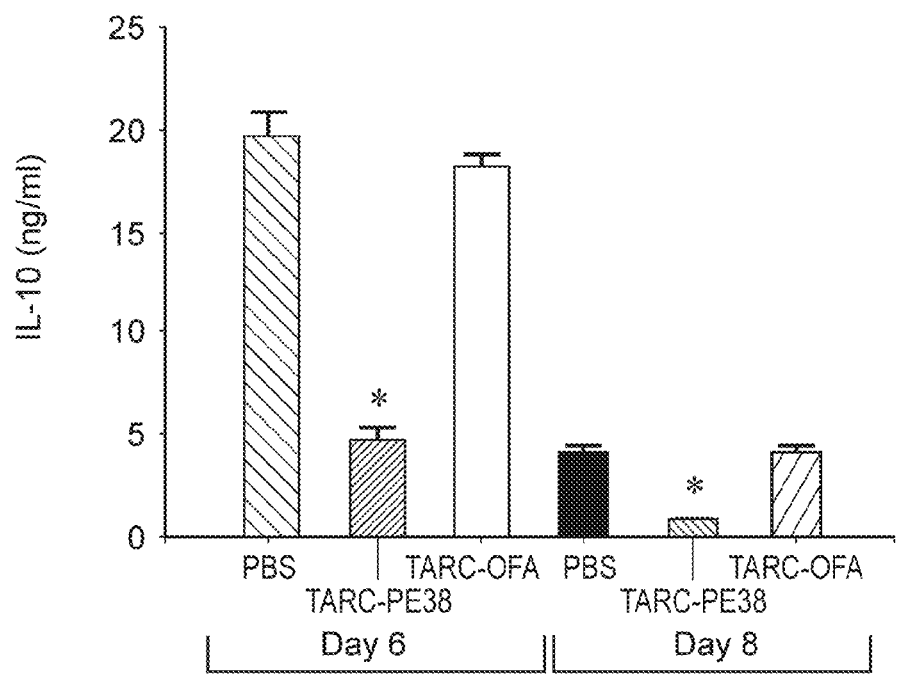
Figure 17E:
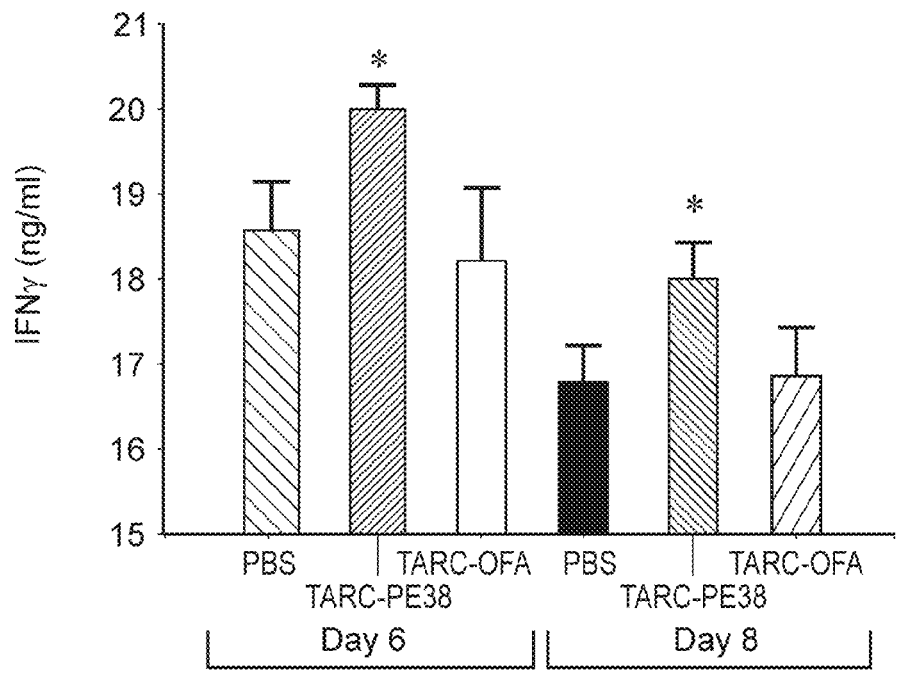

To further dissect roles of CCR4⁺ Tregs and CCR4⁺ non-Tregs, CD4⁺ T cells were thoroughly depleted of CD25-expressing cells (Tregs) using anti-CD25 Ab-coupled beads. The remaining non-Treg CD4⁺ cells (≥95% pure) proliferated well and did not inhibit the proliferation of other T cells (see CD25⁻CCR4⁺, FIG. 14A), indicating to Tregs as a primary regulator of T cell proliferation. The CD25-depleted cells were subsequently pretreated with TARC-PE38, or TARC-OFA, or PBS, after which the cells were stimulated with anti-CD3/CD28 Abs. The cells pretreated with TARC-PE38 demonstrated dramatically reduced expression of IL-10 (FIG. 17D) and other Th2-type cytokines such as IL-4 and IL-5, but significantly increased levels of IFNγ production (FIG. 17E). In contrast, the cells pretreated with PBS or TARC-OFA produced significantly higher levels of IL-10 (FIG. 17D) and IL-4 and IL-5, and less IFNγ (FIG. 17E). Taken together, these data suggest that, while cell proliferation is primarily regulated by CCR4$^+$ Tregs via cell-contact and FasL-dependent process, Th1 polarization is controlled by non-Treg CCR4$^+$ Th2 type cells presumably through the action of immunomodulatory cytokines IL-10 and IL-4.

Figure 18A:
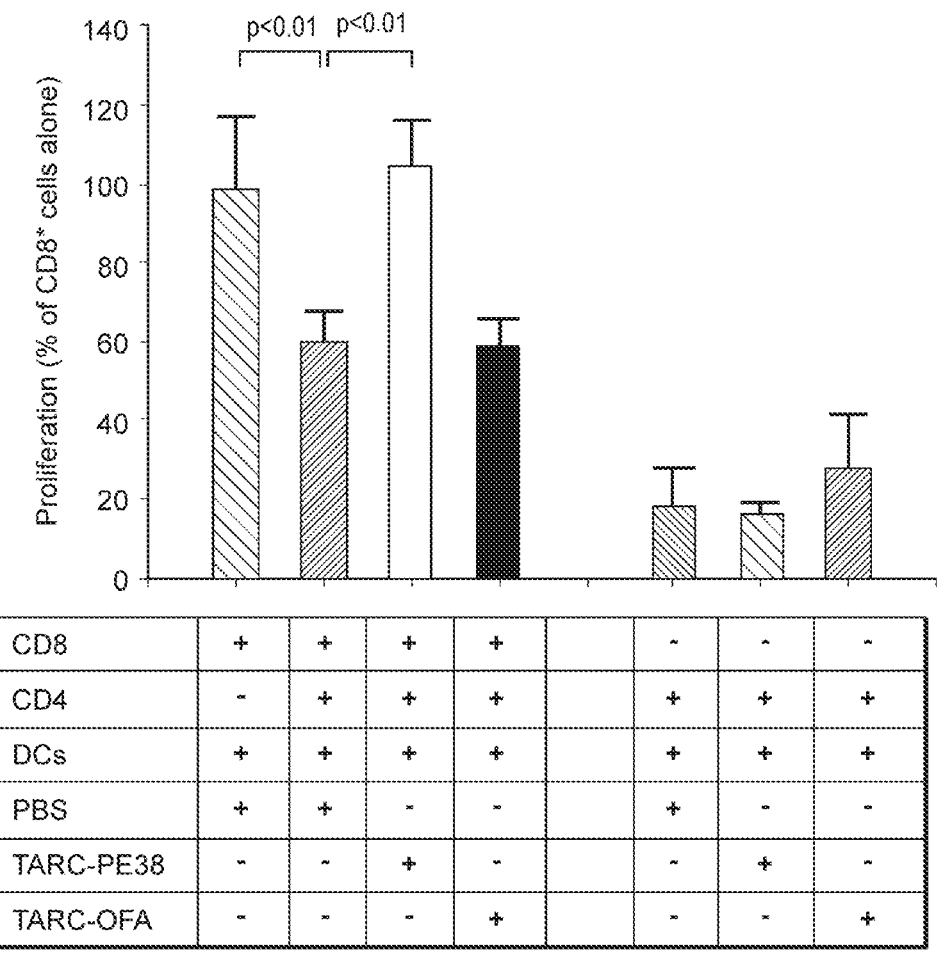
FIGS. 18A-C demonstrate that the depletion of murine CCR4$^+$Tregs augments murine antigen specific T cell responses. (A) CD4$^+$ T cells from C57BL/6 mice were pretreated with TARC-PE38 or TARC-OFA, or PBS as in FIG. 4. Then cells were mixed with pmel CD8$^+$ cells at 1:1 ratio and stimulated for five days with irradiated DCs from C57Bl/6 mice pulsed with 1 μg/ml of gp100$_{25-32}$ peptide. (B) Pmel splenocytes were pretreated with TARC-PE38, TARC-OFA or PBS as above and, then, cells were cultured for three days with gp100$_{25-32}$ or control MOPC315 peptides. CD8$^+$ cell proliferation was tested by BrdU incorporation. Data are shown as percentage of proliferation of CD8$^+$ cells alone. (C) IFNγ (μg/ml) was measured in culture media of cells used in (B). Shown, representative data (mean±SD of triplicates) from at least three independent experiments with similar results.
Figure 18B:
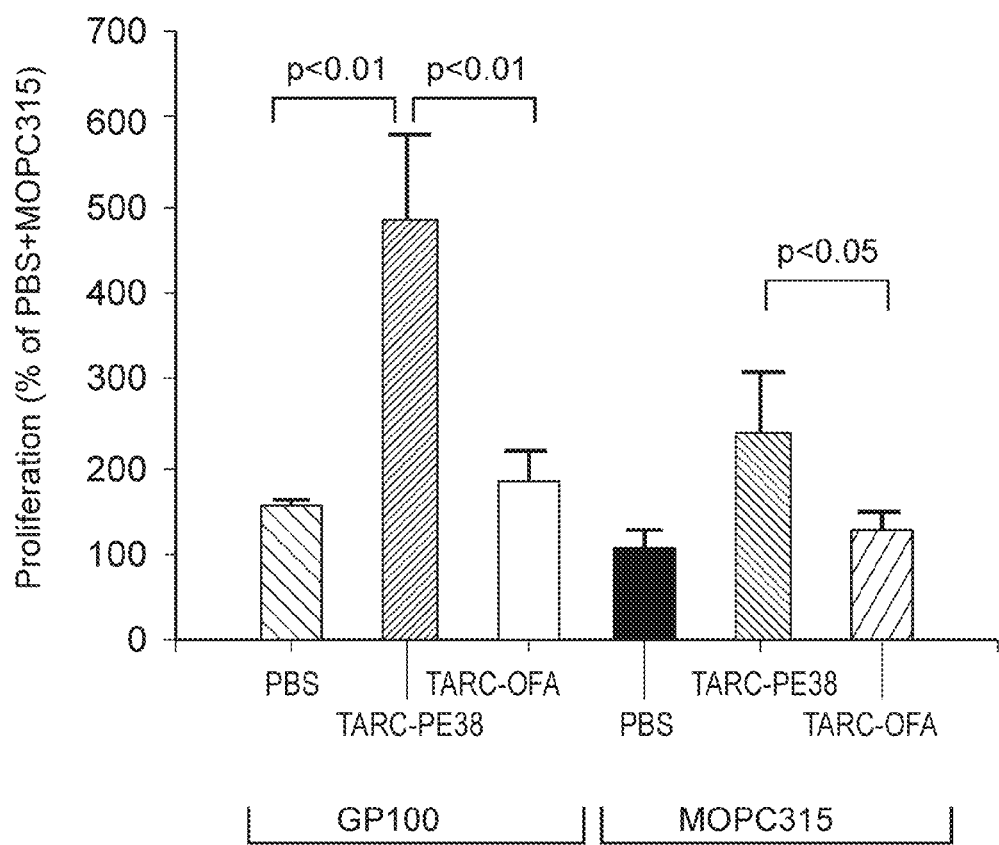
Figure 18C:
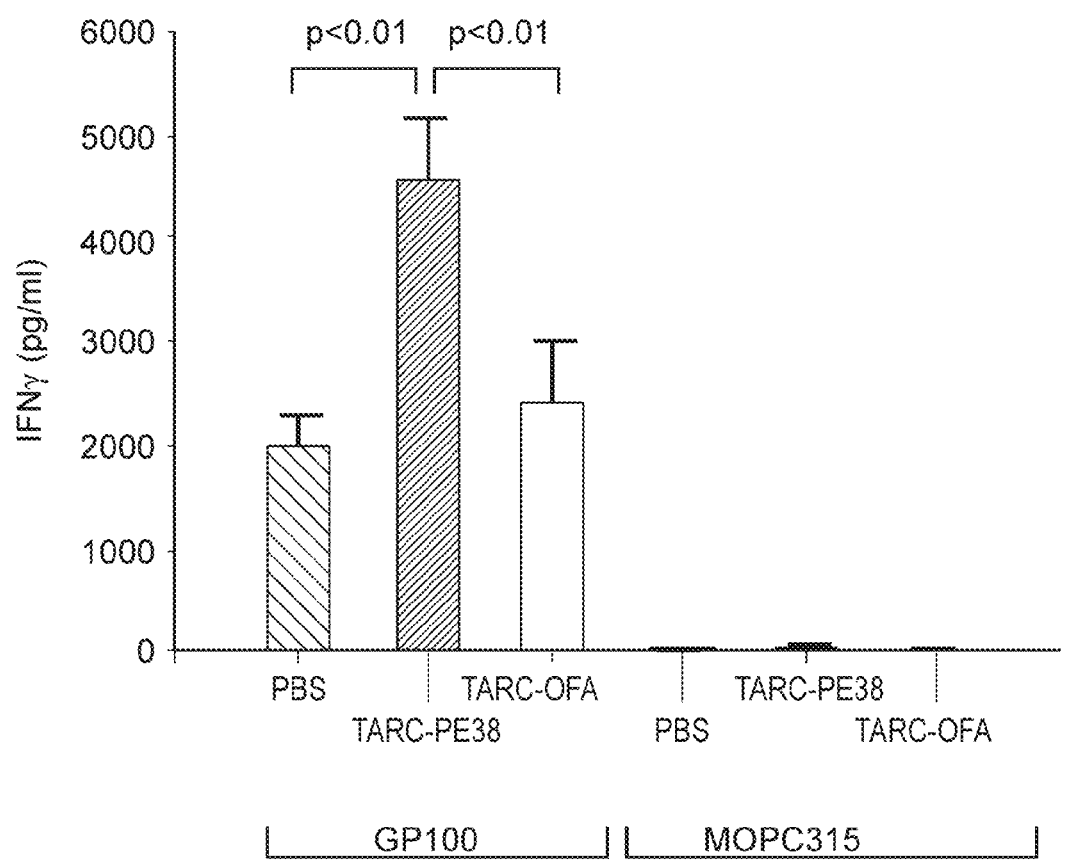

Practical Implications: Depletion of Murine CCR4$^+$ T Cells Augments Antigen Specific CD8$^+$ T Cell Responses Tregs have also been reported to suppress responses of tumor antigen-specific CD8$^+$ T cells. Initial experiments indicated that only a fraction of CD4$^+$ T cells in naïve C57BL/6 mouse peripheral blood and spleen expressed CCR4 (4.2±0.5% and 2.6±0.4%, respectively). These cells presumably also include Tregs, as specific proliferation (FIG. 18A) and IFNγ production of CD8$^+$ T cells from TCR transgenic pmel mice to melanoma-derived gp100$_{25-32}$ peptide was significantly suppressed upon the addition of MHC-matched spleen-derived CD4$^+$ T cells, regardless of whether CD4$^+$ T cells were initially treated with PBS or pretreated with TARC-OFA. In contrast, the proliferation could be completely restored when the CD4$^+$ T cells were initially pretreated with TARC-PE38 (FIG. 18A). In addition, pmel splenocytes pretreated with TARC-PE38 yielded significantly higher cell proliferation (FIG. 18B) and IFNγ production (FIG. 18C) when stimulated with the gp100$_{25-32}$ peptide, compared to cells pretreated with TARC-OFA or PBS (FIGS. 18B,C). TARC-PE38 pretreated cells also showed slightly increased (but significant) proliferative response in general even when stimulated with control peptide (p<0.05, FIG. 18B). Control peptide stimulation failed to produce IFNγ (FIG. 18C). Thus, these results demonstrate that murine spleen-derived CCR4$^+$CD4$^+$ T cells, presumably Tregs, suppress antigen-specific CD8$^+$T cell responses. This also indicates that the suppressive state of T cells can be completely reversed by the depletion of CCR4$^+$ T cells using TARC-PE38.

Conclusion

The data presented in this example demonstrate that human peripheral blood contains several distinct populations of suppressive CD4$^+$ T cells: two discrete populations of Tregs that regulate T cell proliferation, differentiated by expression of CCR4, and non-Treg CCR4$^+$ T cells that control Th1-cell polarization. Morover, the data indicate that FasL is significantly expressed on the surface of CCR4$^+$ Tregs even upon a brief in vitro culture without any additional stimulation. In contrast, CCR4$^-$Tregs only expressed FasL after stimulation with anti-CD3/CD28 Abs. Importantly, neutralizing anti-CD95L Ab significantly reversed the inhibitory effects of Tregs on the proliferation of CD8$^+$ T cells, though involvement of additional suppressive mechanisms can not be ruled out since the inhibition was only partial. Thus, these data indicate that both CCR4$^+$Tregs and CCR4$^-$Tregs utilize the FasL/Fas signaling pathway, although later requires an additional stimulation via TCR to express FasL and exert regulation.

Taken together, we have characterized functionally distinct mature and immature subtypes of Tregs circulating in human peripheral blood, distinguished by the expression of chemokine receptors, such as CCR4 and CCR7, and utilization of unique suppressive mechanisms. Therefore, utilizing chemotoxins that specifically kill CCR4$^+$ T cells we demonstrate that these cells also exert suppression of Th1-polarization and T cell proliferation, and their depletion can significantly augment antigen specific CD8$^+$ T cell responses and production of Th1-type cytokines. Accordingly, chemotoxins will have significant clinical implications for treatment of autoimmune diseases, tumors and chronic infections, which are shown to be controlled by Th2-type cytokine skewed cells and Tregs.

Example 4

Depletion of Treg Cells for Improvement of Vaccine-Induced T Cell Response

The following experiment was performed to determine if TARC-chemotoxins will specifically kill Treg cells. Since the systemic depletion of CD25$^+$ Treg cells can also induce harmful unpredicted autoimmunity, such as induction of onset of gastritis, thyroidis, oophoritis or prostates. We aimed to use chemotoxins locally to target only Tregs at the site of vaccine expression or in local draining LN. The following data demonstrate that chemotoxin-mediated Treg depletion affects T cell responses in vitro. TARC-chemotoxins efficiently depleted proportion of CCR4$^+$CD4$^+$ cells within naïve T cell population after overnight treatment. In contrast, proportion of CCR4-negative CD4$^+$ or CD8$^+$ T cells were not affected by the treatment (both human or mouse cells, data not shown). Pre-treatment of human CD4$^+$ T cells or purified CD4$^+$CD25$^+$ T cells for two days with TARC-PE38, but not TARC-OFA or PBS, was able to eliminate their suppressive effects on proliferation of αCD3-induced proliferation of CD8$^+$ T cells. Similarly, Treg-suppressed antigen-specific proliferation of TCR transgenic CD8$^+$ T cells from pmel mice, specific for H-2D$^b$-restricted mouse and human gp100$_{25-33}$ epitope, was reversed by pretreatment of autologous CD4$^+$ cells with TARC-PE38. Moreover, pretreatment with TARC-PE38 also significantly augments IFNγ production from pmel CD8$^+$ T cells stimulated with APCs pulsed with gp100$_{25-33}$ peptide. In contrast, mock PBS or TARC-OFA treatments failed to augment either of the responses. Taken together, these data clearly demonstrate that chemotoxin-mediated depletion of Tregs improves antigen-specific CD8$^+$ T cell responses.

CONCLUSION

The above-identified experiments confirm that unwanted cells can be depleted as desired. The strategy is based on the fact that chemokines can deliver antigens to the cytosol of cells expressing specific chemokine receptors. Chimeric proteins were produced, designated chemotoxins, which consisted essentially of a chemokine fused with a toxic moiety. Only nM quantities of chemotoxins are sufficient to specifically kill tumor cells expressing the proper chemokine receptors. Moreover, injections of TARC-chemotoxin into CEM tumors established in NOD-SCID mice elicit 100% tumor-free mice. Together, these results suggest that chemotoxins are useful in the treatment of human T cell malignant diseases when a patient's immune system is severely immunocompromised by disease or age.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A pharmaceutical composition comprising a MC148-PE38 fusion molecule and a pharmaceutically acceptable carrier, wherein the MC148-PE38 fusion molecule comprises an amino acid sequence set forth in SEQ ID NO: 10.

2. The pharmaceutical composition of claim 1, wherein the fusion molecule consists of an amino acid sequence set forth in SEQ ID NO: 10.

3. A method for increasing T cell mediated immune response in a subject comprising:
administering to the subject the pharmaceutical composition of claim 1;
thereby increasing the T cell mediated immune response.

4. The method of claim 3, wherein the subject has a chronic infection.

5. The method of claim 4, wherein the chronic infection is selected from the group consisting of HIV infection, HCV infection, HBV infection and TB infection.

6. The method of claim 3, wherein the fusion molecule is administered to the location of a tumor.

7. A method of locally depleting T regulatory cells in a subject comprising:
locally administering to the subject the pharmaceutical composition of claim 1;
thereby depleting the T regulatory cells in the area of the administration of the fusion molecule.

8. The method of claim 7, wherein the subject has a chronic infection.

9. The method of claim 8, wherein the chronic infection is selected from the group consisting of HIV infection, HCV infection, HBV infection and TB infection.

10. The method of claim 7, further comprising administering to the subject a vaccine near the location of the administration of the fusion molecule.

11. A method of inhibiting immune suppression in a subject comprising:
administering to the subject the pharmaceutical composition of claim 1;
thereby inhibiting immune suppression in the subject.

12. The method of claim 11, wherein the subject has a chronic infection.

13. The method of claim 12, wherein the chronic infection is selected from the group consisting of HIV infection, HCV infection, HBV infection and TB infection.

14. The method of claim 11, wherein the fusion molecule is administered locally.

15. A method of modulating the suppressive effect of CD4+CD25+regulatory T cells of T effector cells in a subject comprising:
administering to the subject the pharmaceutical composition of claim 1;
thereby inhibiting immune suppression in the subject.

16. The method of claim 15, wherein the subject has a chronic infection.

17. The method of claim 16, wherein the chronic infection is selected from the group consisting of HIV infection, HCV infection, HBV infection and TB infection.

18. The method of claim 15, wherein the subject is being administered a vaccine.

19. The method of claim 15, wherein the fusion molecule is administered locally.

20. A method of modulating the suppressive state of T cells comprising:
administering to a subject an effective amount of the pharmaceutical composition of claim 1;
thereby inhibiting immune suppression in the subject.

21. A method of shifting an immune response from a Th2 response to a Th1 response in a subject comprising:
administering to the subject an effective amount of the pharmaceutical composition of claim 1; thereby killing Th2 cells and shifting the immune response.

* * * * *

SEQUENCE LISTING

<160> NUMBER OF SEQ ID NOS: 25

<210> SEQ ID NO 1
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 1

```
atggcacgag ggaccaacgt gggccgggag tgctgcctgg agtacttcaa gggagccatt      60 cccccttagaa agctgaagac gtggtaccag acatctgagg actgctccag ggatgccatc    120 gttttttgtaa ctgtgcaggg cagggccatc tgttcggacc ccaacaacaa gagagtgaag    180
aatgcagtta aatacctgca aagccttgag aggtctgatg gtggtggctc tggcggtggg    240
ggtagcctcg agggtggtgg tggttctaaa ccgccgcagt tcacttgggc tcagtggttc    300
gaaactcagc atatcaacat gacttctcag cagtgcacta cgctatgca ggttatcaac     360 aactaccagc gtcgttgcaa aaaccagaac actttcctgc tgactacttt cgctaacgtt    420
gttaacgttt gcggtaaccc gaacatgact tgcccgtcta caaaactcg taaaaactgc     480 catcattctg ttctcaggt tccgctgatc cattgcaacc tgactactcc gtctccgcag     540
aacatctcta actgccgtta cgctcagact ccggctaaca tgttctacat cgttgcttgc    600
gacaaccgtg accagcgtcg tgacccgccg cagtacccgg ttgttccggt tcatctggac    660
cgtatcatcg gatccgcaga gaacagaaa ctgatctcag aagaggatct ggcccaccac    720
catcaccatc actaa                                                      735
```

<210> SEQ ID NO 2
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 2

```
Met Ala Arg Gly Thr Asn Val Gly Arg Glu Cys Cys Leu Glu Tyr Phe
1               5                   10                  15

Lys Gly Ala Ile Pro Leu Arg Lys Leu Lys Thr Trp Tyr Gln Thr Ser
            20                  25                  30

Glu Asp Cys Ser Arg Asp Ala Ile Val Phe Val Thr Val Gln Gly Arg
        35                  40                  45

Ala Ile Cys Ser Asp Pro Asn Asn Lys Arg Val Lys Asn Ala Val Lys
    50                  55                  60

Tyr Leu Gln Ser Leu Glu Arg Ser Asp Gly Gly Ser Gly Gly Gly
65                  70                  75                  80

Gly Ser Leu Glu Gly Gly Gly Ser Lys Pro Pro Gln Phe Thr Trp
            85                  90                  95

Ala Gln Trp Phe Glu Thr Gln His Ile Asn Met Thr Ser Gln Gln Cys
        100                 105                 110

Thr Asn Ala Met Gln Val Ile Asn Asn Tyr Gln Arg Arg Cys Lys Asn
        115                 120                 125

Gln Asn Thr Phe Leu Leu Thr Thr Phe Ala Asn Val Val Asn Val Cys
    130                 135                 140

Gly Asn Pro Asn Met Thr Cys Pro Ser Asn Lys Thr Arg Lys Asn Cys
145                 150                 155                 160
```

His His Ser Gly Ser Gln Val Pro Leu Ile His Cys Asn Leu Thr Thr
            165                 170                 175

Pro Ser Pro Gln Asn Ile Ser Asn Cys Arg Tyr Ala Gln Thr Pro Ala
        180                 185                 190

Asn Met Phe Tyr Ile Val Ala Cys Asp Asn Arg Asp Gln Arg Arg Asp
    195                 200                 205

Pro Pro Gln Tyr Pro Val Val Pro Val His Leu Asp Arg Ile Ile Gly
    210                 215                 220

Ser Ala Glu Glu Gln Lys Leu Ile Ser Glu Glu Asp Leu Ala His His
225                 230                 235                 240

His His His His

<210> SEQ ID NO 3
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 3

| | | |
|---|---|---|
| atggcacgag ggaccaacgt gggccgggag tgctgcctgg agtacttcaa gggagccatt | 60 |
| cccttagaa agctgaagac gtggtaccag acatctgagg actgctccag ggatgccatc | 120 |
| gtttttgtaa ctgtgcaggg cagggccatc tgttcggacc ccaacaacaa gagagtgaag | 180 |
| aatgcagtta ataccctgca aagccttgag aggtctgatg gtggtggctc tggcggtggg | 240 |
| ggtagcctcg aagcttctgg aggtcccgag ggcggcagcc tggccgcgct gaccgcgcac | 300 |
| caggcttgcc acctgccgct ggagactttc acccgtcatc gccagccgcg cggctgggaa | 360 |
| caactggagc agtgcggcta ccggtgcag cggctggtcg ccctctacct ggcggcgcgg | 420 |
| ctgtcgtgga accaggtcga ccaggtgatc cgcaacgccc tggccagccc cggcagcggc | 480 |
| ggcgacctgg gcgaagcgat ccgcgagcag ccggagcaag cccgtctggc cctgaccctg | 540 |
| gccgccgccg agagcgagcg cttcgtccgg cagggcaccg caacgacga ggccggcgcg | 600 |
| gccaacggcc cggcggacag cggcgacgcc ctgctggagc gcaactatcc cactggcgcg | 660 |
| gagttcctcg cgacggcgg cgacgtcagc ttcagcaccc gcggcacgca gaactggacg | 720 |
| gtggagcggc tgctccaggc gcaccgccaa ctggaggagc gcggctatgt gttcgtcggc | 780 |
| taccacggca ccttcctcga agcggcgcaa agcatcgtct tcggcggggt gcgcgcgcgc | 840 |
| agccaggacc tcgacgcgat ctggcgcggt ttctatatcg ccggcgatcc ggcgctggcc | 900 |
| tacggctacg cccaggacca ggaacccgac gcacgcggcc ggatccgcaa cggtgccctg | 960 |
| ctgcgggtct atgtgccgcg ctcgagcctg ccgggcttct accgcaccag cctgaccctg | 1020 |
| gccgcgccgg aggcggcggg cgaggtcgaa cggctgatcg ccatccgct gccgctgcgc | 1080 |
| ctggacgcca tcaccggccc cgaggaggaa ggcgggcgcc tggagaccat tctcggctgg | 1140 |
| ccgctggccg agcgcaccgt ggtgattccc tcggcgatcc ccaccgaccc cgcaacgtc | 1200 |
| ggcggcgacc tcgacccgtc cagcatcccc gacaaggaac aggcgatcag cgccctgccg | 1260 |
| gactacgcca gccagcccgg caaaccgccg cgcgaggacc tgaagagatc cgcagaagaa | 1320 |
| cagaaactga tctcagaaga ggatctggcc caccaccatc accatcacta a | 1371 |

<210> SEQ ID NO 4
<211> LENGTH: 456
<212> TYPE: PRT

<213> ORGANISM: Artificial Sequence
<220> FEATURE:
<223> OTHER INFORMATION: Description of Artificial Sequence: Synthetic polypeptide construct

<400> SEQUENCE: 4

```
Met Ala Arg Gly Thr Asn Val Gly Arg Glu Cys Cys Leu Glu Tyr Phe
1               5                   10                  15

Lys Gly Ala Ile Pro Leu Arg Lys Leu Lys Thr Trp Tyr Gln Thr Ser
            20                  25                  30

Glu Asp Cys Ser Arg Asp Ala Ile Val Phe Val Thr Val Gln Gly Arg
        35                  40                  45

Ala Ile Cys Ser Asp Pro Asn Asn Lys Arg Val Lys Asn Ala Val Lys
    50                  55                  60

Tyr Leu Gln Ser Leu Glu Arg Ser Asp Gly Gly Ser Gly Gly Gly
65                  70                  75                  80

Gly Ser Leu Glu Ala Ser Gly Gly Pro Glu Gly Ser Leu Ala Ala
                85                  90                  95

Leu Thr Ala His Gln Ala Cys His Leu Pro Leu Glu Thr Phe Thr Arg
                100                 105                 110

His Arg Gln Pro Arg Gly Trp Glu Gln Leu Glu Gln Cys Gly Tyr Pro
            115                 120                 125

Val Gln Arg Leu Val Ala Leu Tyr Leu Ala Ala Arg Leu Ser Trp Asn
130                 135                 140

Gln Val Asp Gln Val Ile Arg Asn Ala Leu Ala Ser Pro Gly Ser Gly
145                 150                 155                 160

Gly Asp Leu Gly Glu Ala Ile Arg Glu Gln Pro Glu Gln Ala Arg Leu
                165                 170                 175

Ala Leu Thr Leu Ala Ala Ala Glu Ser Glu Arg Phe Val Arg Gln Gly
            180                 185                 190

Thr Gly Asn Asp Glu Ala Gly Ala Ala Asn Gly Pro Ala Asp Ser Gly
        195                 200                 205

Asp Ala Leu Leu Glu Arg Asn Tyr Pro Thr Gly Ala Glu Phe Leu Gly
    210                 215                 220

Asp Gly Gly Asp Val Ser Phe Ser Thr Arg Gly Thr Gln Asn Trp Thr
225                 230                 235                 240

Val Glu Arg Leu Leu Gln Ala His Arg Gln Leu Glu Glu Arg Gly Tyr
                245                 250                 255

Val Phe Val Gly Tyr His Gly Thr Phe Leu Glu Ala Ala Gln Ser Ile
            260                 265                 270

Val Phe Gly Gly Val Arg Ala Arg Ser Gln Asp Leu Asp Ala Ile Trp
        275                 280                 285

Arg Gly Phe Tyr Ile Ala Gly Asp Pro Ala Leu Ala Tyr Gly Tyr Ala
    290                 295                 300

Gln Asp Gln Glu Pro Asp Ala Arg Gly Arg Ile Arg Asn Gly Ala Leu
305                 310                 315                 320

Leu Arg Val Tyr Val Pro Arg Ser Ser Leu Pro Gly Phe Tyr Arg Thr
                325                 330                 335

Ser Leu Thr Leu Ala Ala Pro Glu Ala Ala Gly Glu Val Glu Arg Leu
            340                 345                 350

Ile Gly His Pro Leu Pro Leu Arg Leu Asp Ala Ile Thr Gly Pro Glu
        355                 360                 365

Glu Glu Gly Gly Arg Leu Glu Thr Ile Leu Gly Trp Pro Leu Ala Glu
    370                 375                 380
```

```
Arg Thr Val Val Ile Pro Ser Ala Ile Pro Thr Asp Pro Arg Asn Val
385                 390                 395                 400

Gly Gly Asp Leu Asp Pro Ser Ser Ile Pro Asp Lys Glu Gln Ala Ile
            405                 410                 415

Ser Ala Leu Pro Asp Tyr Ala Ser Gln Pro Gly Lys Pro Pro Arg Glu
        420                 425                 430

Asp Leu Lys Arg Ser Ala Glu Glu Gln Lys Leu Ile Ser Glu Glu Asp
    435                 440                 445

Leu Ala His His His His His His
    450                 455

<210> SEQ ID NO 5
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 5
atggcatcca tgcaggtacc gttctcccgc tgttgcttct catttgcgga gcaagagatt      60
cccctgaggg caatcctgtg ttacagaaat accagctcca tctgctccaa tgagggctta    120
atattcaagc tgaagagagg caaagaggcc tgcgccttgg acacagttgg atgggttcag    180
aggcacagaa aaatgctgag gcactgcccg tcaaaaagaa atccggtgg tggtggttct     240
ggcctcgagg gtggtggtgg ttctaaaccg ccgcagttca cttgggctca gtggttcgaa    300
actcagcata tcaacatgac ttctcagcag tgcactaacg ctatgcaggt tatcaacaac    360
taccagcgtc gttgcaaaaa ccagaacact ttcctgctga ctactttcgc taacgttgtt    420
aacgtttgcg gtaaccccgaa catgacttgc ccgtctaaca aaactcgtaa aaactgccat    480
cattctggtt ctcaggttcc gctgatccat tgcaacctga ctactccgtc tccgcagaac    540
atctctaact gccgttacgc tcagactccg gctaacatgt tctacatcgt tgcttgcgac    600
aaccgtgacc agcgtcgtga cccgccgcag tacccggttg ttccggttca tctggaccgt    660
atcatcggat ccgcagaaga acagaaactg atctcagaag aggatctggc ccaccaccat    720
caccatcact aa                                                        732

<210> SEQ ID NO 6
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 6

Met Ala Ser Met Gln Val Pro Phe Ser Arg Cys Cys Phe Ser Phe Ala
1               5                   10                  15

Glu Gln Glu Ile Pro Leu Arg Ala Ile Leu Cys Tyr Arg Asn Thr Ser
            20                  25                  30

Ser Ile Cys Ser Asn Glu Gly Leu Ile Phe Lys Leu Lys Arg Gly Lys
        35                  40                  45

Glu Ala Cys Ala Leu Asp Thr Val Gly Trp Val Gln Arg His Arg Lys
    50                  55                  60

Met Leu Arg His Cys Pro Ser Lys Arg Lys Ser Gly Gly Gly Gly Ser
65                  70                  75                  80

Gly Leu Glu Gly Gly Gly Gly Ser Lys Pro Pro Gln Phe Thr Trp Ala
```

```
                    85                  90                  95
Gln Trp Phe Glu Thr Gln His Ile Asn Met Thr Ser Gln Gln Cys Thr
                100                 105                 110

Asn Ala Met Gln Val Ile Asn Asn Tyr Gln Arg Arg Cys Lys Asn Gln
            115                 120                 125

Asn Thr Phe Leu Leu Thr Thr Phe Ala Asn Val Val Asn Val Cys Gly
        130                 135                 140

Asn Pro Asn Met Thr Cys Pro Ser Asn Lys Thr Arg Lys Asn Cys His
145                 150                 155                 160

His Ser Gly Ser Gln Val Pro Leu Ile His Cys Asn Leu Thr Thr Pro
                165                 170                 175

Ser Pro Gln Asn Ile Ser Asn Cys Arg Tyr Ala Gln Thr Pro Ala Asn
                180                 185                 190

Met Phe Tyr Ile Val Ala Cys Asp Asn Arg Asp Gln Arg Arg Asp Pro
            195                 200                 205

Pro Gln Tyr Pro Val Val Pro Val His Leu Asp Arg Ile Ile Gly Ser
        210                 215                 220

Ala Glu Glu Gln Lys Leu Ile Ser Glu Glu Asp Leu Ala His His His
225                 230                 235                 240

His His His

<210> SEQ ID NO 7
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 7
atggcactcg cgagacggaa atgttgtttg aatcccacaa atcgtccgat cccgaatcct      60
ttactgcaag atctatcacg cgtcgactat caggcgatag acatgactg cggacgggaa     120 gctttcagag tgacgctgca agacggaaga caaggctgcg ttagcgttgg taacaagagc     180
ttactagact ggcttcgggg acacaaggat ctctgccctc agatatggtc cgggtgcgag     240
tctctggaat tcaacgacgc tcaggcgccg aagagtctcg agggtggtgg tggttctaaa     300
ccgccgcagt tcacttgggc tcagtggttc gaaactcagc atatcaacat gacttctcag     360
cagtgcacta acgctatgca ggttatcaac aactaccagc gtcgttgcaa aaaccagaac     420
actttcctgc tgactacttt cgctaacgtt gttaacgttt gcggtaaccc gaacatgact     480
tgcccgtcta acaaaactcg taaaaactgc catcattctg gttctcaggt tccgctgatc     540
cattgcaacc tgactactcc gtctccgcag aacatctcta actgccgtta cgctcagact     600
ccggctaaca tgttctacat cgttgcttgc gacaaccgtg accagcgtcg tgaccccgccg     660 cagtacccgg ttgttccggt tcatctggac cgtatcatcg gatccgcaga agaacagaaa     720
ctgatctcag aagaggatct ggcccaccac catcaccatc actaa                    765

<210> SEQ ID NO 8
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 8
```

Met Ala Leu Ala Arg Arg Lys Cys Cys Leu Asn Pro Thr Asn Arg Pro
1               5                   10                  15

Ile Pro Asn Pro Leu Leu Gln Asp Leu Ser Arg Val Asp Tyr Gln Ala
            20                  25                  30

Ile Gly His Asp Cys Gly Arg Glu Ala Phe Arg Val Thr Leu Gln Asp
        35                  40                  45

Gly Arg Gln Gly Cys Val Ser Val Gly Asn Lys Ser Leu Leu Asp Trp
    50                  55                  60

Leu Arg Gly His Lys Asp Leu Cys Pro Gln Ile Trp Ser Gly Cys Glu
65                  70                  75                  80

Ser Leu Glu Phe Asn Asp Ala Gln Ala Pro Lys Ser Leu Glu Gly Gly
                85                  90                  95

Gly Gly Ser Lys Pro Pro Gln Phe Thr Trp Ala Gln Trp Phe Glu Thr
            100                 105                 110

Gln His Ile Asn Met Thr Ser Gln Gln Cys Thr Asn Ala Met Gln Val
        115                 120                 125

Ile Asn Asn Tyr Gln Arg Arg Cys Lys Asn Gln Asn Thr Phe Leu Leu
    130                 135                 140

Thr Thr Phe Ala Asn Val Val Asn Val Cys Gly Asn Pro Asn Met Thr
145                 150                 155                 160

Cys Pro Ser Asn Lys Thr Arg Lys Asn Cys His His Ser Gly Ser Gln
                165                 170                 175

Val Pro Leu Ile His Cys Asn Leu Thr Thr Pro Ser Pro Gln Asn Ile
            180                 185                 190

Ser Asn Cys Arg Tyr Ala Gln Thr Pro Ala Asn Met Phe Tyr Ile Val
        195                 200                 205

Ala Cys Asp Asn Arg Asp Gln Arg Arg Asp Pro Pro Gln Tyr Pro Val
    210                 215                 220

Val Pro Val His Leu Asp Arg Ile Ile Gly Ser Ala Glu Glu Gln Lys
225                 230                 235                 240

Leu Ile Ser Glu Glu Asp Leu Ala His His His His His His
                245                 250

<210> SEQ ID NO 9
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 9
atggcactcg cgagacggaa atgttgtttg aatcccacaa atcgtccgat cccgaatcct      60
ttactgcaag atctatcacg cgtcgactat caggcgatag acatgactg cggacgggaa      120 gctttcagag tgacgctgca agacggaaga caaggctgcg ttagcgttgg taacaagagc     180
ttactagact ggcttcgggg acacaaggat ctctgccctc agatatggtc cgggtgcgag     240
tctctggaat tcaacgacgc tcaggcgccg aagagtctcg aagcttctgg aggtcccgag     300
ggcggcagcc tggccgcgct gaccgcgcac caggcttgcc acctgccgct ggagactttc     360
acccgtcatc gccagccgcg cggctgggaa caactggagc agtgcggcta tccggtgcag     420
cggctggtcg ccctctacct ggcggcgcgg ctgtcgtgga accaggtcga ccaggtgatc     480
cgcaacgccc tggccagccc cggcagcggg ggcgacctgg cgaagcgat ccgcgagcag      540 ccggagcaag cccgtctggc cctgaccctg gccgccgccg agagcgagcg cttcgtccgg     600

```
cagggcaccg gcaacgacga ggccggcgcg gccaacggcc cggcggacag cggcgacgcc    660
ctgctggagc gcaactatcc cactggcgcg gagttcctcg cgacggcgg cgacgtcagc    720 ttcagcaccc gcggcacgca gaactggacg gtggagcggc tgctccaggc gcaccgccaa    780
ctggaggagc gcggctatgt gttcgtcggc taccacggca ccttcctcga agcggcgcaa    840
agcatcgtct tcggcggggt gcgcgcgcgc agccaggacc tcgacgcgat ctggcgcggt    900
ttctatatcg ccggcgatcc ggcgctggcc tacggctacg cccaggacca ggaacccgac    960
gcacgcggcc ggatccgcaa cggtgccctg ctgcgggtct atgtgccgcg ctcgagcctg   1020
ccgggcttct accgcaccag cctgaccctg gccgcgccgg aggcggcggg cgaggtcgaa   1080
cggctgatcg ccatccgct gccgctgcgc ctggacgcca tcaccggccc cgaggaggaa   1140
ggcgggcgcc tggagaccat ctccggctgg ccgctggccg agcgcaccgt ggtgattccc   1200
tcggcgatcc ccaccgaccc gcgcaacgtc ggcggcgacc tcgacccgtc cagcatcccc   1260
gacaaggaac aggcgatcag cgccctgccg gactacgcca gccagccggg caaaccgccg   1320
cgcgaggacc tgaagagatc cgcagaagaa cagaaactga tctcagaaga ggatctggcc   1380
caccaccatc accatcacta a                                             1401
```

<210> SEQ ID NO 10
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 10

```
Met Ala Leu Ala Arg Arg Lys Cys Cys Leu Asn Pro Thr Asn Arg Pro
1               5                  10                  15

Ile Pro Asn Pro Leu Leu Gln Asp Leu Ser Arg Val Asp Tyr Gln Ala
            20                  25                  30

Ile Gly His Asp Cys Gly Arg Glu Ala Phe Arg Val Thr Leu Gln Asp
        35                  40                  45

Gly Arg Gln Gly Cys Val Ser Val Gly Asn Lys Ser Leu Leu Asp Trp
    50                  55                  60

Leu Arg Gly His Lys Asp Leu Cys Pro Gln Ile Trp Ser Gly Cys Glu
65                  70                  75                  80

Ser Leu Glu Phe Asn Asp Ala Gln Ala Pro Lys Ser Leu Glu Ala Ser
                85                  90                  95

Gly Gly Pro Glu Gly Gly Ser Leu Ala Ala Leu Thr Ala His Gln Ala
            100                 105                 110

Cys His Leu Pro Leu Glu Thr Phe Thr Arg His Arg Gln Pro Arg Gly
        115                 120                 125

Trp Glu Gln Leu Glu Gln Cys Gly Tyr Pro Val Gln Arg Leu Val Ala
    130                 135                 140

Leu Tyr Leu Ala Ala Arg Leu Ser Trp Asn Gln Val Asp Gln Val Ile
145                 150                 155                 160

Arg Asn Ala Leu Ala Ser Pro Gly Ser Gly Gly Asp Leu Gly Glu Ala
                165                 170                 175

Ile Arg Glu Gln Pro Glu Gln Ala Arg Leu Ala Leu Thr Leu Ala Ala
            180                 185                 190

Ala Glu Ser Glu Arg Phe Val Arg Gln Gly Thr Gly Asn Asp Glu Ala
        195                 200                 205

Gly Ala Ala Asn Gly Pro Ala Asp Ser Gly Asp Ala Leu Leu Glu Arg
```

```
            210                 215                 220
Asn Tyr Pro Thr Gly Ala Glu Phe Leu Gly Asp Gly Asp Val Ser
225                 230                 235                 240

Phe Ser Thr Arg Gly Thr Gln Asn Trp Thr Val Glu Arg Leu Leu Gln
                245                 250                 255

Ala His Arg Gln Leu Glu Glu Arg Gly Tyr Val Phe Val Gly Tyr His
                260                 265                 270

Gly Thr Phe Leu Glu Ala Ala Gln Ser Ile Val Phe Gly Val Arg
            275                 280                 285

Ala Arg Ser Gln Asp Leu Asp Ala Ile Trp Arg Gly Phe Tyr Ile Ala
290                 295                 300

Gly Asp Pro Ala Leu Ala Tyr Gly Tyr Ala Gln Asp Gln Glu Pro Asp
305                 310                 315                 320

Ala Arg Gly Arg Ile Arg Asn Gly Ala Leu Leu Arg Val Tyr Val Pro
                325                 330                 335

Arg Ser Ser Leu Pro Gly Phe Tyr Arg Thr Ser Leu Thr Leu Ala Ala
            340                 345                 350

Pro Glu Ala Ala Gly Glu Val Glu Arg Leu Ile Gly His Pro Leu Pro
            355                 360                 365

Leu Arg Leu Asp Ala Ile Thr Gly Pro Glu Glu Gly Gly Arg Leu
370                 375                 380

Glu Thr Ile Leu Gly Trp Pro Leu Ala Glu Arg Thr Val Val Ile Pro
385                 390                 395                 400

Ser Ala Ile Pro Thr Asp Pro Arg Asn Val Gly Gly Asp Leu Asp Pro
                405                 410                 415

Ser Ser Ile Pro Asp Lys Glu Gln Ala Ile Ser Ala Leu Pro Asp Tyr
            420                 425                 430

Ala Ser Gln Pro Gly Lys Pro Pro Arg Glu Asp Leu Lys Arg Ser Ala
            435                 440                 445

Glu Glu Gln Lys Leu Ile Ser Glu Glu Asp Leu Ala His His His His
            450                 455                 460

His His
465

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcaccatgg cacgagggac caacgtgggc cgggagt                               37

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atactcgagg ctacccccac cgccagagcc accaccacca gacctctcaa ggctttgcag     60
gta                                                                   63
```

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atactcgagg gtggtggtgg ttctaaaccg ccgcagttca cttgggct                48

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcggatccg atgatacggt ccagatgaac cggaac                             36

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatcatatgc tcgagggtgg cggtggaagc caggataact ccaggtacac acacttcct    59

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actggatccc ggacgacgga aaattgactg a                                  31

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ataaccatgg aagcttctgg aggtcccgag ggcggcagcc tggccgcgct ga           52

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tatagatctc ttcaggtcct cgcgcggcgg tttgccgggc tggct                   45

<210> SEQ ID NO 19

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaaacagcac attcccagag ttc                                              23

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atggcccagc ggatgag                                                     17

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtggaaggg ctcatgacca cagtccat                                         28

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctgcttca ccaccttctt gatg                                             24

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Val Pro Arg Asn Gln Asp Trp Leu
1               5

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Leu Trp Phe Arg Asn His Phe Val Phe Gly Gly Gly Thr Lys
1               5                   10                  15
```

```
<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 25

His His His His His His
1               5
```